US005681746A

United States Patent [19]

Bodner et al.

[11] Patent Number: 5,681,746

[45] Date of Patent: Oct. 28, 1997

[54] RETROVIRAL DELIVERY OF FULL LENGTH FACTOR VIII

[75] Inventors: Mordechai Bodner, San Diego; Nicholas J. De Polo, Solana Beach; Stephen Chang, Poway; David Chi-Tang Hsu; James G. Respess, both of San Diego, all of Calif.

[73] Assignee: Chiron Viagene, Inc.

[21] Appl. No.: 366,851

[22] Filed: Dec. 30, 1994

[51] Int. Cl.$^6$ .............................. C12N 5/00; C12N 15/63; C07H 21/04

[52] U.S. Cl. .......................... 435/350; 435/366; 435/371; 435/320.1; 536/23.5

[58] Field of Search .......................... 514/44; 435/320.1, 435/70, 350, 336, 371; 424/93.21; 536/23.5

[56] References Cited

U.S. PATENT DOCUMENTS 4,757,006 7/1988 Toole, Jr. et al. .......................... 435/70

FOREIGN PATENT DOCUMENTS 0 260 148 3/1988 European Pat. Off. ............ 435/172.1

OTHER PUBLICATIONS

Marshall, Eliot, "Gene Therapy's Growing Pains", Science, vol. 269, pp. 1050–1055, Aug. 25, 1995.

Brownlee, G. G., British Medical Bulletin, vol. 51, pp. 91–105, 1995.

Hoeben, R. C. et al., Critical Reviews in Oncology/Hematology, vol. 13, pp. 33–54, Jul. 1992.

Matsushita, T., Thrombosis Research, vol. 69, pp. 387–393, Feb. 15, 1993.

Wood et al., Nature, vol. 312, pp. 330–337, 1984.

Hoeben, R. C. et al., Thrombosis and Haemostasis, vol. 67, pp. 341–345, 1992.

Toole et al., Proc. Natl. Acad. Sci., vol. 83, pp. 5939–5942, 1986.

Toole et al., Nature, vol. 312, pp. 342–347, 1984.

*Primary Examiner*—Deborah Crouch
*Assistant Examiner*—Jill Schmuck
*Attorney, Agent, or Firm*—Norman J. Kruse; Robert P. Blackburn

[57] ABSTRACT

Retroviral vectors for directing expression of full length factor VIII in transduced host cells, plasmids encoding the same, and host cells transformed, transfected, or transduced therewith are disclosed. Also disclosed are retroviral particles comprising such retrovital vectors, as are methods for making such particles in suitable packaging cells. Retroviral particles so produced may be amphotropic, ecotropic, polytropic, or xenotropic; alternatively, they may comprise chimeric or hybrid envelope proteins to alter host range. Also described are retrovital particles comprising retroviral vectors for directing full length factor VIII expression which are complement resistant. Pharmaceutical compositions comprising retrovital particles of the invention are also disclosed, as are methods of treating mammals, particularly humans, afflicted with hemophilia.

14 Claims, 5 Drawing Sheets

| FACTOR | NAME |
|---|---|
| I | FIBRINOGEN |
| II | PROTHROMBIN |
| III | TISSUE FACTOR |
| IV | CALCIUM |
| V | PROACCELERIN,LABILE FACTOR |
| VII | PROCONVERTIN,STABLE FACTOR |
| VIII | ANTIHEMOPHILIC A FACTOR (AHF),ANTIHEMOPHILIC GLOBULIN (AHG) |
| IX | ANTIHEMOPHILIC B FACTOR (AHB),PLASMA THROMBOPLASTIN COMPONENT (PTC),CHRISTMAS FACTOR |
| X | STUART FACTOR,STUART-PROWER FACTOR |
| XI | PLASMA THROMBOPLASTIN ANTECEDENT (PTA) |
| XII | HAGEMAN FACTOR,CONTACT FACTOR |
| XIII | FIBRIN STABILIZING FACTOR |
| – | FLETCHER FACTOR,PREKALLIKREIN |
| – | HIGH MOLECULAR WEIGHT KININOGEN,HMWK,FITZGERALD FACTOR |

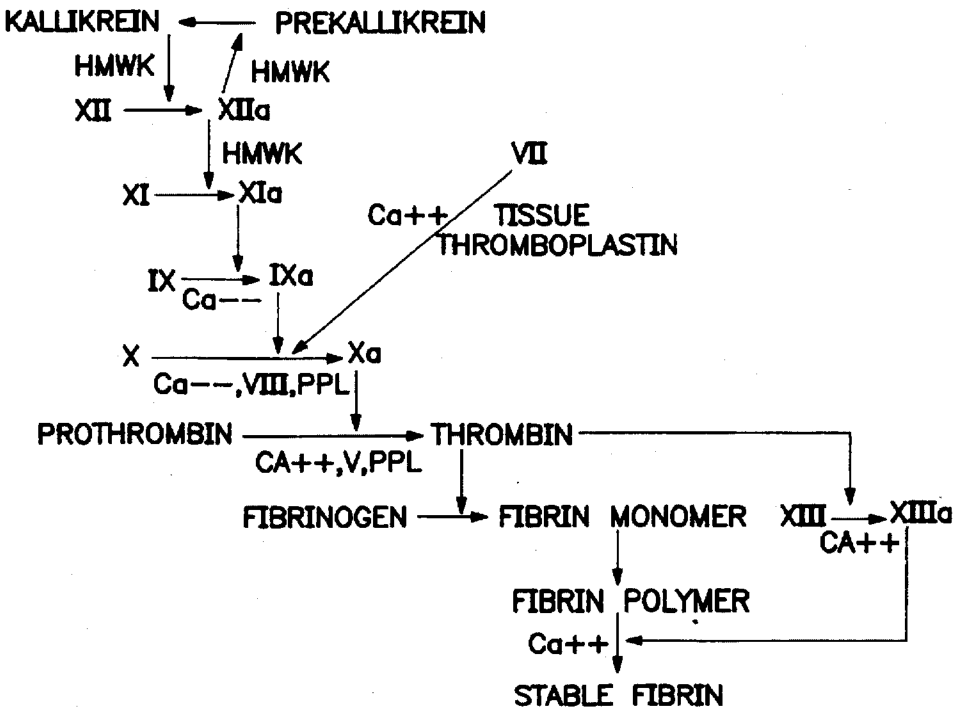

FIG. 2

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
( A ) LENGTH: 8967 base pairs
( B ) TYPE: nucleic acid
( C ) STRANDEDNESS: both
( D ) TOPOLOGY: unknown ( i i ) MOLECULE TYPE: cDNA ( i x ) FEATURE:
( A ) NAME/KEY: CDS
( B ) LOCATION: 110..7165

( x i ) SEQUENCE DESCRIPTION: SEQ ID NO:1:

```
CTTTTCATTA AATCAGAAAT TTTACTTTTT TCCCCTCCTG GGAGCTAAAG ATATTTTAGA      60

GAAGAATTAA CCTTTTGCTT CTCCAGTTGA ACATTTGTAG CAATAAGTC ATG CAA         115
                                                      Met Gln
                                                        1

ATA GAG CTC TCC ACC TGC TTC TTT CTG TGC CTT TTG CGA TTC TGC TTT       163
Ile Glu Leu Ser Thr Cys Phe Phe Leu Cys Leu Leu Arg Phe Cys Phe
         5                  10                  15

AGT GCC ACC AGA AGA TAC TAC CTG GGT GCA GTG GAA CTG TCA TGG GAC       211
Ser Ala Thr Arg Arg Tyr Tyr Leu Gly Ala Val Glu Leu Ser Trp Asp
     20                  25                  30

TAT ATG CAA AGT GAT CTC GGT GAG CTG CCT GTG GAC GCA AGA TTT CCT       259
Tyr Met Gln Ser Asp Leu Gly Glu Leu Pro Val Asp Ala Arg Phe Pro
 35                  40                  45                  50

CCT AGA GTG CCA AAA TCT TTT CCA TTC AAC ACC TCA GTC GTG TAC AAA       307
Pro Arg Val Pro Lys Ser Phe Pro Phe Asn Thr Ser Val Val Tyr Lys
                 55                  60                  65

AAG ACT CTG TTT GTA GAA TTC ACG GAT CAC CTT TTC AAC ATC GCT AAG       355
Lys Thr Leu Phe Val Glu Phe Thr Asp His Leu Phe Asn Ile Ala Lys
             70                  75                  80

CCA AGG CCA CCC TGG ATG GGT CTG CTA GGT CCT ACC ATC CAG GCT GAG       403
Pro Arg Pro Pro Trp Met Gly Leu Leu Gly Pro Thr Ile Gln Ala Glu
         85                  90                  95
```

-continued

```
GTT TAT GAT ACA GTG GTC ATT ACA CTT AAG AAC ATG GCT TCC CAT CCT   451
Val Tyr Asp Thr Val Val Ile Thr Leu Lys Asn Met Ala Ser His Pro
    100                 105                     110

GTC AGT CTT CAT GCT GTT GGT GTA TCC TAC TGG AAA GCT TCT GAG GGA   499
Val Ser Leu His Ala Val Gly Val Ser Tyr Trp Lys Ala Ser Glu Gly
115                 120                 125                 130

GCT GAA TAT GAT GAT CAG ACC AGT CAA AGG GAG AAA GAA GAT GAT AAA   547
Ala Glu Tyr Asp Asp Gln Thr Ser Gln Arg Glu Lys Glu Asp Asp Lys
                135                 140                 145

GTC TTC CCT GGT GGA AGC CAT ACA TAT GTC TGG CAG GTC CTG AAA GAG   595
Val Phe Pro Gly Gly Ser His Thr Tyr Val Trp Gln Val Leu Lys Glu
            150                 155                 160

AAT GGT CCA ATG GCC TCT GAC CCA CTG TGC CTT ACC TAC TCA TAT CTT   643
Asn Gly Pro Met Ala Ser Asp Pro Leu Cys Leu Thr Tyr Ser Tyr Leu
        165                 170                 175

TCT CAT GTG GAC CTG GTA AAA GAC TTG AAT TCA GGC CTC ATT GGA GCC   691
Ser His Val Asp Leu Val Lys Asp Leu Asn Ser Gly Leu Ile Gly Ala
    180                 185                 190

CTA CTA GTA TGT AGA GAA GGG AGT CTG GCC AAG GAA AAG ACA CAG ACC   739
Leu Leu Val Cys Arg Glu Gly Ser Leu Ala Lys Glu Lys Thr Gln Thr
195                 200                 205                 210

TTG CAC AAA TTT ATA CTA CTT TTT GCT GTA TTT GAT GAA GGG AAA AGT   787
Leu His Lys Phe Ile Leu Leu Phe Ala Val Phe Asp Glu Gly Lys Ser
                215                 220                 225

TGG CAC TCA GAA ACA AAG AAC TCC TTG ATG CAG GAT AGG GAT GCT GCA   835
Trp His Ser Glu Thr Lys Asn Ser Leu Met Gln Asp Arg Asp Ala Ala
            230                 235                 240

TCT GCT CGG GCC TGG CCT AAA ATG CAC ACA GTC AAT GGT TAT GTA AAC   883
Ser Ala Arg Ala Trp Pro Lys Met His Thr Val Asn Gly Tyr Val Asn
        245                 250                 255

AGG TCT CTG CCA GGT CTG ATT GGA TGC CAC AGG AAA TCA GTC TAT TGG   931
Arg Ser Leu Pro Gly Leu Ile Gly Cys His Arg Lys Ser Val Tyr Trp
    260                 265                 270

CAT GTG ATT GGA ATG GGC ACC ACT CCT GAA GTG CAC TCA ATA TTC CTC   979
His Val Ile Gly Met Gly Thr Thr Pro Glu Val His Ser Ile Phe Leu
275                 280                 285                 290

GAA GGT CAC ACA TTT CTT GTG AGG AAC CAT CGC CAG GCG TCC TTG GAA   1027
Glu Gly His Thr Phe Leu Val Arg Asn His Arg Gln Ala Ser Leu Glu
                295                 300                 305

ATC TCG CCA ATA ACT TTC CTT ACT GCT CAA ACA CTC TTG ATG GAC CTT   1075
Ile Ser Pro Ile Thr Phe Leu Thr Ala Gln Thr Leu Leu Met Asp Leu
            310                 315                 320

GGA CAG TTT CTA CTG TTT TGT CAT ATC TCT TCC CAC CAA CAT GAT GGC   1123
Gly Gln Phe Leu Leu Phe Cys His Ile Ser Ser His Gln His Asp Gly
        325                 330                 335

ATG GAA GCT TAT GTC AAA GTA GAC AGC TGT CCA GAG GAA CCC CAA CTA   1171
Met Glu Ala Tyr Val Lys Val Asp Ser Cys Pro Glu Glu Pro Gln Leu
    340                 345                 350

CGA ATG AAA AAT AAT GAA GAA GCG GAA GAC TAT GAT GAT GAT CTT ACT   1219
Arg Met Lys Asn Asn Glu Glu Ala Glu Asp Tyr Asp Asp Asp Leu Thr
355                 360                 365                 370

GAT TCT GAA ATG GAT GTG GTC AGG TTT GAT GAT GAC AAC TCT CCT TCC   1267
Asp Ser Glu Met Asp Val Val Arg Phe Asp Asp Asp Asn Ser Pro Ser
                375                 380                 385

TTT ATC CAA ATT CGC TCA GTT GCC AAG AAG CAT CCT AAA ACT TGG GTA   1315
Phe Ile Gln Ile Arg Ser Val Ala Lys Lys His Pro Lys Thr Trp Val
            390                 395                 400

CAT TAC ATT GCT GCT GAA GAG GAG GAC TGG GAC TAT GCT CCC TTA GTC   1363
His Tyr Ile Ala Ala Glu Glu Glu Asp Trp Asp Tyr Ala Pro Leu Val
        405                 410                 415
```

-continued

CTC GCC CCC GAT GAC AGA AGT TAT AAA AGT CAA TAT TTG AAC AAT GGC 1411
Leu Ala Pro Asp Asp Arg Ser Tyr Lys Ser Gln Tyr Leu Asn Asn Gly
420 425 430

CCT CAG CGG ATT GGT AGG AAG TAC AAA AAA GTC CGA TTT ATG GCA TAC 1459
Pro Gln Arg Ile Gly Arg Lys Tyr Lys Lys Val Arg Phe Met Ala Tyr
435 440 445 450

ACA GAT GAA ACC TTT AAG ACT CGT GAA GCT ATT CAG CAT GAA TCA GGA 1507
Thr Asp Glu Thr Phe Lys Thr Arg Glu Ala Ile Gln His Glu Ser Gly
455 460 465

ATC TTG GGA CCT TTA CTT TAT GGG GAA GTT GGA GAC ACA CTG TTG ATT 1555
Ile Leu Gly Pro Leu Leu Tyr Gly Glu Val Gly Asp Thr Leu Leu Ile
470 475 480

ATA TTT AAG AAT CAA GCA AGC AGA CCA TAT AAC ATC TAC CCT CAC GGA 1603
Ile Phe Lys Asn Gln Ala Ser Arg Pro Tyr Asn Ile Tyr Pro His Gly
485 490 495

ATC ACT GAT GTC CGT CCT TTG TAT TCA AGG AGA TTA CCA AAA GGT GTA 1651
Ile Thr Asp Val Arg Pro Leu Tyr Ser Arg Arg Leu Pro Lys Gly Val
500 505 510

AAA CAT TTG AAG GAT TTT CCA ATT CTG CCA GGA GAA ATA TTC AAA TAT 1699
Lys His Leu Lys Asp Phe Pro Ile Leu Pro Gly Glu Ile Phe Lys Tyr
515 520 525 530

AAA TGG ACA GTG ACT GTA GAA GAT GGG CCA ACT AAA TCA GAT CCT CGG 1747
Lys Trp Thr Val Thr Val Glu Asp Gly Pro Thr Lys Ser Asp Pro Arg
535 540 545

TGC CTG ACC CGC TAT TAC TCT AGT TTC GTT AAT ATG GAG AGA GAT CTA 1795
Cys Leu Thr Arg Tyr Tyr Ser Ser Phe Val Asn Met Glu Arg Asp Leu
550 555 560

GCT TCA GGA CTC ATT GGC CCT CTC CTC ATC TGC TAC AAA GAA TCT GTA 1843
Ala Ser Gly Leu Ile Gly Pro Leu Leu Ile Cys Tyr Lys Glu Ser Val
565 570 575

GAT CAA AGA GGA AAC CAG ATA ATG TCA GAC AAG AGG AAT GTC ATC CTG 1891
Asp Gln Arg Gly Asn Gln Ile Met Ser Asp Lys Arg Asn Val Ile Leu
580 585 590

TTT TCT GTA TTT GAT GAG AAC CGA AGC TGG TAC CTC ACA GAG AAT ATA 1939
Phe Ser Val Phe Asp Glu Asn Arg Ser Trp Tyr Leu Thr Glu Asn Ile
595 600 605 610

CAA CGC TTT CTC CCC AAT CCA GCT GGA GTG CAG CTT GAG GAT CCA GAG 1987
Gln Arg Phe Leu Pro Asn Pro Ala Gly Val Gln Leu Glu Asp Pro Glu
615 620 625

TTC CAA GCC TCC AAC ATC ATG CAC AGC ATC AAT GGC TAT GTT TTT GAT 2035
Phe Gln Ala Ser Asn Ile Met His Ser Ile Asn Gly Tyr Val Phe Asp
630 635 640

AGT TTG CAG TTG TCA GTT TGT TTG CAT GAG GTG GCA TAC TGG TAC ATT 2083
Ser Leu Gln Leu Ser Val Cys Leu His Glu Val Ala Tyr Trp Tyr Ile
645 650 655

CTA AGC ATT GGA GCA CAG ACT GAC TTC CTT TCT GTC TTC TTC TCT GGA 2131
Leu Ser Ile Gly Ala Gln Thr Asp Phe Leu Ser Val Phe Phe Ser Gly
660 665 670

TAT ACC TTC AAA CAC AAA ATG GTC TAT GAA GAC ACA CTC ACC CTA TTC 2179
Tyr Thr Phe Lys His Lys Met Val Tyr Glu Asp Thr Leu Thr Leu Phe
675 680 685 690

CCA TTC TCA GGA GAA ACT GTC TTC ATG TCG ATG GAA AAC CCA GGT CTA 2227
Pro Phe Ser Gly Glu Thr Val Phe Met Ser Met Glu Asn Pro Gly Leu
695 700 705

TGG ATT CTG GGG TGC CAC AAC TCA GAC TTT CGG AAC AGA GGC ATG ACC 2275
Trp Ile Leu Gly Cys His Asn Ser Asp Phe Arg Asn Arg Gly Met Thr
710 715 720

GCC TTA CTG AAG GTT TCT AGT TGT GAC AAG AAC ACT GGT GAT TAT TAC 2323
Ala Leu Leu Lys Val Ser Ser Cys Asp Lys Asn Thr Gly Asp Tyr Tyr
725 730 735

-continued

GAG GAC AGT TAT GAA GAT ATT TCA GCA TAC TTG CTG AGT AAA AAC AAT 2371
Glu Asp Ser Tyr Glu Asp Ile Ser Ala Tyr Leu Leu Ser Lys Asn Asn
740 745 750

GCC ATT GAA CCA AGA AGC TTC TCC CAG AAT TCA AGA CAC CGT AGC ACT 2419
Ala Ile Glu Pro Arg Ser Phe Ser Gln Asn Ser Arg His Arg Ser Thr
755 760 765 770

AGG CAA AAG CAA TTT AAT GCC ACC ACA ATT CCA GAA AAT GAC ATA GAG 2467
Arg Gln Lys Gln Phe Asn Ala Thr Thr Ile Pro Glu Asn Asp Ile Glu
775 780 785

AAG ACT GAC CCT TGG TTT GCA CAC AGA ACA CCT ATG CCT AAA ATA CAA 2515
Lys Thr Asp Pro Trp Phe Ala His Arg Thr Pro Met Pro Lys Ile Gln
790 795 800

AAT GTC TCC TCT AGT GAT TTG TTG ATG CTC TTG CGA CAG AGT CCT ACT 2563
Asn Val Ser Ser Ser Asp Leu Leu Met Leu Leu Arg Gln Ser Pro Thr
805 810 815

CCA CAT GGG CTA TCC TTA TCT GAT CTC CAA GAA GCC AAA TAT GAG ACT 2611
Pro His Gly Leu Ser Leu Ser Asp Leu Gln Glu Ala Lys Tyr Glu Thr
820 825 830

TTT TCT GAT GAT CCA TCA CCT GGA GCA ATA GAC AGT AAT AAC AGC CTG 2659
Phe Ser Asp Asp Pro Ser Pro Gly Ala Ile Asp Ser Asn Asn Ser Leu
835 840 845 850

TCT GAA ATG ACA CAC TTC AGG CCA CAG CTC CAT CAC AGT GGG GAC ATG 2707
Ser Glu Met Thr His Phe Arg Pro Gln Leu His His Ser Gly Asp Met
855 860 865

GTA TTT ACC CCT GAG TCA GGC CTC CAA TTA AGA TTA AAT GAG AAA CTG 2755
Val Phe Thr Pro Glu Ser Gly Leu Gln Leu Arg Leu Asn Glu Lys Leu
870 875 880

GGG ACA ACT GCA GCA ACA GAG TTG AAG AAA CTT GAT TTC AAA GTT TCT 2803
Gly Thr Thr Ala Ala Thr Glu Leu Lys Lys Leu Asp Phe Lys Val Ser
885 890 895

AGT ACA TCA AAT AAT CTG ATT TCA ACA ATT CCA TCA GAC AAT TTG GCA 2851
Ser Thr Ser Asn Asn Leu Ile Ser Thr Ile Pro Ser Asp Asn Leu Ala
900 905 910

GCA GGT ACT GAT AAT ACA AGT TCC TTA GGA CCC CCA AGT ATG CCA GTT 2899
Ala Gly Thr Asp Asn Thr Ser Ser Leu Gly Pro Pro Ser Met Pro Val
915 920 925 930

CAT TAT GAT AGT CAA TTA GAT ACC ACT CTA TTT GGC AAA AAG TCA TCT 2947
His Tyr Asp Ser Gln Leu Asp Thr Thr Leu Phe Gly Lys Lys Ser Ser
935 940 945

CCC CTT ACT GAG TCT GGT GGA CCT CTG AGC TTG AGT GAA GAA AAT AAT 2995
Pro Leu Thr Glu Ser Gly Gly Pro Leu Ser Leu Ser Glu Glu Asn Asn
950 955 960

GAT TCA AAG TTG TTA GAA TCA GGT TTA ATG AAT AGC CAA GAA AGT TCA 3043
Asp Ser Lys Leu Leu Glu Ser Gly Leu Met Asn Ser Gln Glu Ser Ser
965 970 975

TGG GGA AAA AAT GTA TCG TCA ACA GAG AGT GGT AGG TTA TTT AAA GGG 3091
Trp Gly Lys Asn Val Ser Ser Thr Glu Ser Gly Arg Leu Phe Lys Gly
980 985 990

AAA AGA GCT CAT GGA CCT GCT TTG TTG ACT AAA GAT AAT GCC TTA TTC 3139
Lys Arg Ala His Gly Pro Ala Leu Leu Thr Lys Asp Asn Ala Leu Phe
995 1000 1005 1010

AAA GTT AGC ATC TCT TTG TTA AAG ACA AAC AAA ACT TCC AAT AAT TCA 3187
Lys Val Ser Ile Ser Leu Leu Lys Thr Asn Lys Thr Ser Asn Asn Ser
1015 1020 1025

GCA ACT AAT AGA AAG ACT CAC ATT GAT GGC CCA TCA TTA TTA ATT GAG 3235
Ala Thr Asn Arg Lys Thr His Ile Asp Gly Pro Ser Leu Leu Ile Glu
1030 1035 1040

AAT AGT CCA TCA GTC TGG CAA AAT ATA TTA GAA AGT GAC ACT GAG TTT 3283
Asn Ser Pro Ser Val Trp Gln Asn Ile Leu Glu Ser Asp Thr Glu Phe
1045 1050 1055

-continued

AAA AAA GTG ACA CCT TTG ATT CAT GAC AGA ATG CTT ATG GAC AAA AAT 3331
Lys Lys Val Thr Pro Leu Ile His Asp Arg Met Leu Met Asp Lys Asn
1060 1065 1070

GCT ACA GCT TTG AGG CTA AAT CAT ATG TCA AAT AAA ACT ACT TCA TCA 3379
Ala Thr Ala Leu Arg Leu Asn His Met Ser Asn Lys Thr Thr Ser Ser
1075 1080 1085 1090

AAA AAC ATG GAA ATG GTC CAA CAG AAA AAA GAG GGC CCC ATT CCA CCA 3427
Lys Asn Met Glu Met Val Gln Gln Lys Lys Glu Gly Pro Ile Pro Pro
1095 1100 1105

GAT GCA CAA AAT CCA GAT ATG TCG TTC TTT AAG ATG CTA TTC TTG CCA 3475
Asp Ala Gln Asn Pro Asp Met Ser Phe Phe Lys Met Leu Phe Leu Pro
1110 1115 1120

GAA TCA GCA AGG TGG ATA CAA AGG ACT CAT GGA AAG AAC TCT CTG AAC 3523
Glu Ser Ala Arg Trp Ile Gln Arg Thr His Gly Lys Asn Ser Leu Asn
1125 1130 1135

TCT GGG CAA GGC CCC AGT CCA AAG CAA TTA GTA TCC TTA GGA CCA GAA 3571
Ser Gly Gln Gly Pro Ser Pro Lys Gln Leu Val Ser Leu Gly Pro Glu
1140 1145 1150

AAA TCT GTG GAA GGT CAG AAT TTC TTG TCT GAG AAA AAC AAA GTG GTA 3619
Lys Ser Val Glu Gly Gln Asn Phe Leu Ser Glu Lys Asn Lys Val Val
1155 1160 1165 1170

GTA GGA AAG GGT GAA TTT ACA AAG GAC GTA GGA CTC AAA GAG ATG GTT 3667
Val Gly Lys Gly Glu Phe Thr Lys Asp Val Gly Leu Lys Glu Met Val
1175 1180 1185

TTT CCA AGC AGC AGA AAC CTA TTT CTT ACT AAC TTG GAT AAT TTA CAT 3715
Phe Pro Ser Ser Arg Asn Leu Phe Leu Thr Asn Leu Asp Asn Leu His
1190 1195 1200

GAA AAT AAT ACA CAC AAT CAA GAA AAA AAA ATT CAG GAA GAA ATA GAA 3763
Glu Asn Asn Thr His Asn Gln Glu Lys Lys Ile Gln Glu Glu Ile Glu
1205 1210 1215

AAG AAG GAA ACA TTA ATC CAA GAG AAT GTA GTT TTG CCT CAG ATA CAT 3811
Lys Lys Glu Thr Leu Ile Gln Glu Asn Val Val Leu Pro Gln Ile His
1220 1225 1230

ACA GTG ACT GGC ACT AAG AAT TTC ATG AAG AAC CTT TTC TTA CTG AGC 3859
Thr Val Thr Gly Thr Lys Asn Phe Met Lys Asn Leu Phe Leu Leu Ser
1235 1240 1245 1250

ACT AGG CAA AAT GTA GAA GGT TCA TAT GAC GGG GCA TAT GCT CCA GTA 3907
Thr Arg Gln Asn Val Glu Gly Ser Tyr Asp Gly Ala Tyr Ala Pro Val
1255 1260 1265

CTT CAA GAT TTT AGG TCA TTA AAT GAT TCA ACA AAT AGA ACA AAG AAA 3955
Leu Gln Asp Phe Arg Ser Leu Asn Asp Ser Thr Asn Arg Thr Lys Lys
1270 1275 1280

CAC ACA GCT CAT TTC TCA AAA AAA GGG GAG GAA GAA AAC TTG GAA GGC 4003
His Thr Ala His Phe Ser Lys Lys Gly Glu Glu Glu Asn Leu Glu Gly
1285 1290 1295

TTG GGA AAT CAA ACC AAG CAA ATT GTA GAG AAA TAT GCA TGC ACC ACA 4051
Leu Gly Asn Gln Thr Lys Gln Ile Val Glu Lys Tyr Ala Cys Thr Thr
1300 1305 1310

AGG ATA TCT CCT AAT ACA AGC CAG CAG AAT TTT GTC ACG CAA CGT AGT 4099
Arg Ile Ser Pro Asn Thr Ser Gln Gln Asn Phe Val Thr Gln Arg Ser
1315 1320 1325 1330

AAG AGA GCT TTG AAA CAA TTC AGA CTC CCA CTA GAA GAA ACA GAA CTT 4147
Lys Arg Ala Leu Lys Gln Phe Arg Leu Pro Leu Glu Glu Thr Glu Leu
1335 1340 1345

GAA AAA AGG ATA ATT GTG GAT GAC ACC TCA ACC CAG TGG TCC AAA AAC 4195
Glu Lys Arg Ile Ile Val Asp Asp Thr Ser Thr Gln Trp Ser Lys Asn
1350 1355 1360

ATG AAA CAT TTG ACC CCG AGC ACC CTC ACA CAG ATA GAC TAC AAT GAG 4243
Met Lys His Leu Thr Pro Ser Thr Leu Thr Gln Ile Asp Tyr Asn Glu
1365 1370 1375

-continued

AAG GAG AAA GGG GCC ATT ACT CAG TCT CCC TTA TCA GAT TGC CTT ACG 4291
Lys Glu Lys Gly Ala Ile Thr Gln Ser Pro Leu Ser Asp Cys Leu Thr
1380 1385 1390

AGG AGT CAT AGC ATC CCT CAA GCA AAT AGA TCT CCA TTA CCC ATT GCA 4339
Arg Ser His Ser Ile Pro Gln Ala Asn Arg Ser Pro Leu Pro Ile Ala
1395 1400 1405 1410

AAG GTA TCA TCA TTT CCA TCT ATT AGA CCT ATA TAT CTG ACC AGG GTC 4387
Lys Val Ser Ser Phe Pro Ser Ile Arg Pro Ile Tyr Leu Thr Arg Val
1415 1420 1425

CTA TTC CAA GAC AAC TCT TCT CAT CTT CCA GCA GCA TCT TAT AGA AAG 4435
Leu Phe Gln Asp Asn Ser Ser His Leu Pro Ala Ala Ser Tyr Arg Lys
1430 1435 1440

AAA GAT TCT GGG GTC CAA GAA AGC AGT CAT TTC TTA CAA GGA GCC AAA 4483
Lys Asp Ser Gly Val Gln Glu Ser Ser His Phe Leu Gln Gly Ala Lys
1445 1450 1455

AAA AAT AAC CTT TCT TTA GCC ATT CTA ACC TTG GAG ATG ACT GGT GAT 4531
Lys Asn Asn Leu Ser Leu Ala Ile Leu Thr Leu Glu Met Thr Gly Asp
1460 1465 1470

CAA AGA GAG GTT GGC TCC CTG GGG ACA AGT GCC ACA AAT TCA GTC ACA 4579
Gln Arg Glu Val Gly Ser Leu Gly Thr Ser Ala Thr Asn Ser Val Thr
1475 1480 1485 1490

TAC AAG AAA GTT GAG AAC ACT GTT CTC CCG AAA CCA GAC TTG CCC AAA 4627
Tyr Lys Lys Val Glu Asn Thr Val Leu Pro Lys Pro Asp Leu Pro Lys
1495 1500 1505

ACA TCT GGC AAA GTT GAA TTG CTT CCA AAA GTT CAC ATT TAT CAG AAG 4675
Thr Ser Gly Lys Val Glu Leu Leu Pro Lys Val His Ile Tyr Gln Lys
1510 1515 1520

GAC CTA TTC CCT ACG GAA ACT AGC AAT GGG TCT CCT GGC CAT CTG GAT 4723
Asp Leu Phe Pro Thr Glu Thr Ser Asn Gly Ser Pro Gly His Leu Asp
1525 1530 1535

CTC GTG GAA GGG AGC CTT CTT CAG GGA ACA GAG GGA GCG ATT AAG TGG 4771
Leu Val Glu Gly Ser Leu Leu Gln Gly Thr Glu Gly Ala Ile Lys Trp
1540 1545 1550

AAT GAA GCA AAC AGA CCT GGA AAA GTT CCC TTT CTG AGA GTA GCA ACA 4819
Asn Glu Ala Asn Arg Pro Gly Lys Val Pro Phe Leu Arg Val Ala Thr
1555 1560 1565 1570

GAA AGC TCT GCA AAG ACT CCC TCC AAG CTA TTG GAT CCT CTT GCT TGG 4867
Glu Ser Ser Ala Lys Thr Pro Ser Lys Leu Leu Asp Pro Leu Ala Trp
1575 1580 1585

GAT AAC CAC TAT GGT ACT CAG ATA CCA AAA GAA GAG TGG AAA TCC CAA 4915
Asp Asn His Tyr Gly Thr Gln Ile Pro Lys Glu Glu Trp Lys Ser Gln
1590 1595 1600

GAG AAG TCA CCA GAA AAA ACA GCT TTT AAG AAA AAG GAT ACC ATT TTG 4963
Glu Lys Ser Pro Glu Lys Thr Ala Phe Lys Lys Lys Asp Thr Ile Leu
1605 1610 1615

TCC CTG AAC GCT TGT GAA AGC AAT CAT GCA ATA GCA GCA ATA AAT GAG 5011
Ser Leu Asn Ala Cys Glu Ser Asn His Ala Ile Ala Ala Ile Asn Glu
1620 1625 1630

GGA CAA AAT AAG CCC GAA ATA GAA GTC ACC TGG GCA AAG CAA GGT AGG 5059
Gly Gln Asn Lys Pro Glu Ile Glu Val Thr Trp Ala Lys Gln Gly Arg
1635 1640 1645 1650

ACT GAA AGG CTG TGC TCT CAA AAC CCA CCA GTC TTG AAA CGC CAT CAA 5107
Thr Glu Arg Leu Cys Ser Gln Asn Pro Pro Val Leu Lys Arg His Gln
1655 1660 1665

CGG GAA ATA ACT CGT ACT ACT CTT CAG TCA GAT CAA GAG GAA ATT GAC 5155
Arg Glu Ile Thr Arg Thr Thr Leu Gln Ser Asp Gln Glu Glu Ile Asp
1670 1675 1680

TAT GAT GAT ACC ATA TCA GTT GAA ATG AAG AAG GAA GAT TTT GAC ATT 5203
Tyr Asp Asp Thr Ile Ser Val Glu Met Lys Lys Glu Asp Phe Asp Ile
1685 1690 1695

-continued

TAT GAT GAG GAT GAA AAT CAG AGC CCC CGC AGC TTT CAA AAG AAA ACA 5251
Tyr Asp Glu Asp Glu Asn Gln Ser Pro Arg Ser Phe Gln Lys Lys Thr
1700 1705 1710

CGA CAC TAT TTT ATT GCT GCA GTG GAG AGG CTC TGG GAT TAT GGG ATG 5299
Arg His Tyr Phe Ile Ala Ala Val Glu Arg Leu Trp Asp Tyr Gly Met
1715 1720 1725 1730

AGT AGC TCC CCA CAT GTT CTA AGA AAC AGG GCT CAG AGT GGC AGT GTC 5347
Ser Ser Ser Pro His Val Leu Arg Asn Arg Ala Gln Ser Gly Ser Val
1735 1740 1745

CCT CAG TTC AAG AAA GTT GTT TTC CAG GAA TTT ACT GAT GGC TCC TTT 5395
Pro Gln Phe Lys Lys Val Val Phe Gln Glu Phe Thr Asp Gly Ser Phe
1750 1755 1760

ACT CAG CCC TTA TAC CGT GGA GAA CTA AAT GAA CAT TTG GGA CTC CTG 5443
Thr Gln Pro Leu Tyr Arg Gly Glu Leu Asn Glu His Leu Gly Leu Leu
1765 1770 1775

GGG CCA TAT ATA AGA GCA GAA GTT GAA GAT AAT ATC ATG GTA ACT TTC 5491
Gly Pro Tyr Ile Arg Ala Glu Val Glu Asp Asn Ile Met Val Thr Phe
1780 1785 1790

AGA AAT CAG GCC TCT CGT CCC TAT TCC TTC TAT TCT AGC CTT ATT TCT 5539
Arg Asn Gln Ala Ser Arg Pro Tyr Ser Phe Tyr Ser Ser Leu Ile Ser
1795 1800 1805 1810

TAT GAG GAA GAT CAG AGG CAA GGA GCA GAA CCT AGA AAA AAC TTT GTC 5587
Tyr Glu Glu Asp Gln Arg Gln Gly Ala Glu Pro Arg Lys Asn Phe Val
1815 1820 1825

AAG CCT AAT GAA ACC AAA ACT TAC TTT TGG AAA GTG CAA CAT CAT ATG 5635
Lys Pro Asn Glu Thr Lys Thr Tyr Phe Trp Lys Val Gln His His Met
1830 1835 1840

GCA CCC ACT AAA GAT GAG TTT GAC TGC AAA GCC TGG GCT TAT TTC TCT 5683
Ala Pro Thr Lys Asp Glu Phe Asp Cys Lys Ala Trp Ala Tyr Phe Ser
1845 1850 1855

GAT GTT GAC CTG GAA AAA GAT GTG CAC TCA GGC CTG ATT GGA CCC CTT 5731
Asp Val Asp Leu Glu Lys Asp Val His Ser Gly Leu Ile Gly Pro Leu
1860 1865 1870

CTG GTC TGC CAC ACT AAC ACA CTG AAC CCT GCT CAT GGG AGA CAA GTG 5779
Leu Val Cys His Thr Asn Thr Leu Asn Pro Ala His Gly Arg Gln Val
1875 1880 1885 1890

ACA GTA CAG GAA TTT GCT CTG TTT TTC ACC ATC TTT GAT GAG ACC AAA 5827
Thr Val Gln Glu Phe Ala Leu Phe Phe Thr Ile Phe Asp Glu Thr Lys
1895 1900 1905

AGC TGG TAC TTC ACT GAA AAT ATG GAA AGA AAC TGC AGG GCT CCC TGC 5875
Ser Trp Tyr Phe Thr Glu Asn Met Glu Arg Asn Cys Arg Ala Pro Cys
1910 1915 1920

AAT ATC CAG ATG GAA GAT CCC ACT TTT AAA GAG AAT TAT CGC TTC CAT 5923
Asn Ile Gln Met Glu Asp Pro Thr Phe Lys Glu Asn Tyr Arg Phe His
1925 1930 1935

GCA ATC AAT GGC TAC ATA ATG GAT ACA CTA CCT GGC TTA GTA ATG GCT 5971
Ala Ile Asn Gly Tyr Ile Met Asp Thr Leu Pro Gly Leu Val Met Ala
1940 1945 1950

CAG GAT CAA AGG ATT CGA TGG TAT CTG CTC AGC ATG GGC AGC AAT GAA 6019
Gln Asp Gln Arg Ile Arg Trp Tyr Leu Leu Ser Met Gly Ser Asn Glu
1955 1960 1965 1970

AAC ATC CAT TCT ATT CAT TTC AGT GGA CAT GTG TTC ACT GTA CGA AAA 6067
Asn Ile His Ser Ile His Phe Ser Gly His Val Phe Thr Val Arg Lys
1975 1980 1985

AAA GAG GAG TAT AAA ATG GCA CTG TAC AAT CTC TAT CCA GGT GTT TTT 6115
Lys Glu Glu Tyr Lys Met Ala Leu Tyr Asn Leu Tyr Pro Gly Val Phe
1990 1995 2000

GAG ACA GTG GAA ATG TTA CCA TCC AAA GCT GGA ATT TGG CGG GTG GAA 6163
Glu Thr Val Glu Met Leu Pro Ser Lys Ala Gly Ile Trp Arg Val Glu
2005 2010 2015

-continued

TGC CTT ATT GGC GAG CAT CTA CAT GCT GGG ATG AGC ACA CTT TTT CTG 6211
Cys Leu Ile Gly Glu His Leu His Ala Gly Met Ser Thr Leu Phe Leu
2020 2025 2030

GTG TAC AGC AAT AAG TGT CAG ACT CCC CTG GGA ATG GCT TCT GGA CAC 6259
Val Tyr Ser Asn Lys Cys Gln Thr Pro Leu Gly Met Ala Ser Gly His
2035 2040 2045 2050

ATT AGA GAT TTT CAG ATT ACA GCT TCA GGA CAA TAT GGA CAG TGG GCC 6307
Ile Arg Asp Phe Gln Ile Thr Ala Ser Gly Gln Tyr Gly Gln Trp Ala
2055 2060 2065

CCA AAG CTG GCC AGA CTT CAT TAT TCC GGA TCA ATC AAT GCC TGG AGC 6355
Pro Lys Leu Ala Arg Leu His Tyr Ser Gly Ser Ile Asn Ala Trp Ser
2070 2075 2080

ACC AAG GAG CCC TTT TCT TGG ATC AAG GTG GAT CTG TTG GCA CCA ATG 6403
Thr Lys Glu Pro Phe Ser Trp Ile Lys Val Asp Leu Leu Ala Pro Met
2085 2090 2095

ATT ATT CAC GGC ATC AAG ACC CAG GGT GCC CGT CAG AAG TTC TCC AGC 6451
Ile Ile His Gly Ile Lys Thr Gln Gly Ala Arg Gln Lys Phe Ser Ser
2100 2105 2110

CTC TAC ATC TCT CAG TTT ATC ATC ATG TAT AGT CTT GAT GGG AAG AAG 6499
Leu Tyr Ile Ser Gln Phe Ile Ile Met Tyr Ser Leu Asp Gly Lys Lys
2115 2120 2125 2130

TGG CAG ACT TAT CGA GGA AAT TCC ACT GGA ACC TTA ATG GTC TTC TTT 6547
Trp Gln Thr Tyr Arg Gly Asn Ser Thr Gly Thr Leu Met Val Phe Phe
2135 2140 2145

GGC AAT GTG GAT TCA TCT GGG ATA AAA CAC AAT ATT TTT AAC CCT CCA 6595
Gly Asn Val Asp Ser Ser Gly Ile Lys His Asn Ile Phe Asn Pro Pro
2150 2155 2160

ATT ATT GCT CGA TAC ATC CGT TTG CAC CCA ACT CAT TAT AGC ATT CGC 6643
Ile Ile Ala Arg Tyr Ile Arg Leu His Pro Thr His Tyr Ser Ile Arg
2165 2170 2175

AGC ACT CTT CGC ATG GAG TTG ATG GGC TGT GAT TTA AAT AGT TGC AGC 6691
Ser Thr Leu Arg Met Glu Leu Met Gly Cys Asp Leu Asn Ser Cys Ser
2180 2185 2190

ATG CCA TTG GGA ATG GAG AGT AAA GCA ATA TCA GAT GCA CAG ATT ACT 6739
Met Pro Leu Gly Met Glu Ser Lys Ala Ile Ser Asp Ala Gln Ile Thr
2195 2200 2205 2210

GCT TCA TCC TAC TTT ACC AAT ATG TTT GCC ACC TGG TCT CCT TCA AAA 6787
Ala Ser Ser Tyr Phe Thr Asn Met Phe Ala Thr Trp Ser Pro Ser Lys
2215 2220 2225

GCT CGA CTT CAC CTC CAA GGG AGG AGT AAT GCC TGG AGA CCT CAG GTG 6835
Ala Arg Leu His Leu Gln Gly Arg Ser Asn Ala Trp Arg Pro Gln Val
2230 2235 2240

AAT AAT CCA AAA GAG TGG CTG CAA GTG GAC TTC CAG AAG ACA ATG AAA 6883
Asn Asn Pro Lys Glu Trp Leu Gln Val Asp Phe Gln Lys Thr Met Lys
2245 2250 2255

GTC ACA GGA GTA ACT ACT CAG GGA GTA AAA TCT CTG CTT ACC AGC ATG 6931
Val Thr Gly Val Thr Thr Gln Gly Val Lys Ser Leu Leu Thr Ser Met
2260 2265 2270

TAT GTG AAG GAG TTC CTC ATC TCC AGC AGT CAA GAT GGC CAT CAG TGG 6979
Tyr Val Lys Glu Phe Leu Ile Ser Ser Ser Gln Asp Gly His Gln Trp
2275 2280 2285 2290

ACT CTC TTT TTT CAG AAT GGC AAA GTA AAG GTT TTT CAG GGA AAT CAA 7027
Thr Leu Phe Phe Gln Asn Gly Lys Val Lys Val Phe Gln Gly Asn Gln
2295 2300 2305

GAC TCC TTC ACA CCT GTG GTG AAC TCT CTA GAC CCA CCG TTA CTG ACT 7075
Asp Ser Phe Thr Pro Val Val Asn Ser Leu Asp Pro Pro Leu Leu Thr
2310 2315 2320

CGC TAC CTT CGA ATT CAC CCC CAG AGT TGG GTG CAC CAG ATT GCC CTG 7123
Arg Tyr Leu Arg Ile His Pro Gln Ser Trp Val His Gln Ile Ala Leu
2325 2330 2335

-continued

```
AGG ATG GAG GTT CTG GGC TGC GAG GCA CAG GAC CTC TAC TGAGGGTGGC        7172
Arg Met Glu Val Leu Gly Cys Glu Ala Gln Asp Leu Tyr
    2340                2345                2350

CACTGCAGCA CCTGCCACTG CCGTCACCTC TCCCTCCTCA GCTCCAGGGC AGTGTCCCTC     7232
CCTGGCTTGC CTTCTACCTT TGTGCTAAAT CCTAGCAGAC ACTGCCTTGA AGCCTCCTGA     7292
ATTAACTATC ATCAGTCCTG CATTTCTTTG GTGGGGGGCC AGGAGGGTGC ATCCAATTTA     7352
ACTTAACTCT TACCTATTTT CTGCAGCTGC TCCCAGATTA CTCCTTCCTT CCAATATAAC     7412
TAGGCAAAAA GAAGTGAGGA GAAACCTGCA TGAAAGCATT CTTCCCTGAA AAGTTAGGCC     7472
TCTCAGAGTC ACCACTTCCT CTGTTGTAGA AAAACTATGT GATGAAACTT TGAAAAAGAT     7532
ATTTATGATG TTAACATTTC AGGTTAAGCC TCATACGTTT AAAATAAAAC TCTCAGTTGT     7592
TTATTATCCT GATCAAGCAT GGAACAAAGC ATGTTTCAGG ATCAGATCAA TACAATCTTG     7652
GAGTCAAAAG GCAAATCATT TGGACAATCT GCAAAATGGA GAGAATACAA TAACTACTAC     7712
AGTAAAGTCT GTTTCTGCTT CCTTACACAT AGATATAATT ATGTTATTTA GTCATTATGA     7772
GGGGCACATT CTTATCTCCA AAACTAGCAT TCTTAAACTG AGAATTATAG ATGGGGTTCA     7832
AGAATCCCTA AGTCCCCTGA AATTATATAA GGCATTCTGT ATAAATGCAA ATGTGCATTT     7892
TTCTGACGAG TGTCCATAGA TATAAAGCCA TTTGGTCTTA ATTCTGACCA ATAAAAAAAT     7952
AAGTCAGGAG GATGCAATTG TTGAAAGCTT TGAAATAAAA TAACAATGTC TTCTTGAAAT     8012
TTGTGATGGC CAAGAAAGAA AATGATGATG ACATTAGGCT TCTAAAGGAC ATACATTTAA     8072
TATTTCTGTG GAAATATGAG GAAAATCCAT GGTTATCTGA GATAGGAGAT ACAAACTTTG     8132
TAATTCTAAT AATGCACTCA GTTTACTCTC TCCCTCTACT AATTTCCTGC TGAAAATAAC     8192
ACAACAAAAA TGTAACAGGG GAAATTATAT ACCGTGACTG AAAACTAGAG TCCTACTTAC     8252
ATAGTTGAAA TATCAAGGAG GTCAGAAGAA AATTGGACTG GTGAAAACAG AAAAAACACT     8312
CCAGTCTGCC ATATCACCAC ACAATAGGAT CCCCCTTCTT GCCCTCCACC CCCATAAGAT     8372
TGTGAAGGGT TTACTGCTCC TTCCATCTGC CTGACCCCTT CACTATGACT ACACAGAATC     8432
TCCTGATAGT AAAGGGGGCT GGAGGCAAGG ATAAGTTATA GAGCAGTTGG AGGAAGCATC     8492
CAAAGATTGC AACCCAGGGC AAATGGAAAA CAGGAGATCC TAATATGAAA GAAAAATGGA     8552
TCCCAATCTG AGAAAAGGCA AAAGAATGGC TACTTTTTTC TATGCTGGAG TATTTTCTAA     8612
TAATCCTGCT TGACCCTTAT CTGACCTCTT TGGAAACTAT AACATAGCTG TCACAGTATA     8672
GTCACAATCC ACAAATGATG CAGGTGCAAA TGGTTTATAG CCCTGTGAAG TTCTTAAAGT     8732
TTAGAGGCTA ACTTACAGAA ATGAATAAGT TGTTTTGTTT TATAGCCCGG TAGAGGAGTT     8792
AACCCCAAAG GTGATATGGT TTTATTTCCT GTTATGTTTA ACTTGATAAT CTTATTTTGG     8852
CATTCTTTTC CCATTGACTA TATACATCTC TATTTCTCAA ATGTTCATGG AACTAGCTCT     8912
TTTATTTTCC TGCTGGTTTC TTCAGTAATG AGTTAAATAA AACATTGACA CATAC          8967
```

( 2 ) INFORMATION FOR SEQ ID NO:2:

( i ) SEQUENCE CHARACTERISTICS:

( A ) LENGTH: 2351 amino acids ( B ) TYPE: amino acid ( D ) TOPOLOGY: linear ( i i ) MOLECULE TYPE: protein ( x i ) SEQUENCE DESCRIPTION: SEQ ID NO:2:

```
Met Gln Ile Glu Leu Ser Thr Cys Phe Phe Leu Cys Leu Leu Arg Phe
  1               5                  10                  15
```

-continued

Cys Phe Ser Ala Thr Arg Arg Tyr Tyr Leu Gly Ala Val Glu Leu Ser
20 25 30

Trp Asp Tyr Met Gln Ser Asp Leu Gly Glu Leu Pro Val Asp Ala Arg
35 40 45

Phe Pro Pro Arg Val Pro Lys Ser Phe Pro Phe Asn Thr Ser Val Val
50 55 60

Tyr Lys Lys Thr Leu Phe Val Glu Phe Thr Asp His Leu Phe Asn Ile
65 70 75 80

Ala Lys Pro Arg Pro Pro Trp Met Gly Leu Leu Gly Pro Thr Ile Gln
85 90 95

Ala Glu Val Tyr Asp Thr Val Val Ile Thr Leu Lys Asn Met Ala Ser
100 105 110

His Pro Val Ser Leu His Ala Val Gly Val Ser Tyr Trp Lys Ala Ser
115 120 125

Glu Gly Ala Glu Tyr Asp Asp Gln Thr Ser Gln Arg Glu Lys Glu Asp
130 135 140

Asp Lys Val Phe Pro Gly Gly Ser His Thr Tyr Val Trp Gln Val Leu
145 150 155 160

Lys Glu Asn Gly Pro Met Ala Ser Asp Pro Leu Cys Leu Thr Tyr Ser
165 170 175

Tyr Leu Ser His Val Asp Leu Val Lys Asp Leu Asn Ser Gly Leu Ile
180 185 190

Gly Ala Leu Leu Val Cys Arg Glu Gly Ser Leu Ala Lys Glu Lys Thr
195 200 205

Gln Thr Leu His Lys Phe Ile Leu Leu Phe Ala Val Phe Asp Glu Gly
210 215 220

Lys Ser Trp His Ser Glu Thr Lys Asn Ser Leu Met Gln Asp Arg Asp
225 230 235 240

Ala Ala Ser Ala Arg Ala Trp Pro Lys Met His Thr Val Asn Gly Tyr
245 250 255

Val Asn Arg Ser Leu Pro Gly Leu Ile Gly Cys His Arg Lys Ser Val
260 265 270

Tyr Trp His Val Ile Gly Met Gly Thr Thr Pro Glu Val His Ser Ile
275 280 285

Phe Leu Glu Gly His Thr Phe Leu Val Arg Asn His Arg Gln Ala Ser
290 295 300

Leu Glu Ile Ser Pro Ile Thr Phe Leu Thr Ala Gln Thr Leu Leu Met
305 310 315 320

Asp Leu Gly Gln Phe Leu Leu Phe Cys His Ile Ser Ser His Gln His
325 330 335

Asp Gly Met Glu Ala Tyr Val Lys Val Asp Ser Cys Pro Glu Glu Pro
340 345 350

Gln Leu Arg Met Lys Asn Asn Glu Glu Ala Glu Asp Tyr Asp Asp Asp
355 360 365

Leu Thr Asp Ser Glu Met Asp Val Val Arg Phe Asp Asp Asp Asn Ser
370 375 380

Pro Ser Phe Ile Gln Ile Arg Ser Val Ala Lys Lys His Pro Lys Thr
385 390 395 400

Trp Val His Tyr Ile Ala Ala Glu Glu Glu Asp Trp Asp Tyr Ala Pro
405 410 415

Leu Val Leu Ala Pro Asp Asp Arg Ser Tyr Lys Ser Gln Tyr Leu Asn
420 425 430

Asn Gly Pro Gln Arg Ile Gly Arg Lys Tyr Lys Lys Val Arg Phe Met
435 440 445

-continued

Ala Tyr Thr Asp Glu Thr Phe Lys Thr Arg Glu Ala Ile Gln His Glu
450 455 460

Ser Gly Ile Leu Gly Pro Leu Leu Tyr Gly Glu Val Gly Asp Thr Leu
465 470 475 480

Leu Ile Ile Phe Lys Asn Gln Ala Ser Arg Pro Tyr Asn Ile Tyr Pro
485 490 495

His Gly Ile Thr Asp Val Arg Pro Leu Tyr Ser Arg Arg Leu Pro Lys
500 505 510

Gly Val Lys His Leu Lys Asp Phe Pro Ile Leu Pro Gly Glu Ile Phe
515 520 525

Lys Tyr Lys Trp Thr Val Thr Val Glu Asp Gly Pro Thr Lys Ser Asp
530 535 540

Pro Arg Cys Leu Thr Arg Tyr Tyr Ser Ser Phe Val Asn Met Glu Arg
545 550 555 560

Asp Leu Ala Ser Gly Leu Ile Gly Pro Leu Leu Ile Cys Tyr Lys Glu
565 570 575

Ser Val Asp Gln Arg Gly Asn Gln Ile Met Ser Asp Lys Arg Asn Val
580 585 590

Ile Leu Phe Ser Val Phe Asp Glu Asn Arg Ser Trp Tyr Leu Thr Glu
595 600 605

Asn Ile Gln Arg Phe Leu Pro Asn Pro Ala Gly Val Gln Leu Glu Asp
610 615 620

Pro Glu Phe Gln Ala Ser Asn Ile Met His Ser Ile Asn Gly Tyr Val
625 630 635 640

Phe Asp Ser Leu Gln Leu Ser Val Cys Leu His Glu Val Ala Tyr Trp
645 650 655

Tyr Ile Leu Ser Ile Gly Ala Gln Thr Asp Phe Leu Ser Val Phe Phe
660 665 670

Ser Gly Tyr Thr Phe Lys His Lys Met Val Tyr Glu Asp Thr Leu Thr
675 680 685

Leu Phe Pro Phe Ser Gly Glu Thr Val Phe Met Ser Met Glu Asn Pro
690 695 700

Gly Leu Trp Ile Leu Gly Cys His Asn Ser Asp Phe Arg Asn Arg Gly
705 710 715 720

Met Thr Ala Leu Leu Lys Val Ser Ser Cys Asp Lys Asn Thr Gly Asp
725 730 735

Tyr Tyr Glu Asp Ser Tyr Glu Asp Ile Ser Ala Tyr Leu Leu Ser Lys
740 745 750

Asn Asn Ala Ile Glu Pro Arg Ser Phe Ser Gln Asn Ser Arg His Arg
755 760 765

Ser Thr Arg Gln Lys Gln Phe Asn Ala Thr Thr Ile Pro Glu Asn Asp
770 775 780

Ile Glu Lys Thr Asp Pro Trp Phe Ala His Arg Thr Pro Met Pro Lys
785 790 795 800

Ile Gln Asn Val Ser Ser Ser Asp Leu Leu Met Leu Leu Arg Gln Ser
805 810 815

Pro Thr Pro His Gly Leu Ser Leu Ser Asp Leu Gln Glu Ala Lys Tyr
820 825 830

Glu Thr Phe Ser Asp Asp Pro Ser Pro Gly Ala Ile Asp Ser Asn Asn
835 840 845

Ser Leu Ser Glu Met Thr His Phe Arg Pro Gln Leu His His Ser Gly
850 855 860

Asp Met Val Phe Thr Pro Glu Ser Gly Leu Gln Leu Arg Leu Asn Glu

-continued 865 870 875 880

Lys Leu Gly Thr Thr Ala Ala Thr Glu Leu Lys Lys Leu Asp Phe Lys
885 890 895

Val Ser Ser Thr Ser Asn Asn Leu Ile Ser Thr Ile Pro Ser Asp Asn
900 905 910

Leu Ala Ala Gly Thr Asp Asn Thr Ser Ser Leu Gly Pro Pro Ser Met
915 920 925

Pro Val His Tyr Asp Ser Gln Leu Asp Thr Thr Leu Phe Gly Lys Lys
930 935 940

Ser Ser Pro Leu Thr Glu Ser Gly Gly Pro Leu Ser Leu Ser Glu Glu
945 950 955 960

Asn Asn Asp Ser Lys Leu Leu Glu Ser Gly Leu Met Asn Ser Gln Glu
965 970 975

Ser Ser Trp Gly Lys Asn Val Ser Ser Thr Glu Ser Gly Arg Leu Phe
980 985 990

Lys Gly Lys Arg Ala His Gly Pro Ala Leu Leu Thr Lys Asp Asn Ala
995 1000 1005

Leu Phe Lys Val Ser Ile Ser Leu Leu Lys Thr Asn Lys Thr Ser Asn
1010 1015 1020

Asn Ser Ala Thr Asn Arg Lys Thr His Ile Asp Gly Pro Ser Leu Leu
1025 1030 1035 1040

Ile Glu Asn Ser Pro Ser Val Trp Gln Asn Ile Leu Glu Ser Asp Thr
1045 1050 1055

Glu Phe Lys Lys Val Thr Pro Leu Ile His Asp Arg Met Leu Met Asp
1060 1065 1070

Lys Asn Ala Thr Ala Leu Arg Leu Asn His Met Ser Asn Lys Thr Thr
1075 1080 1085

Ser Ser Lys Asn Met Glu Met Val Gln Gln Lys Lys Glu Gly Pro Ile
1090 1095 1100

Pro Pro Asp Ala Gln Asn Pro Asp Met Ser Phe Phe Lys Met Leu Phe
1105 1110 1115 1120

Leu Pro Glu Ser Ala Arg Trp Ile Gln Arg Thr His Gly Lys Asn Ser
1125 1130 1135

Leu Asn Ser Gly Gln Gly Pro Ser Pro Lys Gln Leu Val Ser Leu Gly
1140 1145 1150

Pro Glu Lys Ser Val Glu Gly Gln Asn Phe Leu Ser Glu Lys Asn Lys
1155 1160 1165

Val Val Val Gly Lys Gly Glu Phe Thr Lys Asp Val Gly Leu Lys Glu
1170 1175 1180

Met Val Phe Pro Ser Ser Arg Asn Leu Phe Leu Thr Asn Leu Asp Asn
1185 1190 1195 1200

Leu His Glu Asn Asn Thr His Asn Gln Glu Lys Lys Ile Gln Glu Glu
1205 1210 1215

Ile Glu Lys Lys Glu Thr Leu Ile Gln Glu Asn Val Val Leu Pro Gln
1220 1225 1230

Ile His Thr Val Thr Gly Thr Lys Asn Phe Met Lys Asn Leu Phe Leu
1235 1240 1245

Leu Ser Thr Arg Gln Asn Val Glu Gly Ser Tyr Asp Gly Ala Tyr Ala
1250 1255 1260

Pro Val Leu Gln Asp Phe Arg Ser Leu Asn Asp Ser Thr Asn Arg Thr
1265 1270 1275 1280

Lys Lys His Thr Ala His Phe Ser Lys Lys Gly Glu Glu Glu Asn Leu
1285 1290 1295

-continued

Glu Gly Leu Gly Asn Gln Thr Lys Gln Ile Val Glu Lys Tyr Ala Cys
1300 1305 1310

Thr Thr Arg Ile Ser Pro Asn Thr Ser Gln Gln Asn Phe Val Thr Gln
1315 1320 1325

Arg Ser Lys Arg Ala Leu Lys Gln Phe Arg Leu Pro Leu Glu Glu Thr
1330 1335 1340

Glu Leu Glu Lys Arg Ile Ile Val Asp Asp Thr Ser Thr Gln Trp Ser
1345 1350 1355 1360

Lys Asn Met Lys His Leu Thr Pro Ser Thr Leu Thr Gln Ile Asp Tyr
1365 1370 1375

Asn Glu Lys Glu Lys Gly Ala Ile Thr Gln Ser Pro Leu Ser Asp Cys
1380 1385 1390

Leu Thr Arg Ser His Ser Ile Pro Gln Ala Asn Arg Ser Pro Leu Pro
1395 1400 1405

Ile Ala Lys Val Ser Ser Phe Pro Ser Ile Arg Pro Ile Tyr Leu Thr
1410 1415 1420

Arg Val Leu Phe Gln Asp Asn Ser Ser His Leu Pro Ala Ala Ser Tyr
1425 1430 1435 1440

Arg Lys Lys Asp Ser Gly Val Gln Glu Ser Ser His Phe Leu Gln Gly
1445 1450 1455

Ala Lys Lys Asn Asn Leu Ser Leu Ala Ile Leu Thr Leu Glu Met Thr
1460 1465 1470

Gly Asp Gln Arg Glu Val Gly Ser Leu Gly Thr Ser Ala Thr Asn Ser
1475 1480 1485

Val Thr Tyr Lys Lys Val Glu Asn Thr Val Leu Pro Lys Pro Asp Leu
1490 1495 1500

Pro Lys Thr Ser Gly Lys Val Glu Leu Leu Pro Lys Val His Ile Tyr
1505 1510 1515 1520

Gln Lys Asp Leu Phe Pro Thr Glu Thr Ser Asn Gly Ser Pro Gly His
1525 1530 1535

Leu Asp Leu Val Glu Gly Ser Leu Leu Gln Gly Thr Glu Gly Ala Ile
1540 1545 1550

Lys Trp Asn Glu Ala Asn Arg Pro Gly Lys Val Pro Phe Leu Arg Val
1555 1560 1565

Ala Thr Glu Ser Ser Ala Lys Thr Pro Ser Lys Leu Leu Asp Pro Leu
1570 1575 1580

Ala Trp Asp Asn His Tyr Gly Thr Gln Ile Pro Lys Glu Glu Trp Lys
1585 1590 1595 1600

Ser Gln Glu Lys Ser Pro Glu Lys Thr Ala Phe Lys Lys Lys Asp Thr
1605 1610 1615

Ile Leu Ser Leu Asn Ala Cys Glu Ser Asn His Ala Ile Ala Ala Ile
1620 1625 1630

Asn Glu Gly Gln Asn Lys Pro Glu Ile Glu Val Thr Trp Ala Lys Gln
1635 1640 1645

Gly Arg Thr Glu Arg Leu Cys Ser Gln Asn Pro Pro Val Leu Lys Arg
1650 1655 1660

His Gln Arg Glu Ile Thr Arg Thr Thr Leu Gln Ser Asp Gln Glu Glu
1665 1670 1675 1680

Ile Asp Tyr Asp Asp Thr Ile Ser Val Glu Met Lys Lys Glu Asp Phe
1685 1690 1695

Asp Ile Tyr Asp Glu Asp Glu Asn Gln Ser Pro Arg Ser Phe Gln Lys
1700 1705 1710

Lys Thr Arg His Tyr Phe Ile Ala Ala Val Glu Arg Leu Trp Asp Tyr
1715 1720 1725

-continued

Gly Met Ser Ser Ser Pro His Val Leu Arg Asn Arg Ala Gln Ser Gly
1730 1735 1740

Ser Val Pro Gln Phe Lys Lys Val Val Phe Gln Glu Phe Thr Asp Gly
1745 1750 1755 1760

Ser Phe Thr Gln Pro Leu Tyr Arg Gly Glu Leu Asn Glu His Leu Gly
1765 1770 1775

Leu Leu Gly Pro Tyr Ile Arg Ala Glu Val Glu Asp Asn Ile Met Val
1780 1785 1790

Thr Phe Arg Asn Gln Ala Ser Arg Pro Tyr Ser Phe Tyr Ser Ser Leu
1795 1800 1805

Ile Ser Tyr Glu Glu Asp Gln Arg Gln Gly Ala Glu Pro Arg Lys Asn
1810 1815 1820

Phe Val Lys Pro Asn Glu Thr Lys Thr Tyr Phe Trp Lys Val Gln His
1825 1830 1835 1840

His Met Ala Pro Thr Lys Asp Glu Phe Asp Cys Lys Ala Trp Ala Tyr
1845 1850 1855

Phe Ser Asp Val Asp Leu Glu Lys Asp Val His Ser Gly Leu Ile Gly
1860 1865 1870

Pro Leu Leu Val Cys His Thr Asn Thr Leu Asn Pro Ala His Gly Arg
1875 1880 1885

Gln Val Thr Val Gln Glu Phe Ala Leu Phe Phe Thr Ile Phe Asp Glu
1890 1895 1900

Thr Lys Ser Trp Tyr Phe Thr Glu Asn Met Glu Arg Asn Cys Arg Ala
1905 1910 1915 1920

Pro Cys Asn Ile Gln Met Glu Asp Pro Thr Phe Lys Glu Asn Tyr Arg
1925 1930 1935

Phe His Ala Ile Asn Gly Tyr Ile Met Asp Thr Leu Pro Gly Leu Val
1940 1945 1950

Met Ala Gln Asp Gln Arg Ile Arg Trp Tyr Leu Leu Ser Met Gly Ser
1955 1960 1965

Asn Glu Asn Ile His Ser Ile His Phe Ser Gly His Val Phe Thr Val
1970 1975 1980

Arg Lys Lys Glu Glu Tyr Lys Met Ala Leu Tyr Asn Leu Tyr Pro Gly
1985 1990 1995 2000

Val Phe Glu Thr Val Glu Met Leu Pro Ser Lys Ala Gly Ile Trp Arg
2005 2010 2015

Val Glu Cys Leu Ile Gly Glu His Leu His Ala Gly Met Ser Thr Leu
2020 2025 2030

Phe Leu Val Tyr Ser Asn Lys Cys Gln Thr Pro Leu Gly Met Ala Ser
2035 2040 2045

Gly His Ile Arg Asp Phe Gln Ile Thr Ala Ser Gly Gln Tyr Gly Gln
2050 2055 2060

Trp Ala Pro Lys Leu Ala Arg Leu His Tyr Ser Gly Ser Ile Asn Ala
2065 2070 2075 2080

Trp Ser Thr Lys Glu Pro Phe Ser Trp Ile Lys Val Asp Leu Leu Ala
2085 2090 2095

Pro Met Ile Ile His Gly Ile Lys Thr Gln Gly Ala Arg Gln Lys Phe
2100 2105 2110

Ser Ser Leu Tyr Ile Ser Gln Phe Ile Ile Met Tyr Ser Leu Asp Gly
2115 2120 2125

Lys Lys Trp Gln Thr Tyr Arg Gly Asn Ser Thr Gly Thr Leu Met Val
2130 2135 2140

Phe Phe Gly Asn Val Asp Ser Ser Gly Ile Lys His Asn Ile Phe Asn

-continued 2145 2150 2155 2160

Pro Pro Ile Ile Ala Arg Tyr Ile Arg Leu His Pro Thr His Tyr Ser
2165 2170 2175

Ile Arg Ser Thr Leu Arg Met Glu Leu Met Gly Cys Asp Leu Asn Ser
2180 2185 2190

Cys Ser Met Pro Leu Gly Met Glu Ser Lys Ala Ile Ser Asp Ala Gln
2195 2200 2205

Ile Thr Ala Ser Ser Tyr Phe Thr Asn Met Phe Ala Thr Trp Ser Pro
2210 2215 2220

Ser Lys Ala Arg Leu His Leu Gln Gly Arg Ser Asn Ala Trp Arg Pro
2225 2230 2235 2240

Gln Val Asn Asn Pro Lys Glu Trp Leu Gln Val Asp Phe Gln Lys Thr
2245 2250 2255

Met Lys Val Thr Gly Val Thr Thr Gln Gly Val Lys Ser Leu Leu Thr
2260 2265 2270

Ser Met Tyr Val Lys Glu Phe Leu Ile Ser Ser Ser Gln Asp Gly His
2275 2280 2285

Gln Trp Thr Leu Phe Phe Gln Asn Gly Lys Val Lys Val Phe Gln Gly
2290 2295 2300

Asn Gln Asp Ser Phe Thr Pro Val Val Asn Ser Leu Asp Pro Pro Leu
2305 2310 2315 2320

Leu Thr Arg Tyr Leu Arg Ile His Pro Gln Ser Trp Val His Gln Ile
2325 2330 2335

Ala Leu Arg Met Glu Val Leu Gly Cys Glu Ala Gln Asp Leu Tyr
2340 2345 2350

( 2 ) INFORMATION FOR SEQ ID NO:3:

( i ) SEQUENCE CHARACTERISTICS:
( A ) LENGTH: 233 base pairs
( B ) TYPE: nucleic acid
( C ) STRANDEDNESS: single
( D ) TOPOLOGY: linear ( i i ) MOLECULE TYPE: cDNA ( x i ) SEQUENCE DESCRIPTION: SEQ ID NO:3:

GCGGCCGGGA ACGGTGCATT GGAACGCGGA TTCCCCGTGC 40

CAAGAGTGAC GTAAGTACCG CCTATAGAGT CTATAGGCCC 80

ACCCCCTTGG CTTCTTATGC GACGGATCCC GTACTAAGCT 120

TGAGGTGTGG CAGGCTTGAG ATCTGGCCAT ACACTTGAGT 160

GACAATGACA TCCACTTTGC CTTTCTCTCC ACAGGTGTCC 200

ACTCCCAGGT CCAACTGCAG CTCGGTTCTA TCG 233

RETROVIRAL DELIVERY OF FULL LENGTH FACTOR VIII

TECHNICAL FIELD OF THE INVENTION

The present invention relates to retroviral-mediated gene therapy. Specifically, the invention relates to recombinant retroviral vectors capable of delivering nucleic acid constructs encoding full length factor VIII to a patient, pharmaceutical compositions comprising such retroviral vectors, and methods of making and using the same.

BACKGROUND OF THE INVENTION

Numerous methods exist for genetically engineering vertebrate cells. Of particular interest are those methods that may be used to engineer mammalian cells, so as to enable the production of large quantities of various polypeptides (such as erythropoietin and factor VIII), as well as to treat various diseases, for instance serious vital infections, cancers, and genetic diseases. One method for successfully introducing nucleic acid molecules into cells involves the use of viral vectors, with vectors derived from retroviruses being prototypic examples.

Retroviruses are RNA viruses, meaning their genomes comprise RNA. Upon infection of a replicating cell, the retroviral genome is reverse transcribed into DNA, which is then made double stranded. The double-stranded DNA copy then stably integrates into a chromosome of the infected cell, forming a "provirus" which is inherited by daughter cells as is any other gene.

Wild-type retroviral genomes (and their proviral copies) typically contain three genes, the gag, pol, and env genes, preceded by a packaging signal ((ϕ), and two long terminal repeat (LTR) sequences which flank either end (see FIG. 1). The gag gene encodes the internal structural (nucleocapsid) proteins. Pol codes for the RNA-dependent DNA polymerase which reverse transcribes the RNA genome, while env encodes the retroviral envelope glycoproteins. The 5' and 3' LTRs contain the cis-acting elements necessary to promote transcription and polyadenylation of retrovital RNA.

Adjacent to the 5' LTR are sequences necessary for reverse transcription of the genome (the tRNA primer binding site) and for efficient encapsidation of retroviral RNA into particles (the ϕ sequence). Removal of the packaging signal prevents encapsidation (packaging of retroviral RNA into infectious virions) of genomic RNA, although the resulting mutant can still direct synthesis of all proteins encoded in the viral genome.

Retroviral vectors (genetically manipulated forms of naturally occurring retroviruses) have a number of important properties, including: (1)efficient entry of genetic material (the vector genome) into cells; (2) an active, efficient process of entry into the target cell nucleus; (3) relatively high levels of gene expression; and (4) the potential to target to particular cellular subtypes through control of the vector-target cell binding and the tissue-specific control of gene expression. For example, a foreign gene of interest may be incorporated into the retrovirus in place of the normal retrovital RNA. When the retrovirus injects its RNA into a cell, the foreign gene is also introduced into the cell, and may then be integrated into the host's cellular DNA as if it were the retrovirus itself. Expression of this foreign gene within the host results in expression of the foreign protein by the host cell.

Retroviral vectors and various uses thereof have been described in numerous applications, including Mann, et al. (*Cell* 33: 153, 1983), Cane and Mulligan (*Proc. Nat'l. Acad. Sci. USA* 81:6349, 1984), Warner, et al. (1991), *AIDS Res. Hum. Retroviruses*, vol. 7, p.645, Jolly, et al. (1986), *Mol. Cell. Bio.*, vol. 6, p.1141, U.S. Ser. No. 08/136,739, filed Oct. 12, 1993, WO 93/10814, WO 93/15207, and U.S. Ser. No. 08/155,994, filed Nov. 18, 1993. The ability of retroviral vectors to integrate into the genome of replicating vertebrate cells have made them useful for gene therapy purposes (Miller, et al. *Methods in Enzymology* 217:581, 1993). Typically, gene therapy involves adding new or additional genetic material to (1) patient cells in vivo or (2) patient cells that have been removed and which, following transduction, are either reintroduced immediately to the patient or expanded ex vivo prior to reintroduction.

Hemophilia is a genetic disease characterized by a severe blood clotting deficiency. As such, it will be amenable to treatment by gene therapy. In hemophilia A, an X-chromosome linked genetic defect disrupts the gene encoding factor VIII, a trace plasma glycoprotein which acts as a cofactor in conjunction with factor IXa in the activation of factor X. In humans, the factor VIII gene codes for 2,351 amino acids. The protein has six domains, designated from amino to carboxy terminus as A1, A2, B, A3, C1, and C2, respectively (Wood, et al., *Nature* 312:330, 1984: Vehar, et al., *Nature* 312:337, 1984; and Toole, et al., *Nature* 312:342, 1984), with a deduced molecular weight of about 280 kilo Daltons (kD). The 980 amino acid B domain is deleted in the activated procoagulant form of the protein. Additionally, in the native protein two polypeptide chains, a and b, flanking the B domain, are bound to a divalent calcium cation.

The genetic defect causing hemophilia A affects about one in every 10,000 males. Due to the resultant clotting deficiency, those afflicted with the disease suffer severe bleeding episodes due to small injuries, internal bleeding, and joint hemorrhage, which leads to arthropathy, the major cause of morbidity in hemophilia. Normal levels of factor VIII average between 50 to 200 ng/mL of blood plasma (Mannucci, P. M. in *Practical Laboratory Hematology*, ed. Koepke, J. A., Churchill Livingstone, N. Y., pp:347–371, 1990); however, patients suffering from mild to moderate hemophilia A typically have plasma levels well below 2–60 ng/mL, while levels below about 2 ng/mL result in severe hemophilia.

Previously, therapy for hemophilia A involved repeated administration of human factor VIII purified from blood products pooled in lots from over 1000 donors. However, because of the instability of the factor VIII protein, resulting pharmaceutical products using the natural protein typically were highly impure, with an estimated purity by weight (factor VIII to total protein) of approximately 0.04%. Due to the frequency of administration and inability to remove various human pathogens from such preparations, more than 90% of those suffering from hemophilia A were infected in the 1980s with the human immunodeficiency virus (HIV) as a result of their therapy. Many of these HIV infected patients and other HIV negative hemophiliacs have also been infected by Hepatitis B in the same way. Fortunately, recent advances in genetic engineering have lead to the commercial availability of a recombinant form of the protein free from contamination with human pathogens. However, this form of therapy is expensive and chronic. In addition, most hemophilia A patients in the Unites States do not presently receive factor VIII maintenance therapy, but instead only receive the polypeptide prior to activities or events which might cause bleeding, such as surgery, or to treat spontaneous bleeding. Interestingly, this is despite evidence showing that hemophilic arthropathy can be prevented by administering from an early age prophylactic amounts of factor VIII, typically 24–40 IU per kilogram bodyweight, three times a week. Such therapy kept factor VIII concentrations from falling below 1% of normal (Nillson, et al., *J. Internal Med.* 232:23, 1992). For these reasons, a genetic therapy affording continuous, long term therapeutically effective expression levels or amounts of factor VIII, i.e., to decrease the severity of or eliminate the clotting disorder associated with hemophilia A, would be of great benefit.

However, full length factor VIII is encoded by a gene whose cDNA is about 8,800 base pairs (bp) in length (Zatloukal, et al., *Proc. Nat'l. Acad. Sci. USA* 91:5148, 1994). As retroviral genomes generally contain fewer than 10,000 nucleotides, packaging efficiency falls dramatically when more than about 10,000 nucleotides are present. In most situations, this is not a problem because retroviral vectors comprising a gene of interest (encoding the desired product) generally do not exceed 10 kb. However, because the factor VIII cDNA is much larger than the typical mammalian cDNA, it was considered unlikely that the full length cDNA could be included in a retroviral vector capable of efficient incorporation into an infectious virion, be transmitted to a target cell, and be expressed therein. As a result, to date successful attempts to incorporate a factor VIII cDNA into a retroviral vector have involved deleted forms of the gene, such as that disclosed by Zatloukal, et al, supra. Such deletions may result in nuclear transcripts which differ from those derived from a full length factor VIII cDNA. As a result, the foreshortened RNA may be processed and transported differently, as might the resultant protein. Indeed, Toole, et al. (*Proc. Nat'l. Acad. Sci. USA,* 83:5939, 1986) reported that the B domain deleted protein is more easily processed in transduced cells than the full length protein. Hoeben, et al. (*Thrombosis and Haeraostasis,* 67(3) :341, 1992) reported that when retroviral vectors harboring a factor VIII coding region lacking almost all of the B-domain and a neomycin resistence gene were employed to transduce isolated murine bone marrow cells, in vivo factor VIII expression, at either the mRNA or protein level, could not be detected in progenitor cell-derived cells, despite initial transcription immediately after transduction of the progenitors. However, Southern analysis revealed drug resistant cells contained the vector.

It is an object of the present invention to provide recombinant retrovital vectors comprising a full length factor VIII cDNA which may be efficiently packaged into infectious retrovital particles. Such retroviral particles may be used to transduce cells either in vivo or ex vivo. Factor VIII expressed from such transduced cells will be processed and transported in a fashion analogous to the expression product of a normally functioning factor VIII gene. As such, retroviral particles harboring such vectors will be useful in the treatment of hemophilia A.

SUMMARY OF THE INVENTION

Briefly stated, the present invention provides retroviral vectors directing the expression of a full length factor VIII polypeptide, retroviral particles comprising such vectors, as well as methods of making and using the same. In one aspect of the present invention, retroviral vectors directing the expression of a full length factor VIII polypeptide in transfected host cells are provided. In various embodiments of this aspect of the invention, the retroviral vector is derived from a retrovirus selected from the group consisting of MoMLV, GALV, FeLV, and FIV.

Another embodiment concerns retroviral vectors wherein the full length factor VIII polypeptide is encoded by a nucleic acid molecule having a nucleotide sequence selected from the group consisting of the nucleotide sequence set forth in SEQ ID NO: 1, except that a uracil ("U") replaces every thymidine ("T"), a nucleotide sequence which hybridizes under stringent conditions to the nucleotide sequence set forth in SEQ ID NO: 1, and nucleotide sequences which, but for the degeneracy of the genetic code, would hybridize to such nucleotide sequences.

In another embodiment, such retroviral vectors comprise a promoter selected from the group consisting of a retroviral LTR promoter, a SV40 promoter, a CMV MIE promoter, and a MPMV promoter, wherein the promoter is operably associated with the nucleic acid molecule encoding a full length factor VIII polypeptide. In preferred embodiments, the retroviral vector comprises a retroviral backbone derived from MoMLV encoding a full length factor VIII polypeptide, wherein the full length factor VIII polypeptide is encoded by a nucleic acid molecule having a nucleotide sequence selected from the group consisting of the nucleotide sequence set forth in SEQ ID NO: 1, except that a uracil ("U") replaces every thymidine ("T"); a nucleotide sequence which hybridizes under stringent conditions to such a nucleotide sequence; and nucleotide sequences which, but for the degeneracy of the genetic code, would hybridize to the foregoing sequences.

Another aspect of the invention relates to host cells transfected or transduced by a retroviral vector directing the expression of a full length factor VIII polypeptide. In one embodiment, such host cells are transfected or transduced by a retroviral vector comprising a retroviral backbone derived from MoMLV encoding a full length factor VIII polypeptide, wherein the full length factor VIII polypeptide is encoded by a nucleic acid molecule having a nucleotide sequence selected from the group consisting of a nucleotide sequence set forth in SEQ ID NO: 1, except that a uracil ("U") replaces every thymidine ("T"); a nucleotide sequence which hybridizes under stringent conditions to such a nucleotide sequence; and nucleotide sequences which, but for the degeneracy of the genetic code, would hybridize to any of the the foregoing sequences. In one such embodiment of this aspect of the invention, host cells are packaging cells and further comprise one or more nucleic acid molecules encoding retroviral structural polypeptides. Especially preferred are packaging cells wherein the retroviral structural polypeptides comprise env, pol, and gag polypeptides.

In yet another aspect of the invention, retroviral particles comprising retroviral vectors capable of directing expression of a full length factor VIII polypeptide are also provided herein. Various embodiments of this aspect of the invention provide for retroviral particles that are either amphotropic, ecotropic, polytropic, or xenotropic retroviral particles. In another embodiment, such retroviral particles are resistant to inactivation by a mammalian complement system, particularly a human complement system.

Still another aspect of the invention concerns methods of making such retroviral particles comprising transducing and transfecting a packaging cell with a nucleic acid molecule encoding a retroviral vector for directing the expression of full length factor VIII and cultivating a packaging cell under appropriate conditions such that copies of the retroviral vector are produced and incorporated into infectious retroviral particles.

In yet another aspect of the invention, pharmaceutical compositions comprising retroviral particles comprising retroviral vectors capable of directing the expression of a full length factor VIII polypeptide in host cells transduced or transfected with the retroviral vectors are provided. In one embodiment, such compositions are lyophilized. In another embodiment, the pharmaceutical compositions comprise retroviral particles according to the invention and a pharmaceutically acceptable diluent. In yet a further aspect of the invention, methods are provided for treating mammals afflicted with hemophilia wherein the mammals are administered a therapeutically effective amount of a retroviral vector produced in accordance with the invention. In the preferred embodiment of this aspect of the invention, the mammal being treated is human and is afflicted with hemophilia A. In another preferred embodiment, a human afflicted with hemophilia A is treated by administering to the patient a therapeutically effective amount of a retroviral particle, preferably in a pharmaceutical composition comprising the retroviral particle in a pharmaceutically acceptable diluent.

Another embodiment of this invention concerns retroviral particles comprising a nucleic acid molecule encoding a full length factor VIII polypeptide wherein the full length factor VIII polypeptide comprises an amino acid sequence selected from the group consisting of canine, feline, bovine, monkey, murine, ovine, avian, equine, porcine, rabbit, rat, and human full length factor VIII.

In yet another aspect of the invention, plasmids comprising a nucleic acid molecule encoding a retroviral vector for directing the expression of a full length factor VIII polypeptide in host cells transduced or transfected with such plasmids are provided.

Yet another aspect of the invention relates to methods for in vivo production of a full length factor VIII polypeptide wherein retroviral vectors capable of directing the expression of a therapeutically effective amount of a full length factor VIII polypeptide are delivered to the cells of a patient. In a preferred embodiment of this aspect, the retroviral vector is delivered to cells by a retroviral particle comprising the retrovital vector. In a preferred embodiment, the retroviral particle targets the delivery of the retroviral vector to specific subsets of cells in the patient. Especially preferred subsets of cells include hematopoietic cells, endothelial cells, liver cells, and combinations thereof. Preferred hematopoietic cells are stem cells from bone marrow or umbilical cord blood. Such methods involve either ex vivo or in vivo delivery of retroviral vectors to the cells. Particularly preferred methods of in vivo delivery of the retroviral vectors according to the invention include parenteral administration and pulmonary administration. In a particularly preferred embodiment of this aspect of the invention, the in vivo production of full length factor VIII results from stable expression of the full length factor VIII polypeptide from a proviral from of the retroviral vector.

Another aspect of the invention involves host cells that stably express full length factor VIII following transduction with a retroviral vector capable of directing the expression of a full length factor VIII polypeptide. In a preferred embodiment, such host cells are of human origin.

These and other aspects and embodiments of the invention will become evident upon reference to the following detailed description and attached figures.

BRIEF DESCRIPTION OF THE FIGURES

FIG. 2 illustrates the human coagulation pathway.

DEFINITION OF TERMS

Figure 1:
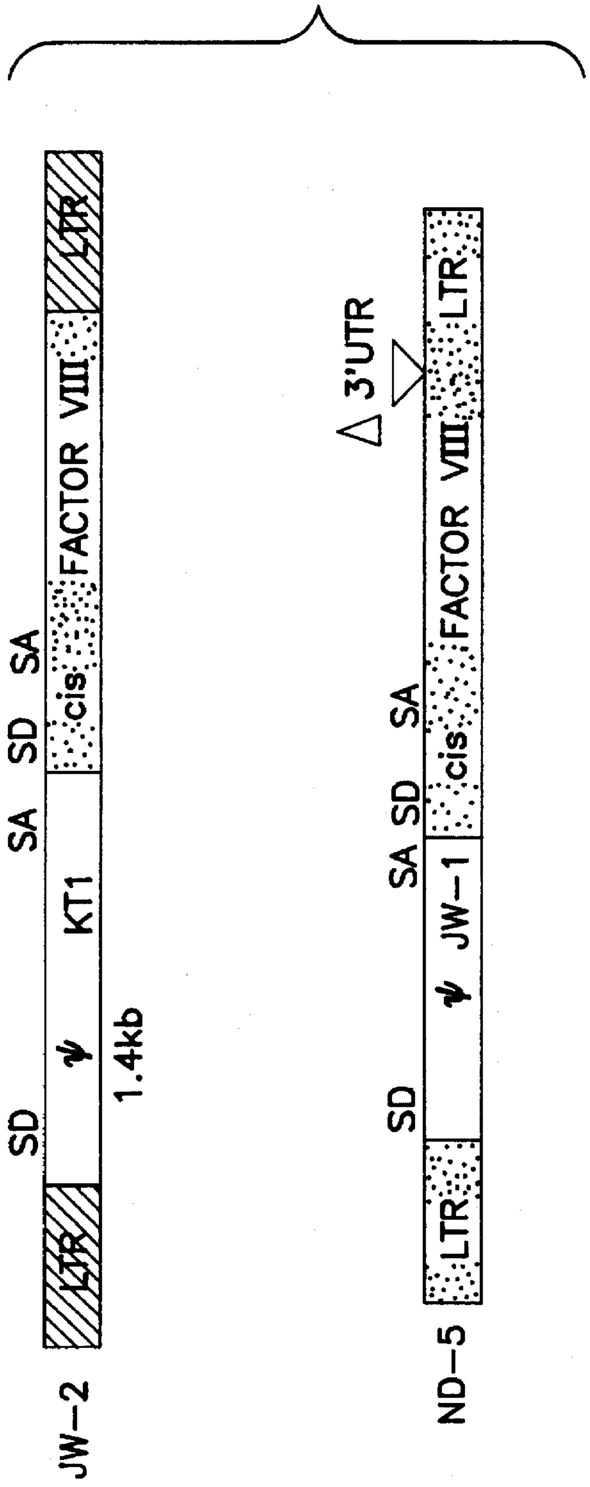
FIG. 1 is a graphic representation of two retroviral vectors, JW-2 and ND-5, encoding full length factor VIII.

The following terms are used throughout the specification. Unless otherwise indicated, these terms are defined as follows:

"Factor VIII" is a nonenzymatic cofactor found in blood in an inactive precursor form. Precursor factor VIII is converted to the active cofactor, factor VIIIa, through limited proteolysis at specific sites by plasma proteases, notably thrombin and factor IX*a*. The majority of factor VIII circulates as a two-chain heterodimer most likely due to intracellular or pericellular processing of the single chain gene product. The two chains are noncovalently associated in a metal ion dependent manner.

The "biological activity" of factor VIII refers to a function or set of functions performed by the polypeptide or fragments thereof in a biological system or in an in vitro facsimile thereof. In general, biological activities can include effector and cofactor activities. Effector activities include binding of factor VIII or its fragments to other proteins or cells. Effector activity may enhance or be required for cofactor activity. Cofactor activities include enhancement of activation of factor X by factor IXa ("tenase"), and possibly the enhancement of inactivation of factors Va or VIIIa by activated protein C. The biological activity of factor VIIIa may be characterized by its ability to form a membrane binding site for factors IXa and X in a conformation suitable for activation of the latter by the former, and possibly by the ability of the B domain of precursor factor VIII to act synergistically with protein S to enhance inactivation of factors Va or VIIIa by activated protein C. This would include standard assays of factor IX or X activation, binding to phospholipids, von Willebrand factor, or specific cell surface molecules, and susceptibility to thrombin, factor IXa, activated protein C, or other specific proteases under appropriate conditions, and correcting the coagulation defect in plasma derived from individuals afflicted with hemophilia A or the prothrombotice defect in individuals allicted with activated proteinase C resistance.

A "factor VIII cDNA molecule" is one encoding a full length factor VIII polypeptide. The human full length factor VIII coding region is 7,056 nucleotides.

A "full length factor VIII" polypeptide refers to a protein comprising at least 95% of the amino acid sequence, or 2215 amino acids, shown in SEQ ID NO: 1. Also included within this definition are various factor VIII analogues or modified forms comprising at least 95% of the amino acid sequence, or 2215 amino acids, of full length factor VIII, wherein one or more amino acids have been substituted, deleted, or inserted, as is discussed in more detail below. Any such analogue will have at least one of the recognized biological activities of factor VIII. Nucleic acids encoding full length factor VIII refer to those encoding a full length factor VIII polypeptide.

"Persistent" transduction refers to the introduction of the desired heterologous gene into a cell together with genetic elements which enable episomal (extrachromosomal) replication. This can lead to apparently stable transformation without integration of the vector, or proviral form of the vector, into the chromosome of the host or recipient cell. "Stable" transformation refers to the introduction of the desired heterologous gene into the chromosome of the infected or transduced cell. At least the gene, and potentially most or all of entire vector, integrates and becomes a permanent component of the genome of that cell. In contrast, "transient" refers to the situation where the introduced genetic material is not integrated into the host cell's genome or replicated and is accordingly not heritably passed on during cell division.

"Stringent conditions" are those nucleic acid hybridization conditions which promote the annealing and stabilization of nucleic acid molecules having complementary nucleotide sequences but which retard the annealing and/or stabilization of non-complementary nucleic acid molecules. As those in the art will appreciate, factors influencing nucleic acid hybridization conditions include, among others, nucleic acid size and nucleotide composition, temperature, salt, ionic strength, pH, reactant concentration, the presence of other molecules, including chaotropic agents, and length of time of hybridization.

"Event-specific promoter" refers to transcriptional promoter/enhancer or locus defining elements, or other elements which control gene expression as discussed above, whose transcriptional activity is altered upon response to cellular stimuli. Representative examples of such event-specific promoters include thymidine kinase or thymidylate synthase promoters, α or β interferon promoters and promoters that respond to the presence of hormones (either natural, synthetic or from other non-host organisms).

"Tissue-specific promoter" refers to transcriptional promoter/enhancer or locus defining elements, or other elements which control gene expression as discussed above, which are preferentially active in a limited number of tissue types. Representative examples of such tissue-specific promoters include the PEPCK promoter, HER2/neu promoter, casein promoter, IgG promoter, Chorionic Embryonic Antigen promoter, elastase promoter, porphobilinogen deaminase promoter, insulin promoter, growth hormone factor promoter, tyrosine hydroxylase promoter, albumin promoter, alphafetoprotein promoter, acetyl-choline receptor promoter, alcohol dehydrogenase promoter, α or β globin promoters, T-cell receptor promoter, or the osteocalcin promoter.

"Transduction" involves the association of a replication defective, recombinant retroviral particle with a cellular receptor, followed by introduction of the nucleic acids carded by the particle into the cell. "Transfection" refers to a method of physical gene transfer wherein no retroviral particle is employed.

A "unique nucleic acid fragment" is one comprising a contiguous nucleotide sequence that is not known to exist in another nucleic acid molecule. Unique fragments can be identified by selecting particular nucleotide sequences found in a factor VIII coding region and comparing such sequences to those found in various nucleotide sequence databases, including Genbank (available from the National Center for Biotechnology Information [NCBI], European Molecular Biology Library [EMBL]), and GeneSeq™ (Intelligenetics, Inc., Mountain View, Calif.) using publicly available computer algorithms such as FASTA™ (Genetics Computer Group, Madison, Wis.) and BLAST (NCBI).

"Vector construct", "retroviral vector", "recombinant vector", and "recombinant retroviral vector" refer to a nucleic acid construct capable of directing the expression of a full length factor VIII gene. The retroviral vector must include at least one transcriptional promoter/enhancer or locus defining element(s), or other elements which control gene expression by other means such as alternate splicing, nuclear RNA export, post-translational modification of messenger, or post-transcriptional modification of protein. In addition, the retrovital vector must include a nucleic acid molecule which, when transcribed in the presence of a full length factor VIII gene, is operably linked thereto and acts as a translation initiation sequence. Such vector constructs must also include a packaging signal, long terminal repeats (LTRs) or portion thereof, and positive and negative strand primer binding sites appropriate to the retrovirus used (if these are not already present in the retroviral vector). Optionally, the vector construct may also include a signal which directs polyadenylation, as well as one or more restriction sites and a translation termination sequence. By way example, such vectors will typically include a 5' LTR, a tRNA binding site, a packaging signal, an origin of second strand DNA synthesis, and a 3' LTR or a portion thereof. In order to express a full length factor VIII polypeptide from such a vector, a full length factor VIII ceding region is also included.

Numerous aspects and advantages of the invention will be apparent to those skilled in the art upon consideration of the following detailed description which provides illumination of the practice of the invention.

DETAILED DESCRIPTION OF THE INVENTION

The present invention is based on the unexpected discovery that retroviral vectors comprising a nucleic acid molecule encoding full length factor VIII can be efficiently packaged into infectious retroviral particles and that cells transduced in vivo with such vectors produce biologically active factor VIII. As a result, retroviral vectors encoding full length factor VIII can be used for purposes of gene therapy. A more thorough description of such retroviral vectors, their production and packaging, and uses therefore is provided below.

In humans and other mammals examined, the factor VIII gene is known to be located on the X chromosome and span more than about 186 kb (kilobases). Transcription of the gene results in the eventual production of a mRNA of approximately 8,800 nucleotides encoding the full length polypeptide. The nucleotide sequence of the factor VIII coding region is presented in SEQ ID NO: 1 and has been published in various locations. For instance, see Wood, et al. (*Nature*, 312:330, 1984; U.S. Pat. No. 4,965,199). The coding region spans 7,056 nucleotides, exclusive of 5' and 3' untranslated sequences, but for the translation termination codon TGA. Allelic variants of this sequence encoding biologically active, full length factor VIII likely exist and may also be used in the practice of this invention. Such allergic variants may contain differences only detectable at the nucleic acid level, i.e., due to conservative nucleotide substitutions. On the other hand, they may be manifest by one or more amino acid differences in the overall sequence, i.e., by deletions, insertions, substitutions, or inversions of one or more amino acids. However, no such variant will comprise less than about 95% (by number) of the nucleotides of SEQ ID NO: 1.

In vivo, a major site of factor VIII production is thought to be the liver, but factor VIII mRNA has also been detected in the spleen, kidney and lymph nodes [White, et al., *Blood*, 73: 1, 1989]. However, other cell types which do not normally express the protein can express the polypeptide, including smooth muscle cells of the primary vasculature [Powell, et al., *FEBS Letters*, 303(2,3):173, 1992]. As a result, hematopoietic cells are particularly attractive gene therapy targets [Hoeben, et al., supra].

Native human full length factor VIII is a heat labile single chain glycoprotein comprising 2351 amino acids, with the N-terminal 19 residues functioning as a leader peptide that is later cleaved. The remaining 2332 residues comprise six distinct domains, arranged as follows: A1-A2-B-A3-C1-C2. The A domains (each about 330 amino acids in length) share homology with factor V and the plasma copper binding protein ceruloplasmin. Similarly, the two C domains (each about 150 amino acids) are homologous to those of factor V and other phospholipid binding proteins. The B domain contains 19 of the 25 potential sites (Asn-X-Ser/Thr) for N-linked glycosylation, although it is not required for procoagulant activity. During intracellular processing prior to secretion, the polypeptide is cleaved after residues 1313 and 1648 to generate heavy ("a") and light ("b") chains, respectively. The observed relative molecular weight of the a chain is about 200 kD, as measured by SDS-PAGE, and that of the b chain is about 80 kD. The two chains then assemble in a non-covalent complex around a divalent metal ion.

During processing, factor VIII is also sulfated on six Tyr residues (amino acid residues 346, 718, 719, 723, 1664, and 1680). Sulfation is required for full functional activity, but not for synthesis or secretion (Pittman, et al., *Biochemistry*, 31:3315, 1992). Huttner, et al., *Mol. Cell. Biol.*, 6:97, 1988) proposed a consensus sequence for tyrosine sulfation, corresponding to 7 potential sulfation sites in full length factor VIII. Many proteins known to interact with thrombin, such as hirudin, fibrinogen, heparin cofactor II, bovine factor X, vitronectin, factor V, and factor VIII, have one or more sulfated tyrosine residues. In hirudin, Tyr sulfation in the C-terminal region increases binding affinity to the anion binding exosite of thrombin (Rydel, et al., *Science*, 249:277, 1990; Niehrs, et al., *J. Biol. Chem.*, 262:16467, 1990). All sites which are sulfated in factor VIII border thrombin, factor IXa, or activated protein C cleavage sites. Using various techniques, for instance, site directed mutagenesis, nucleic acids encoding full length factor VIII having fewer or additional sulfation sites can be readily generated.

Prior to activation, factor VIII circulates in plasma bound to yon Willebrand factor (vWf), which stabilizes it. Factor VIII has a plasma half-life of about 12 hr. Factor VIII and vWf circulate in plasma as a non-covalently linked complex. vWf is necessary for mediating platelet-vessel interactions at sites of vascular injury (Saenko, et al., *J. Bio. Chem.*, 269(15):11601, 1994). The factor VIII heavy chain is minimally represented by the A1-A2 domains, and it exhibits heterogeneity due the presence of some or all of the contiguous B domain. The light chain corresponds to the A3-C 1-C2 domains and contains sites for binding vWf (Lollar, et al., *J. Biol. Chem.*, 263:10451, 1988; Hamer, et al., *Eur. J. Biochem.*, 166:37, 1987), activated protein C (Walker, et al., *J. Bio. Chem.*, 265:1484, 1990), and phospholipids (Foster, et al., *Blood*, 75:1999, 1990; Bloom, J. W. *Thromb. Res.*, 48:439, 1987). vWF prevents factor VIII from binding to phospholipids and platelets (Fay, et al., *J. Biol. Chem.*, 266:2172, 1991; Nesheim, et al., *J. Biol. Chem.*, 266:17815, 1991). Upon activation by thrombin, factor VIIIa dissociates from vWf (Lollar, et al., supra). A polypeptide comprising only the C2 domain, and expressed in *E. coli* binds to phosphatidylserine or vWf in a dose dependent manner. The vWf binding sire was localized to amino acids 2303 to 2332, and its occupancy is also known to prevent factor VIII-phosphatidylserine binding (Foster, et al., supra). Residues 1673–1689 (part of the light chain acidic region) and sulfated $Tyr^{1680}$ may also be required for high affinity binding of vWf to the factor VIII light chain (Leyte, et al., *J. Biol. Chem.*, 266:740, 1991), as thrombin cleavage at residue 1689 leads to loss of vWf binding.

Figure 3:
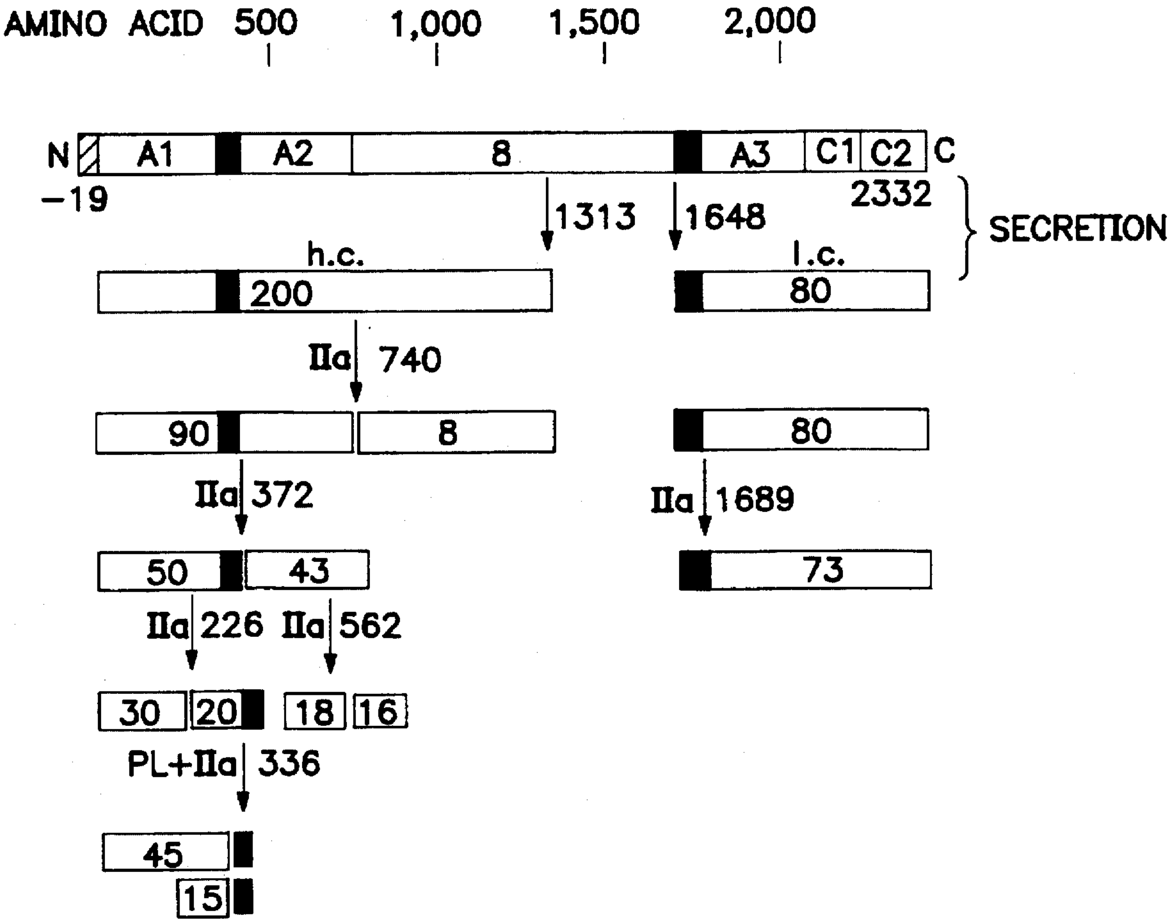
FIG. 3 diagrams in vivo factor VIII processing. The full length factor VIII translation product is shown, including the 19 amino acid leader peptide (hatched region) at the N-terminus ("N"). Acidic regions between the A1 and A2 domain and the B and A3 domains are shaded. Cleavage points are indicated by amino acid number. Cleavage by thrombin is indiacted by "IIa". "h.c." and "l.c." represent the heavy and light chains, respectively. Numbering in the various boxes represents relative molecular weights in kD. "PL" means "phospholipid."

Factor VIII has two thrombin cleavage sites, between $Arg^{739}$ and $Ser^{740}$ and between $Arg^{1689}$ and $Ser^{1690}$ (Toole, et al., supra), yielding a 90 kD heavy chain and 73 kD light chain. Factor VIIIa acts as a cofactor with factor IXa (activated by factor XIa or VIIa), calcium ions, and phospholipids to activate factor X to form factor Xa, potentially on the surface of platelets or endothelial cells. Thrombin cleavage activates the procoagulant activity of factor VIII 20- to 200-fold. Factor VIIIa is then inactivated by various proteolytic activities. See FIG. 3 for a depiction of factor VIII processing.

In addition to encoding a full length factor VIII polypeptide comprising the amino acid sequence set forth in SEQ ID NO: 2, the present invention also envisions recombinant retroviral vectors which encode analogues of full length factor VIII wherein one or more amino acids are substituted, deleted, or inserted. Such alterations may provide for improved expression, enhanced stability, presentation of altered functional properties, altered serum half-life and clearance times, different patterns of glycosylation, etc. Representative examples include addition, deletion, or movement of one or more sulfation sites, glycosylation sites, etc. Also, changes may be engineered to improve metal ion binding or thrombin interactions, to introduce novel disulfide bridges to improve stability, etc. In preferred embodiments of the invention, full length factor VIII analogues will retain those sequences required for activation by thrombin. Thrombin activation of various full length factor VIII analogs can be assayed by comparing the kinetics of thrombin activation of native, plasma derived factor VIII versus that of an analog. Activation can be measured using a standard coagulation assay (see Example 3, infra) or a plasma-free tenase assay using purified proteins, among other assays.

Nucleic acids encoding full length factor VIII polypeptide analogues will differ in more one more nucleotides as compared to the nucleotide sequence set out in SEQ ID NO: 1. Alterations may be introduced by a variety of techniques, including random mutagenesis, site directed mutagenesis, or solid state nucleic acid synthesis. For example, all or part of the full length factor VIII gene present in a retroviral vector may be modified to contain one or more degenerate codons, i.e., a different codon coding for the same amino acid, preferred for expression in the particular species to be treated. A "codon preferred for expression" in a particular species is a codon which is represented in highly expressed structural genes of that species in a proportion greater than would be randomly expected. In any event, the "preferred" codon will code for the same amino acid as the codon that was replaced due to the degenerate nature of the genetic code. Codon preferences are known for many species, and can be deduced by statistical analysis of codon usage in genes encoding highly expressed proteins in species for which such preferences have not yet been determined. One or more preferred codons can be incorporated into a nucleic acid molecule by various methods, including site directed mutagenesis and partial or complete synthetic gene synthesis. Alternatively, all or part of the gene may be modified to minimize the formation of secondary structures which might reduce the efficiency of translation or post transcriptional processing. For instance, Lynch, et al. (*Human Gene Therapy*, 4:259, 1993) studied the use of retroviral vectors for transfer and expression of truncated forms of factor VIII lacking part or all of non-essential B-domain sequences. Expression and vital titer were about 100-fold lower than titer and protein production from identical retroviral backbones containing other cDNAs. This reduction correlated with a 100-fold lower accumulation of factor VIII retroviral vector RNAs as compared to other vector RNAs. Analysis revealed the presence of sequences in the factor VIII coding region that may inhibit vector RNA accumulation. One or more of such sequences can be modified using well known techniques.

Generation of Recombinant Retroviral Vectors

As noted above, the present invention provides compositions and methods comprising recombinant retroviral vectors. The construction of recombinant retroviral vectors is described in greater detail in an application entitled "Recombinant Retroviruses" (U.S. Ser. No. 07/586,603, filed Sep. 21, 1990, which is hereby incorporated by reference in its entirety). These recombinant retroviral vectors may be used to generate transduction competent retroviral vector particles by introducing them into appropriate packaging cell lines (see U.S. Ser. No. 07/800,921, which is hereby incorporated by reference in its entirety).

In the broadest terms, the retroviral vectors of the invention comprise a transcriptional promoter/enhancer or locus defining element(s), or other elements which control gene expression by other means such as alternate splicing, nuclear RNA export, post-translational modification of messenger, or post-transcriptional modification of protein. In addition, the retroviral vector must include a nucleic acid molecule which, when transcribed in the presence of a full length factor VIII gene, is operably linked thereto and acts as a translation initiation sequence. Such vector constructs must also include a packaging signal, long terminal repeats (LTRs) or portion thereof, and positive and negative strand primer binding sites appropriate to the retrovirus used (if these are not already present in the retrovital vector). Optionally, the vector construct may also include a signal which directs polyadenylation, as well as one or more restriction sites and a translation termination sequence. By way example, such vectors will typically include a 5' LTR, a tRNA binding site, a packaging signal, an origin of second strand DNA synthesis, and a 3' LTR or a portion thereof. Such vectors do not contain one or more of a complete gag, pol, or env gene, thereby rendering them replication incompetent. In addition, nucleic acid molecules coding for a selectable marker are neither required nor preferred.

Preferred retroviral vectors contain a portion of the gag coding sequence, preferably that portion which comprises a splice donor and splice acceptor site, the splice acceptor site being positioned such that it is located adjacent to and upstream from the full length factor VIII coding region. In a particularly preferred embodiment, the gag transcriptional promoter is positioned such that an RNA transcript initiated therefrom contains the 5' gag UTR and the full length factor VIII coding region. As an alternative to the gag promoter to control expression of the full length factor VIII coding region, other suitable promoters, some of which are described below, may be employed. In addition, alternate enhancers may be employed in order to increase the level of full length factor VIII expression.

In preferred embodiments of the invention, retroviral vectors are employed, particularly those based on Moloney murine leukemia virus (MoMLV). MoMLV is a murine retrovirus which has poor infectivity outside of mouse cells. The related amphotropic N2 retrovirus will infect cells from human, mouse and other organisms. Other preferred retroviruses which may be used is the practice of the present invention include Gibbon Ape Leukemia Virus (GALV) (Todaro, et al., *Virology*, 67:335, 1975; Wilson, et al., *J. Vir.*, 63:2374, 1989), Feline Immunodeficiency Virus (FIV) (Talbatt, et al., *Proc. Nat'l. Acad. Sci. USA*, 86:5743, 1984), and Feline Leukemia Virus (FeLV) (Leprevette, et al., *J. Vir.*, 50:884, 1984; Elder, et al., *J. Vir.*, 46:871, 1983; Steward, et al., *J. Vir.*, 58:825, 1986; Riedel, et al., *J. Vir.*, 60:242, 1986), although retroviral vectors according to the invention derived from other type C retroviruses (Weiss, *RNA Tumor Viruses*, vols. I and II, Cold Spring Harbor Laboratory Press, N.Y.) can also be generated.

Similarly, other promoters could be used, including but not necessarily limited to the cytomegalovirus major immediate early promoter (CMV MIE), the early and late SV40 promoters, the adenovirus major late promoter, thymidine kinase or thymidylate synthase promoters, α or β interferon promoters, event or tissue specific promoters, etc. Promoters may be chosen so as to potently drive expression or to produce relatively weak expression, as desired. As those in the art will appreciate, numerous RNA polymerase II and RNA polymerase III dependent promoters can be utilized in practicing the invention.

In another preferred embodiment, the retroviral vector contains a splice donor (SD) site and a splice acceptor (SA) site, wherein the SA is located upstream of the site where the full length factor VIII coding region ("gene") is inserted into the recombinant retroviral vector. In a preferred embodiment, the SD and SA sites will be separated by a short, i.e., less than 400 nucleotide, intron sequence. Such sequences may serve to stabilize RNA transcripts. Such stabilizing sequences typically comprise a SD-intron-SA configuration located 5' to the coding region of full length factor VIII.

The recombinant retrovital vectors of the invention will also preferably contain transcriptional promoters derived from the gag region operably positioned such that a resultant transcript comprising the full length factor VIII coding region further comprises a 5' gag UTR (untranslated region) upstream of the factor VIII coding region.

In one embodiment, recombinant retroviral vectors comprising a full length factor VIII gene are under the transcriptional control of an event-specific promoter, such that upon activation of the event-specific promoter the full length factor VIII coding region is expressed. Numerous event-specific promoters may be utilized within the context of the present invention, including for example, promoters which are activated by cellular proliferation (or are otherwise cell-cycle dependent) such as the thymidine kinase or thymidylate synthase promoters (Merrill, *Proc. Natl. Acad. Sci. USA*, 86:4987, 1989; Deng, et al., *Mol. Cell. Biol.*, 9:4079, 1989); or the transferrin receptor promoter, which will be transcriptionally active primarily in rapidly proliferating cells (such as hematopoietic cells) which contain factors capable of activating transcription from these promoters preferentially to express and secrete factor VIII into the blood stream; promoters such as the α or β interferon promoters which are activated when a cell is infected by a virus (Fan and Maniatis, *EMBO J.*, 8:101, 1989; Goodbourn, et al., *Cell*, 45:601, 1986); and promoters which are activated by the presence of hormones, e.g., estrogen response promoters. See Toohey et al., *Mol. Cell. Biol.*, 6:4526, 1986.

In another embodiment, recombinant retroviral vectors are provided which comprise a full length factor VIII ceding region under the transcriptional control of a tissue-specific promoter, such that upon activation of the tissue-specific promoter the factor VIII gene is expressed. A wide variety of tissue-specific promoters may be utilized within the context of the present invention. Representative examples of such promoters include: liver-specific promoters, such as Phospho-Enol-Pyruvate Carboxy-Kinase ("PEPCK") (Hatzoglou, et al., *J. Biol. Chem.*, 263:17798, 1988; Benvenisty, et al., *Proc. Natl. Acad. Sci. USA*, 86:1118, 1989; Vaulont, et al., *Mol. Cell. Biol.*, 6:4409, 1989), the alcohol dehydrogenase promoter (Felder, *Proc. Natl. Acad. Sci. USA*, 86:5903, 1989), and the albumin promoter and the alphafetoprotein promoter (Feuerman, et al., *Mol. Cell. Biol.*, 9:4204, 1989; Camper and Tilghman, *Genes Develop.*, 3:537, 1989); B cell specific promoters such as the IgG promoter; pancreatic acinar cell specific promoters such as the elastase promoter (Swift, et al., *Genes Develop.*, 3:687, 1989) and promoters which are specific for β cells of the pancreas, such as the insulin promoter (Ohlsson, et al., *Proc. Natl. Acad. Sci. USA*, 85:4228, 1988; Karlsson, et al., *Mol. Cell. Biol.*, 9:823, 1989); breast epithelial specific promoters such as the casein promoter (Doppler, et al., *Proc. Natl. Acad. Sci. USA*, 86:104, 1989) and the whey (wap) promoter; promoters which regulate skeletal muscle such as the myo-D binding site (Burden, *Nature*, 341:716, 1989; Weintraub, et al., *Proc. Natl. Acad. Sci. USA*, 86:5434, 1989); promoters which are specific for the pituitary gland, such as the growth hormone factor promoter (Ingraham, et al., *Cell*, 55:519, 1988; Bodner, et al., *Cell*, 55:505, 1988); promoters which are specific for melanosomes, such as the tyrosine hydroxylase promoter; T-cell specific promoters such as the T-cell receptor promoter (Anderson, et al., *Proc. Natl. Acad. Sci. USA*, 85:3551, 1988; Winoto and Baltimore, *EMBO J.*, 8:29, 1989); bone-specific promoters such as the osteocalcin promoter (Markose, et al., *Proc. Natl. Acad. Sci. USA*, 87:1701, 1990; McDonnell, et al., *Mol. Cell. Biol*, 9:3517, 1989; Kerner, et al., *Proc. Natl. Acad. Sci. USA*, 86:4455, 1989), the IL-2 promoter, IL-2 receptor promoter, and the MHC Class II promoter, and hematopoietic tissue specific promoters, for instance erythoid specific-transcription promoters which are active in erythroid cells, such as the porphobilinogen deaminase promoter (Mignotte, et al., *Proc. Natl. Acad. Sci. USA*, 86:6458, 1990), α or β globin specific promoters (van Assendelft. et al., *Cell*, 56:969, 1989, Forrester, et al., *Proc. Natl. Acad. Sci. USA*, 86:5439, 1989), endothelial cell specific promoters such as the vWf promoter, magakaryocyte specific promoters such as β-thromboglobulin, and many other tissue-specific promoters.

Retroviral vectors according to the invention may also contain a non-LTR enhancer or promoter, e.g., a CMV or SV40 enhancer operably associated with other elements employed to regulate expression of the factor VIII gene. Additionally, retrovital vectors from which the 3' LTR enhancer has been deleted, thereby inactivating the 5' LTR upon integration into a host cell genome, are also contemplated by the invention. A variety of other elements which control gene expression may also be utilized within the context of the present invention, including, for example, locus-defining elements such as those from the β-globin gene and CD2, a T cell marker. In addition, elements which control expression at the level of splicing, nuclear export, and/or translation may also be included in the retrovital vectors. Representative examples include the β-Globin intron sequences, the rev and are elements from HIV-1, the constitutive transport element (CTE) from Mason-Pfizer monkey virus (MPMV), a 219 nucleotide sequence that allows rev-independent replication of rev-negative HIV proviral clones, and a Kozak sequence. Rev protein functions to allow nuclear export of unspliced and singly spliced HIV RNA molecules. The MPMV element allows nuclear export of intron- containing mRNA. The CTE element maps to MPMV nucleotides 8022–8240 a (Bray, et al., *Biochemistry*, 91:1256, 1994).

In a preferred embodiment, retrovital vectors of the invention will include a "cis" element 5' located between the promoter and the full length factor VIII coding region. Such "cis" elements will generally comprise a splice donor and splice acceptor site separated by a short intervening, non-coding sequence. A particularly preferred cis element comprises a splice donor site from CMV and a splice acceptor from immunoglobulin, separated by a short CMV intron sequence, as described below in Example 1.

Retroviral vectors according to the invention will often be encoded on a plasmid, a nucleic acid molecule capable of propogation, segregation, and extrachromosomal maintenance upon introduction into a host cell. As those in the art will understand, any of a wide range of existing or new plasmids can be used in the practice of the invention. Such plasmids contain an origin of replication and typically are modified to contain a one or more multiple cloning sites to facilitate recombinant use. Preferably, plasmids used in accordance with the present invention will be capable of propogation in both eukaryotic and prokaryoric host cells.

Generation of Packaging Cells

Another aspect of the invention relates to methods of producing retroviral particles incorporating the retroviral vectors described herein. In one embodiment, vectors are packaged into infectious virions through the use of a packaging cell. Briefly, a packaging cell is a cell comprising, in addition to its natural genetic complement, additional nucleic acids coding for those retroviral structural polypeptides required to package a retroviral genome, be it recombinant (i.e., a retroviral vector) or otherwise. The retroviral particles are made in packaging cells by combining the retroviral genome with a capsid and envelope to make a transduction competent, preferably replication defective, virion. Briefly, these and other packaging cells will contain one, and preferably two or more nucleic acid molecules coding for the various polypeptides, e.g., gag, pol, and env, required to package a retroviral vector into an infectious virion. Upon introduction of a nucleic acid molecule coding for the retroviral vector, the packaging cells will produce infectious retroviral particles. Packaging cell lines transfected with a retroviral vector according to the invention which produce infectious virions are referred to as "producer" cell lines.

A wide variety of animal cells may be utilized to prepare the packaging cells of the present invention, including without limitation, epithelial cells, fibroblasts, hepatocytes, endothelial cells, myoblasts, astrocytes, lymphocytes, etc. Preferentially, cell lines are selected that lack genomic sequences which are homologous to the retroviral vector construct, gag/pol expression cassette and env expression cassette to be utilized. Methods for determining homology may be readily accomplished by, for example, hybridization analysis (Martin et al., *Proc. Natl. Acad. Sci., USA*, vol. 78:4892–96, 1981; and U.S. Ser. No. 07/800,921).

The most common packaging cell lines (PCLs) used for MoMLV vector systems (psi2, PA12, PA317) are derived from murine cell lines. However, murine cell lines are typically not the preferred choice to produce retrovital vectors intended for human therapeutic use because such cell lines are known to: contain endogenous retroviruses, some of which are closely related in sequence and retroviral type to the MLV vector system used here; contain non-retroviral or defective retroviral sequences that are known to package efficiently; and cause deleterious effects due to the presence of murine cell membrane components.

An important consideration in developing packaging cell lines useful in the invention is the production therefrom of replication incompetent virions, or avoidance of generating replication-competent retrovirus (RCR) [Munchau et al., *Virology*, vol. 176:262–65, 1990]. This will ensure that infectious retroviral particles harboring the recombinant retrovital vectors of the invention will be incapable of independent replication in target cells, be they in vitro or in vivo. Independent replication, should it occur, may lead to the production of wild-type virus, which in turn could lead to multiple integrations into the chromosome(s) of a patient's cells, thereby increasing the possibility of insertional mutagenesis and its associated problems. RCR production can occur in at least two ways: (1) through homologous recombination between the therapeutic proviral DNA and the DNA encoding the retroviral structural genes ("gag/pol" and "env") present in the packaging cell line; and (2) generation of replication-competent virus by homologous recombination of the proviral DNA with the very large number of defective endogenous proviruses found in the packaging cell line.

To circumvent inherent safety problems associated with the use of murine based recombinant retroviruses, as are preferred in the practice of this invention, packaging cell lines may be derived from various non-murine cell lines. These include cell lines from various mammals, including humans, dogs, monkeys, mink, hamsters, and rats. As those in the art will appreciate, a multitude of packaging cell lines can be generated using techniques known in the art (for instance, see U.S. Ser. No. 08/156,789 and U.S. Ser. No. 08/136,739). In preferred embodiments, cell lines are derived from canine or human cell lines, which are known to lack genomic sequences homologous to that of MoMLV by hybridization analysis (Martin et al., supra). A particularly preferred parent dog cell line is D17 (A.T.C.C. accession no. CRL 8543). HT-1080 (A.T.C.C. accession no. CCL 121; Graham et al., *Vir.*, vol. 52:456, 1973) and 293 cells (Felgner et al., *Proc. Nat'l. Acad. Sci. USA* 84:7413, 1987) represent particularly preferred parental human cell lines. Construction of packaging cell lines from these cell lines for use in conjunction with a MoMLV based recombinant retroviral vector is described in detail in U.S. Ser. No. 08/156,789, supra.

Thus, a desirable prerequisite for the use of retroviruses in gene therapy is the availability of retroviral packaging cell lines incapable of producing replication competent, or "wild-type," virus. As packaging cell lines contain one or more nucleic acid molecules coding for the structural proteins required to assemble the retroviral vector into infectious retroviral particles, recombination events between these various constructs might produce replication competent virus, i.e., infectious retroviral particles containing a genome encoding all of the structural genes and regulatory elements, including a packaging signal, required for independent replication. In the past several years, many different constructions have been developed in an attempt to obviate this concern. Such constructions include: deletions in the 3' LTR and portions of the 5' LTR (see, Miller and Buttimore, *Mol. Cell. Biol.*, vol. 6:2895–2902, 1986), where two recombination events are necessary to form RCR; use of complementary portions of helper virus, divided among two separate plasmids, one containing gag and pol, and the other containing env (see, Markowitz et al., *J. Virol.*, vol. 62:1120–1124; and Markowitz et al., *Virology*, vol 167: 600–606, 1988), where three recombination events are required to generate RCR.

More recently, further improved methods and compositions for inhibiting the production of replication incompetent retrovirus have been developed. See co-owned U.S. Ser. No. 09/028,126, filed Sep. 7, 1994. Briefly, the spread of replication competent retrovirus generated through recombination events between the recombinant retroviral vector and one or more of the nucleic acid constructs coding for the retroviral structural proteins may be prevented by providing vectors which encode a non-biologically active inhibitory molecule, but which produce a nucleic acid molecule encoding a biologically active inhibitory molecule in the event of such recombination. The expression of the inhibitory molecule prevents production of RCR either by killing the producer cell(s) in which that event occurred or by suppressing production of the retroviral vectors therein. A variety of inhibitory molecules may be used, including ribozymes, which cleave the RNA transcript of the replication competent virus, or a toxin such as ricin A, tetanus, or diphtheria toxin, herpes thymidine kinase, etc. As those in the art will appreciate, the teachings therein may be readily adapted to the present invention.

In addition to issues of safety, the choice of host cell line for the packaging cell line is of importance because many of the biological properties (such as titer) and physical properties (such as stability) of retroviral particles are dictated by the properties of the host cell. For instance, the host cell must efficiently express (transcribe) the vector RNA genome, prime the vector for first strand synthesis with a cellular tRNA, tolerate and covalently modify the MLV structural proteins (proteolysis, glycosylation, myristylation, and phosphorylation), and enable virion budding from the cell membrane. For example, it has been found that vector made from the mouse packaging line PA317 is retained by a 0.3 micron filter, while that made from a CA line described herein will pass through. Furthermore, sera from primates, including humans, but not that from a wide variety of lower mammals or birds, is known to inactivate retroviruses by an antibody independent complement lysis method. Such activity is non-selective for a variety of distantly related retroviruses. Retroviruses of avian, murine (including MoMLV), feline, and simian origin are inactivated and lysed by normal human serum. See Welsh et al., (1975) *Nature*, vol. 257:612–614; Welsh et al., (1976) *Virology*, vol. 74:432–440; Banapour et al., (1986) *Virology*, vol. 152:268–271; and Cooper et al., (1986) *Immunology of the Complement System*, Pub. American Press, Inc., pp:139–162. In addition, replication competent murine amphotropic retroviruses injected intravenously into primates in vivo are cleared within 15 minutes by a process mediated in whole or in part by primate complement (Cornetta et al. (1990), *Human Gene Therapy*, vol. 1:15–30; Cornetta et al. ( 1991), *Human Gene Therapy*, vol. 2:5–14). However, it has recently been discovered that retroviral resistance to complement inactivation by human serum is mediated, at least in some instances, by the packaging cell line from which the retroviral particles were produced. Retroviruses produced from various human packaging cell lines were resistant to inactivation by a component of human serum, presumably complement, but were sensitive to serum from baboons and macques. See commonly owned U.S. Ser. No. 08/367,071, filed on a date even herewith. Thus, in a preferred embodiment of the invention, recombinant retr VIII are partials coding for full length factor VIII are produced in human packaging cell lines, with packaging cell lines derived from HT1080 or 293 cells being particularly preferred.

In addition to generating infectious, replication defective recombinant retroviruses as described above, at least two other alternative systems can be used to produce recombinant retroviruses carrying the vector construct. One such system (Webb, et al., *BBRC*, 190:536, 1993) employs the insect virus, baculovirus, while the other takes advantage of the mammalian viruses vaccinia and adenovirus (Pavirani, et al., *BBRC*, 145:234, 1987). Each of these systems can make large amounts of any given protein for which the gene has been cloned. For example, see Smith, et al. (*Mol. Cell. Biol.*, 3:12, 1983); Piccini, et al. (*Meth. Enzymology*, 153:545, 1987); and Mansour et al. (*Proc. Natl. Acad. Sci. USA*, 82:1359, 1985). These retroviral vectors can be used to produce proteins in tissue culture cells by insertion of appropriate genes and, hence, could be adapted to make retroviral vector particles from tissue culture. In an adenovirus system, genes can be inserted into vectors and used to express proteins in mammalian cells either by in vitro construction (Ballay, et al., 4:3861, 1985) or by recombination in cells (Thummel, et al, *J. Mol. Appl. Genetics*, 1:435, 1982).

In an alternative approach, which is more truly extracellular, retroviral structural proteins are made in a baculovirus system (or other protein production systems, such as yeast or *E. coli*) in a similar manner as described in Smith et al. (supra). Recombinant retroviral genomes are made by in vitro RNA synthesis (see, for example, Flamant and Sorge, *J. Virol.*, 62:1827, 1988). The structural proteins and RNA genomes are then mixed with tRNA, followed by the addition of liposomes with embedded env protein and cell extracts (typically from mouse cells) or purified components (which provide env and other necessary processing, and any or other necessary cell-derived functions). The mixture is then treated (e.g., by sonication, temperature manipulation, or rotary dialysis) to allow encapsidation of nascent retroviral particles. This procedure allows production of high titer, replication incompetent recombinant retroviruses without contamination with pathogenic retroviruses or replication-competent retroviruses.

Another important factor to consider in the selection of a packaging cell line is the viral liter produced therefrom following introduction of a nucleic acid molecule from which the retroviral vector is produced. Many factors can limit viral titer. One of the most significant limiting factors is the expression level of the packaging proteins gag, pol, and env. In the case of retroviral particles, expression of retroviral vector RNA from the provirus can also significantly limit titer. In order to select packaging cells and the resultant producer cells expressing high levels of the required products, an appropriate titering assay is required. As described in greater detail below, a suitable PCR-based titering assay has been developed.

In addition to preparing packaging and producer cell lines which supply proteins for packaging that are homologous for the backbone of the viral vector, e.g., retroviral gag, pol, and env proteins for packaging of a retroviral vector, packaging and producer systems which result in chimeric viral particles, for instance a MoMLV-based retroviral vector packaged in a DNA virus capsid, may also be employed. Many other packaging and producer systems based on viruses unrelated to that of the viral vector can also be utilized, as those in the art will appreciate.

Altering the Host Range of Recombinant Retroviral Particles

Another aspect of the invention concerns retroviral vectors having an altered host range. The host cell range specificity of a retrovirus is determined in part by the env gene products present in the lipid envelope. Interestingly, envelope proteins from one retrovirus can often substitute, to varying degrees, for that of another retrovirus, thereby altering host range of the resultant vector. Thus, packaging cell lines (PCLs) may be generated to express either amphotropic, ecotropic, xenotropic, or polytropic envelopes. Additionally, retroviruses according to the invention which contain "hybrid" or "chimeric" envelope proteins can be similarly generated. Vector produced from any of these packaging cell lines can be used to infect any cell which contains the corresponding distinct receptor (Rein and Schultz, *Virology*, 136:144, 1984).

The assembly of retroviruses is characterized by selective inclusion of the retroviral genome and accessory proteins into a budding retroviral particle. Interestingly, envelope proteins from non-murine retrovirus sources can be used for pseudotyping (i.e., the encapsidation of viral RNA from one species by viral proteins of another species) a vector to alter its host range. Because a piece of cell membrane buds off to form the retroviral envelope, molecules normally in the membrane may be carried along on the viral envelope. Thus, a number of different potential ligands can be put on the surface of retroviral particles by manipulating the packaging cell line in which the vectors are produced or by choosing various types of cell lines with particular surface markers.

Miller et al. (*Mol. Cell. Biol.*, 5:431, 1985) constructed a MoMLV-derived retroviral vector to introduce dihydrofolate reductase into susceptible cells and included the envelope region from the related amphotropic retrovirus 4070A to broaden the host range of the vector. Similarly, envelope proteins from amphotropic, ecotropic, polytropic, and xenotropic retroviruses can be utilized. In addition, alterations in the host range can be effected by including heterologous membrane-associated proteins, i.e., membrane-associated proteins having at least one origin other than a virus of the same viral family as the origin of the nucleocapsid protein of the vector particle, within a retrovital particle. For instance, vesicular stomatitis virus (VSV), a member of the rhabdovims family, is known to participate in pseudotype formation with retroviruses. See U.S. Ser. No. 07/658,632, filed 19 Feb., 1991.

Briefly, in this aspect the present invention provides for enveloped retroviral particles, comprising: a nucleocapsid including nucleocapsid protein having an origin from a first virus, which is a retrovirus; a packageable nucleic acid molecule encoding full length factor VIII associated with the nucleocapsid; and a membrane-associated protein which determines a host range, the membrane-associated protein being from other than a retrovirus of the same taxonomic family as the first retrovirus. Preferably, the membrane-associated protein is from a second virus having a different host range than the first virus, such as a naturally occurring membrane-associated protein, e.g., VSV G protein.

In another preferred form of the present invention, the membrane-associated protein of the vector particles is a chimeric or hybrid protein including an exterior receptor binding domain and a membrane-associated domain, at least a portion of the exterior receptor binding domain being derived from a different origin than at least a portion of the membrane-associated domain. The chimeric protein is preferably derived from two origins, wherein no more than one of the two origins is retroviral. In addition, it is preferable that at least a portion of the exterior receptor binding domain is from VSV G protein.

Another embodiment of this aspect of the present invention concerns cell lines that produce the foregoing vector particles. Preferably, such cell lines are stably transfected with a nucleic acid molecule encoding the membrane-associated protein, whose expression is driven by an inducible promoter.

Membrane-associated proteins other than VSV G protein which are good candidates for providing altered host range when used in accordance with the present invention include those proteins from other enveloped viruses that bind host receptors and facilitate infection. As those in the art will appreciate, vectors incorporating nucleic acid molecules encoding such proteins can readily be employed to generate packaging cell lines from which retroviral particles having altered host ranges can be produced. By way of illustration, one suitable alternative is the gD gene from HSV (Herpes Simplex Virus), which can be used to obtain a host range which includes human neural ganglia tissue.

Retroviral particles according to the invention may be targeted to a specific cell type by including in the retrovital particles a component, most frequently a polypeptide or carbohydrate, which binds to a cell surface receptor specific for that cell type. Such targeting may be accomplished by preparing a packaging cell line which expresses a chimeric env protein comprising a portion of the env protein required for viral particle assembly in conjunction with a cell-specific binding domain. In another embodiment, env proteins from more than one viral type may be employed, such that resultant viral particles contain more than one species of env proteins. Yet another embodiment involves inclusion of a cell specific ligand in the retroviral capsid or envelope to provide target specificity. In a preferred embodiment at this aspect of the invention, the env gene employed encodes all or a portion of the env protein required for retroviral assembly in conjunction with a receptor binding domain of a polypeptide ligand known to interact with a cell surface receptor whose tissue distribution is limited to the cell type(s) to be targeted, e.g., an endothelial cell located at the luminal surface of a blood vessel. In this regard, it may be preferable to utilize a receptor binding domain which binds receptors expressed at high levels on the target cell's surface, or alternatively which are expressed at relatively higher levels in the target tissue as compared to other cells.

In addition to, or in lieu of, tissue targeting, tissue specific promoters can be employed to drive the expression of full length factor VIII in only specific cell types.

In order to control the specific site of integration into a patient's genome in those instances where the viral vector employed leads to integration of the viral genome into a chromosome of the recipient cell, as occurs in the case of retroviral infection, homologous recombination or use of a modified integrase enzyme which directs insertion to a specific site can be utilized. Such site-specific insertion of the full length factor VIII gene may provide for gene replacement therapy, reduced chances of insertional mutagenesis, minimize interference from other sequences present in the patient's DNA, and allow insertion at specific target sites to reduce or eliminate expression of an undesirable gene (such as a viral or tumorigenic gene) in the patient's DNA.

Non-viral membrane-associated proteins may also be used to alter the host range of vector particles. Representative examples include polypeptides which act as ligands for given cell surface receptors or other cell surface moieties. Depending on the tissue distribution of the receptor for the protein in question, the retroviral vector could be targeted to a vast range of human cells, to a subset of cells, or to a single cell type. Thus, for example, all human cells, all white blood cells, or only T-helper cells could be targeted.

When a ligand to be included within the retroviral envelope is not a naturally occurring membrane-associated protein, it is necessary to associate the ligand with the membrane, preferably by making a "hybrid" or "chimeric" envelope protein. It is important to understand that such hybrid envelope proteins can contain extracellular domains from proteins other than other viral or retroviral env proteins. To accomplish this, the gene coding for the ligand can be functionally combined with sequences coding for a membrane-associated domain. By "naturally occurring membrane associated protein", it is meant those proteins that in their native state exist in vivo in association with lipid membrane such as that found associated with a cell membrane or on a viral envelope. As such, hybrid envelopes can be used to tailor the tropism (and effectively increase titers) of a retroviral vector coding for full length factor VIII, as the extracellular component of env proteins from retroviruses are responsible for specific receptor binding. The cytoplasmic domain of these proteins, on the other hand, play a role in virion formation. The present invention recognizes that numerous hybrid env gene products (i.e., specifically, retroviral env proteins having cytoplasmic regions and extracellular binding regions which do not naturally occur together) can be generated and may alter host range specificity. As a result, recombinant retroviruses can be produced that specifically bind to targeted cells.

In a preferred embodiment, this is accomplished by recombining the gene coding for the ligand (or part thereof conferring receptor binding activity) proximate of the membrane-binding domain of VSV G protein or other retrovirally derived envelope proteins that stably assemble with a given capsid protein. The resulting construct will code for a bifunctional chimeric protein capable of cell targeting and inclusion in a retroviral lipid envelope.

Within a preferred embodiment of the invention, susceptible T-cells or monocytes may be targeted with vectors which carry VSV G, HIV env or hybrid env, in order to direct absorption of vector particles to $CD4^+$ cells. For example, viral vectors may be targeted by producing vector particles which will infect cells using the HIV env protein (gp120) as a receptor. Such HIV-tropic viruses may, within preferred embodiments be produced from an MLV-based packaging cell line constructed from cells which have naturally high levels of CD4 protein (for example, Sup T1 cells) and/or CD26 protein in their cell membrane, or from any cell type "engineered" to express such proteins. The resultant virions, which form by budding from the cell membrane itself, contain the CD4 (and/or CD26) proteins in their membrane. Since membranes containing CD4 (and CD26) are known to fuse with membranes carrying HIV env, these virions should fuse with cells containing HIV env and result in the specific infection of HIV-infected cells which have gp120 on their surface. Such a packaging cell line may require the presence of an MLV env protein to allow proper virion assembly and budding to result in infectious virions. If so, an MLV env which does not infect human cells (such as ecotropic env) would be used such that viral entry will occur only through the CD4 (and/or CDCC)/HIV env interaction and not through the MLV env cell receptor, which would presumably not depend upon the presence of HIV-env for infection. Alternatively, the requirement for MLV env may be satisfied by a hybrid envelope where the amino-terminal binding domain has been replaced by the amino-terminal HIV-env binding domain of CD4 and/or CD26. This inversion of the normal virus-receptor interaction can be used for all types of viruses whose corresponding cellular receptor has been identified.

Vector particles having non-native membrane-associated ligands as described herein, will, advantageously, have a host range determined by the ligand-receptor interaction of the membrane-associated protein. Thus, for targeted delivery of retroviral vectors encoding full length factor VIII, a vector particle having altered host range can be produced using the methods of the present invention. The ligand will be selected to provide a host range including the targeted cell type. Many different targeting strategies can be employed in connection with this aspect of the invention. For example, there are a number of progenitor cell types found in bone marrow that differentiate into blood cells. Many blood cells have relatively short life spans and therefore progenitor cells must continually divide and differentiate to replace the lost cells. In a preferred embodiment, gene therapy for hemophilia targets hematopoietic progenitor cells, including pluripotent stem cells. These progenitor cells are known to have unique cellular determinants that permit histological identification, separation from other cell types by various techniques, including fluorescence activated cell sorting (FACS) and positive and negative selection [see U.S. Pat. No. 5,061,620], and which can be used as cell receptors for the membrane-associated proteins of the vector particles of the present invention.

As used herein, a hematopoietic stem cell is a primitive, or immature, cell capable of self-renewal and which is capable of differentiating into precursor cells of all hematopoietic lineages, i.e., they are said to be "totipotent." Recombinant vectors according to the invention may be introduced into such cells or any their more differentiated progeny, such as the various primitive progenitors and the more lineage committed precursor cells that give rise to the various hematopoietic cell lineages. One marker for such early hematopoietic cells is CD34, which can be identified using monoclonal antibodies. See U.S. Pat. No. 4,714,680; WO 93/25216, published Dec. 23, 1993. WO 93/25216 describes a class of hematopoietic stem cells as having the phenotype $CD34^{30}$ /$CD38^-$/HLA-$DR^-$ and lacking the lineage committed antigens CD33, CD10, CD5, and CD71. Representative examples of anti-CD34 antibodies include 12.8 (Andrews, et al, *Blood*, 67:842, 1986) and My10 (Civin, et al., *J. Immunol.*, 133:157, 1984, commercially available from Becton Dickinson under the designation HPCA-2). Other antibodies may be also utilized to target a selected cell type, such as anti-CD4 antibodies to target CD4+T-cells and anti-CD8 antibodies to target CD8+ cells (see generally, Wilchek, et al., *Anal. Blochem.*, 171:1, 1988).

The vectors may be constructed to target these cell types for gene delivery by including an expressible gene which encodes a membrane-associated protein that binds to a unique cellular determinant of such progenitor cell types. Examples of such progenitor cell types which could be targeted using vector particles of the present invention include pluripotent stem cells, erythroblasts, lymphoblasts, myeloblasts and megakaryocytes.

Those in the art will also recognize that it is also possible to add ligand molecules exogenously to the retroviral particles which are either incorporated into the lipid envelope or which can be linked chemically to the lipid or protein constituents thereof.

Targeting a retroviral vector encoding full length factor VIII to a predetermined locus on a chromosome may also be employed. Clear advantages of such targeting include avoidance of insertional mutagenesis and assuring integration at sites known to be transcriptionally active. Techniques for targeting proviral integration to specific sites include integrase modification. See U.S. Ser. No. 08/156,789, supra.

It is further envisioned that the therapy of the present invention be performed either in vivo or in vitro. For in vitro therapy (also refered to as "ex vivo therapy"), cells are removed and transduced in vitro. For vector particles having membrane-associated proteins which determine the appropriate host range, there would be no need to purify the cells to be targeted in vitro because the vector would specifically transduce only the targeted cells. Thus, bone marrow samples could be removed from a subject and the desired cell type transduced. The transduced cells could then be returned to the same patient or one who is HLA matched.

In addition a wide variety of high affinity binding pairs can be used as targeting elements. Representative examples of include biotin/avidin with an affinity ($K_D$) of $10^{-15}$ M (Richards, *Meth. Enz.*, 184:3, 1990; Green, *Adv. in Protein Chem.*, 29:85, 1985) and cystatin/papain with an affinity of $10^{-14}$M (Bjork, et al., *Biochemistry*, 29: 1770, 1990).

A wide variety of other high affinity binding pairs may also be developed, for example, by preparing and selecting antibodies which recognize a selected antigen with high affinity (see generally, U.S. Pat. Nos. RE 32,011, 4,902,614, 4,543,439, and 4,411,993; see also *Monoclonal Antibodies, Hybridomas: A New Dimension in Biological Analyses*, Plenum Press, Kennett, McKearn, and Bechtol, eds., 1980, and *Antibodies: A Laboratory Manual*, Harlow and Lane eds., Cold Spring Harbor Laboratory Press, 1988). The binding pair for such antibodies, typically other antibodies or antibody fragments, may be produced by recombinant techniques (see Huse, et al., *Science*, 246:1275, 1989; see also Sastry, et al., *Proc. Natl. Acad. Sci. USA*, 86:5728, 1989; and Michelle Alting-Mees, et al., *Strategies in Molecular Biology*, 3:1, 1990).

As will be evident to one of ordinary skill in the art given the disclosure provided herein, either member (or molecule) of the affinity binding pair may be coupled to the retroviral particle or vehicle in which such particles are contained, e.g., liposomes, or, conversely, to the targeting element. Nevertheless, within preferred embodiments of the invention, the larger of the two affinity binding pairs (e.g., avidin of the avidin/biotin pair) is coupled to the retroviral particle or other vehicle. As utilized within the context of targeting, the term "coupled" may refer to either noncovalent or covalent interactions, although generally covalent bonds are preferred. Numerous coupling methods may be utilized, including, for example, use of crosslinking agents such as N-succinimidyl-3-(2-pyridyl dithio) propionate ("SPDP"; Carlson, et al., *J. Biochem.*, 173:723, 1978) and other such compounds known in the art.

In particularly preferred embodiments of the invention, a member of the high affinity binding pair is either expressed on, or included as an integral part of, a retroviral particle, e.g., in the retroviral lipid envelope. For example, a member of the high affinity binding pair may be co-expressed with the envelope protein as a hybrid protein.

Preparation and Purification of Recombinant Retroviral Particles

Another aspect of the invention concerns the preparation of recombinant retroviral particles. Retroviral particles according to the invention can be produced in a variety of ways, as those in the art will appreciate. For example, producer cells, i.e., cells containing all necessary components for retroviral vector packaging (including a nucleic acid molecule encoding the retroviral vector), can be grown in roller bottles, in bioreactors, in hollow fiber apparatus, and in cell hotels. Cells can be maintained either on a solid support in liquid medium, or gown as suspensions. A wide variety of bioreactor configurations and sizes can be used in the practice of the present invention.

Cell factories (also termed "cell hotels") typically contain 2, 10, or 40 trays, are molded from virgin polystyrene, treated to provide a Nuclon D surface, and assembled by sonic welding one to another. Generally, these factories have two port tubes which allow access to the chambers for adding reagents or removing culture fluid. A 10-layer factory provides 6000 $cm^2$ of surface area for growing cells, roughly the equivalent of 27 T-225 flasks. Cell factories are available from a variety of manufacturers, including for example Nunc. Most cell types are capable of producing high titer vector for 3–6 days, allowing for multiple harvests. Each cell type is tested to determine the optimal harvest time after seeding and the optimal number of harvest days. Cells are typically initially gown in DMEM supplemented with 2–20% FBS in roller bottles until the required number of cells for seeding a cell factory is obtained. Cells are then seeded into the factories and 2 liters of culture supernatant containing vector is harvested later at an appropriate time. Fresh media is used to replenish the cultures.

Hollow fiber culture methods may also be used. Briefly, high titer retroviral production using hollow fiber cultures is based on increasing viral concentration as the cells are being cultured to a high density in a reduced volume of media. Cells are fed nutrients and waste products are diluted using a larger volume of fresh media which circulates through the lumen of numerous capillary fibers. The cells are cultured on the exterior spaces of the capillary fibers in a bioreactor chamber where cell waste products are exchanged for nutrients by diffusion through 30 kD pores in the capillary fibers. Retroviruses which are produced from the cell lines are too large to pass through the pores, and thus concentrate in the hollow fiber bioreactor along side of the cells. The volume of media being cultured on the cell side is approximately 10 to 100 fold lower then volumes required for equivalent cell densities cultured in tissue culture dishes or flasks. This decrease fold in volume inversely correlates with the fold induction of titer when hollow fiber retrovital titers are compared to tissue culture dishes or flasks. This 10–100 fold induction in titer is seen when an individual retroviral producer cell line is amiable to hollow fiber growth conditions. To achieve maximum cell density, the individual cells must be able to grow in very close proximity and on top of each other. Many cell lines will not grow in this fashion and retrovital packaging cell lines based on these types of cell lines may not achieve 10 fold increases in titer. Cell lines which would grow very well would be non-adherent cell line and it is believed that a retroviral producer line based on a non-adherent cell line may reach 100 fold increases in titer compared to tissue culture dishes and flasks.

Regardless of the retroviral particle and production method, high titer (from about $10^7$–$10^{11}$ cfu/mL) stocks can be prepared that will cause high level expression of the desired products upon introduction into appropriate cells. When all components required for retroviral particle assembly are present, high-level expression will occur, thereby producing high titer stocks. And while high titer stocks are preferred, retroviral preparations having titers ranging from about $10^3$ to $10^6$ cfu/mL may also be employed, although retroviral titers can be increased by various purification methods, as described below.

After production by an appropriate means, the infectious recombinant retroviral particles may be preserved in a crude or purified form. Crude retroviral particles are produced by cultivated infected cells, wherein retrovital particles are released from the cells into the culture media. The virus may be preserved in crude form by first adding a sufficient amount of a formulation buffer to the culture media containing the recombinant virus to form an aqueous suspension.

Recombinant retroviral particles can also be preserved in a purified form. More specifically, prior to the addition of formulation buffer, the crude retroviral preparation described above is clarified by passing it through a filter, and then concentrated, such as by a cross flow concentrating system (Filtron Technology Corp., Nortborough, Mass.). Within one embodiment, DNase is added to the concentrate to digest exogenous DNA. The digest is then diafiltrated to remove excess media components and establish the recombinant virus in a more desirable buffered solution. The diafiltrate is then passed over a gel filtration Sephadex S-500 gel column and a purified recombinant virus is eluted.

Crude recombinant retroviral preparations can also be purified by ion exchange column chromatography, such as is described in more detail in U.S. Ser. No. 08/093,436. In general, the crude preparation is clarified filter, and the filtrate loaded onto a column containing a highly sulfonated cellulose matrix, wherein the amount of sulfate per gram of cellulose ranges from about 6–15 μg. The recombinant retrovirus is eluted from the column in purified form by using a high salt buffer. The high salt buffer is then exchanged for a more desirable buffer by passing the eluate over a molecular exclusion column. The purified preparation may then be formulated or stored, preferably at −70° C.

Additionally, the preparations containing recombinant retroviruses according to the invention can be concentrated during purification in order to increase the titer of recombinant retrovirus. A wide variety of methods may be utilized for increasing retroviral concentration, including for example, precipitation of recombinant retroviruses with ammonium sulfate, polyethylene glycol ("PEG") concentration, concentration by centrifugation (either with or without gradients such as PERCOLL, or "cushions" such as sucrose, use of concentration filters (e.g., Amicon filtration), and 2-phase separations.

Briefly, to accomplish concentration by precipitation of recombinant retroviruses with ammonium sulfate, ammonium sulfate is added slowly to an appropriate concentration, followed by centrifugation and removal of the ammonium sulfate either by dialysis or by separation on a hydrophobic column.

Alternatively, recombinant retroviruses may be concentrated from culture medium with PEG [Green, et al, *PNAS* 67:385–393, 1970; Syrewicz, et al., *Appl. Micro.* 24:488–494, 1972]. Such methods are rapid, simple, and inexpensive. However, like ammonium sulfate precipitation, use of PEG also concentrates other proteins from solution.

Within other embodiments, recombinant retroviruses may be concentrated by centrifugation, and more particularly, low speed centrifugation, which avoids difficulties associated with pelleting that accompanies high speed centrifugation (e.g., virus destruction or inactivation).

Recombinant retroviruses encoding full length factor VIII may also be concentrated by an aqueous two-phase separation method. Briefly, polymeric aqueous two-phase systems may be prepared by dissolving two different non-compatible polymers in water. Many pairs of water-soluble polymers may be utilized in the construction of such two-phase systems, including for example polyethylene glycol ("PEG") or methylcellulose, and dextran or dextran sulfate (see Walter and Johansson, *Anal. Biochem.* 155:215–242, 1986; Albertsson, "Partition of Cell Particles and Macromolecules" Wiley, N.Y., 1960). As described in more detail below in Example 13, utilizing PEG at concentrations ranging from 5% to 8% (preferably 6.5%), and dextran sulfate at concentrations ranging from 0.4% to 1% (preferably 0.4), an aqueous two-phase system may be established for purifying recombinant retroviruses. Utilizing such procedures, approximate 100-fold concentration can be achieved with yields of approximately 50% or more of the total starting retrovirus.

For purposes of illustration, a representative concentration process which combines several concentration steps is set forth below. Briefly, recombinant retroviruses may be prepared either from roller bottles, cell factories, or bioreactors prior to concentration. Removed media containing the recombinant retrovirus may be frozen at −70∞∞C, or more preferably, stored at 2∞∞C to 8∞∞C in large pooled batches prior to processing.

For material obtained from a bioreactor, the recombinant retrovirus pool is first clarified through a 0.8 μm filter (1.2 μm glass fiber pre-filter, 0.8 μm cellulose acetate) connected in series with a 0.65 μm filter. This filter arrangement provides approximately 2 square feet of filter, and allows processing of about 15–20 liters of pooled material before clogging. For material obtained from roller bottles or cell factories, a single 0.65 μm cartridge (2 sq. ft.) normally suffices for volumes up to 40 liters. For 80 liter cell factory processes, a 5 sq. ft. filter may be required.

Preferably, after clarification the filter is rinsed with buffer (e.g., 150 mM NaCl, 25 mM Tris, pH 7.2–7.5). Following clarification, recombinant retroviruses are concentrated by tangential flow ultrafiltration utilizing cassettes with a 300,000 mw cut off. For bioreactor material (containing 12% to 16% FBS), 4–5 L of material may be concentrated per cassette. For roller bottles or cell factories at 12–16% FBS, 5–6 L of material may be concentrated per cassette. Finally, for cell factories containing 10% FBS, 8–9 L of material may be concentrated per cassette. Utilizing such procedures at an appropriate pressure differential between filtrate and retentate, up to 80 liters of material may be concentrated to a volume of less than 500 mL in under two hours. This process also provides a yield of about 80%.

Following the ultrafiltration step, DNAse may be added to a concentration of 50 U/mL, and recirculated at a lower pump speed with the filtrate line closed for 30 minutes. Discontinuous diafiltration is then accomplished by adding additional buffer and utilizing the same cross differential pressure as before. Generally, recovery after this step is approximately 70%.

Concentrated material is then subjected to column chromatography on a Phamacia S-500 HG size exclusion gel, utilizing 50 mM NaCl and 25 mM Tris pH 7.2–7.5 as minimum salt and ionic strength concentrations. Generally, recombinant retroviruses elute off in the first peak.

Tangential flow filtration may once again be utilized to further reduce the volume of the preparation, after which the concentrated material is sterilized by filtration through a 0.2 μm Millipore filter.

As an alternative to in vivo production, the retroviral packaging proteins may be produced, together or separately, from appropriate cells. However, instead of introducing a nucleic acid molecule enabling production of the viral vector, an in vitro packaging reaction is conducted comprising the gag, pol, and env proteins, the retroviral vector, tRNA, and other necessary components. The resulting retroviral particles can then purified and, if desired, concentrated.

Formulation of Pharmaceutical Compositions

Another aspect of the invention relates to pharmaceutical compositions comprising recombinant retroviral vectors as described above, in combination with a pharmaceutically acceptable carder or diluent. Retroviral particles comprising such retroviral vectors can be formulated in crude or, preferably, purified form. Such pharmaceutical compositions may be prepared either as a liquid solution, or as a solid form (e.g., lyophilized) which is resuspended in a solution prior to administration. In addition, the composition may be prepared with suitable carriers or diluents for topical administration, injection, or nasal, oral, vaginal, sub-lingual, inhalant, intraocular, enteric, or rectal administration.

Pharmaceutically acceptable carriers or diluents are nontoxic to recipients at the dosages and concentrations employed. Representative examples of carriers or diluents for injectable solutions include water, isotonic saline solutions, preferably buffered at a physiological pH (such as phosphate-buffered saline or Tris-buffered saline), mannitol, dextrose, glycerol, and ethanol, as well as polypeptides or proteins such as human serum albumin (HSA). A particularly preferred composition comprises a vector or recombinant virus in 10 mg/mL mannitol, 1 mg/mL HSA, 20 mM Tris, pH 7.2, and 150 mM NaCl . In this case, since the recombinant retroviral vector represents approximately 1 μg of material, it may be less than 1% of high molecular weight material, and less than 1/100,000 of the total material (including water). This composition is stable at −70° C. for at least six months.

Pharmaceutical compositions of the present invention may also additionally include factors which stimulate cell division, and hence, uptake and incorporation of a recombinant retroviral vector. Additionally, such compositions may include inhibitors of complement activation, such as saccharides that compete with pre-existing human antibodies against alpha galactose epitopes, for example B-Disaccharide-R (Chembiomed), B-Disaccharide (Dextra), B-Trisaccharide (Dextra), B-Tetrasaccharide (Dextra), A-Fucosylated trisaccharide-R, 6-0-B-D-Galactopyranosyl-D-galactose, A-Fucosylated trisaccharide-R, Decay Accelarating Factor, and HRF20 [Neethling, et al. (1994), *Transplantation*, vol. 57, pp:959–963; Hayashi, et al. (1994), *Transplantation Proceedings*, vol. 26, no. 3, pp: 1243–1244]. Such complement inhibitors may be especially effective when used with recombinant retroviruses that are produced in packaging cell lines derived from a species different from that of the patient to whom the composition is to be administered.

Pharmaceutical compositions of the present invention may also additionally include factors which suppress an immune response to the retroviral particles encoding full length factor VIII. In addition, pharmaceutical compositions of the present invention may be placed within containers or kits, along with packaging material which provides instructions regarding the use of such pharmaceutical compositions. Generally, such instructions will describe the reagent concentration, as well as within certain embodiments, relative mounts of excipient ingredients or diluents (e.g., water, saline or PBS) which may be necessary to reconstitute the pharmaceutical compositions.

Particularly preferred methods and compositions for preserving recombinant viruses are described in U.S. applications entitled "Methods for Preserving Recombinant Viruses" (U.S. Ser. No. 08/135,938, filed Oct. 12, 1993, and U.S. Ser. No. 8/153,342, filed Nov. 15, 1993, which are incorporated herein by reference in their entirety).

The use of recombinant retroviruses to treat patients requires that the product be able to be transported and stored for long periods at a desired temperature such that infectivity and viability of the recombinant retrovirus is retained. The difficulty of preserving recombinant retroviruses absent low temperature storage problems in Third presents problems in Third World countries, where adequate refrigeration capabilities are often lacking. For example, in Africa millions of children die annually from infectious diseases such as measles. Vaccines necessary for the prevention of such diseases cannot be widely distributed because refrigeration is not readily accessible.

The initial stabilization of materials in dry form to the preservation of antitoxins, antigens and bacteria has been described (Flosodort, et al., *J. Immunol.*, 29:389, 1935). However, a limitation in this process included partial denaturation of proteins when dried from an aqueous state at ambient temperatures. Drying from the frozen state helped reduce this denaturation and led to efficient preservation of other biological materials, including bacteria and viruses (Stamp, et al., *J. Gen. Microbiol.*, 1:251, 1947; Rowe, et al., *Virology*, 42:136, 1970; and Rowe, et al., *Cryobiology*, 8:153, 1971). More recently, sugars such as sucrose, raffinose, glucose and trehalose were added in various combinations as stabilizing agents prior to lyophilization of viruses. The use of sugars enhanced recovery of viable viruses, for research purposes which require that only some virus survive for later propagation.

Recombinant retroviruses according to the invention can be stored in liquid, or preferably, lyophilized form. Factors influencing stability include the formulation (liquid, freeze dried, constituents thereof, etc.) and storage conditions, including temperature, storage container, exposure to light, etc. Alternatively, retroviral particles according to the invention can be stored as liquids at low temperatures. In a preferred embodiment, the recombinant retroviruses of the invention are formulated to preserve infectivity in a lyophilized form at elevated temperatures, and for this form to be suitable for injection into patients following re, constitution.

Recombinant retrovirus may be preserved in a crude or purified form. Crude retroviral preparations may be produced by various cell culture methods, where retroviral particles are released from the cells into the culture media. Retroviral particles may be preserved in crude form by adding a sufficient amount of formulation buffer. Typically, the formulation buffer is an aqueous solution containing various components, such as one or more saccharides, high molecular weight structural additives, buffering components, and/or amino acids.

The recombinant retroviruses described herein can also be preserved in a purified form. For instance, prior to the addition of formulation buffer, crude preparations as described above may be clarified by filtration, and then concentrated. DNase may be added to the concentrate to digest exogenous DNA, followed by diafiltration to remove excess media components and substitute in a more desirable buffered solution. The diafiltrate may then passed over a gel filtration column, such as a Sephadex™ S-500 gel column, and the eluted retroviral particles retained. A sufficient amount of formulation buffer may then be added to the eluate to reach a desired final concentration of the constituents and to minimally dilute the retroviral preparation. The aqueous suspension can then be stored, preferably at −70° C., or immediately formulated.

In an alternative procedure, the crude preparation can be purified by ion exchange column chromatography, as described in co-owned U.S. patent application Ser. No. 08/093,436. Briefly, the crude recombinant virus is clarified by filtration and then loaded onto a column comprising a highly sulfonated cellulose matrix. Highly purified recombinant retrovirus is eluted from the column using a high salt buffer, which is then exchanged for a more desirable buffer by passing the eluate over a molecular exclusion column. After recovery, formulation buffer may then added to adjust the final concentration, as discussed above, followed by low temperature storage or immediate formulation.

When a dried formulation is desired, an aqueous preparation containing a crude or purified retroviral preparation can be prepared by lyophilization or evaporation. Lyophilization involves cooling the aqueous preparation below the glass transition temperature or below the eutectic point temperature of the solution, and removing water by sublimation. For example, a multistep freeze drying procedure as described by Phillips et al. (*Cryobiology*, vol. 18:414, 1981) can be used to lyophilize the formulated recombinant virus, preferably from a temperature of −40° C. to −45° C. The resulting composition should contain less than 10% water by weight. Once lyophilized, such a preparation is stable and may be stored at −20° C. to 25° C.

In an evaporative method, water is removed by evaporation from the retroviral preparation aqueous suspension at ambient temperature. Evaporation can be accomplished by various techniques, including spray drying (see EP 520,748), where the preparation is delivered into a flow of preheated gas, usually air, whereupon water rapidly evaporates from droplets of the suspension. Once dehydrated, the recombinant retrovirus is stable and may be stored at −20° C. to 25° C.

As mentioned previously, aqueous preparations comprising retroviruses according to the invention used for formulation are typically composed of one or more saccharides, high molecular weight structural additives, buffering components, and water, and may also include one or more amino acids. It has been found that the combination of these components acts to preserve the activity of the recombinant virus upon freezing and lyophilization, or drying through evaporation. See co-owned U.S. Ser. No. 08/153,342, filed Nov. 15, 1993. Various saccharides may be used alone or in combination, including sucrose, mannitol, glucose, trehalose, inositol, fructose, maltose, and galactose, with lactose being particularly preferred. The concentration of the saccharide can range from 0.1% to 30% by weight, preferably from about 1% to 12% by weight. A particularly preferred concentration of lactose is 3%−4% by weight. Additionally, saccharide combinations can also be employed, including lactose and mannitol or sucrose and mannitol. It will also be evident to those skilled in the art that it may be preferable to use certain saccharides in the aqueous solution when the lyophilized formulation is intended for room temperature storage. Specifically, disaccharides, such as lactose or trehalose, are preferred for such formulations.

One or more high molecular weight structural additives may be used to aid in preventing retroviral aggregation during freezing and provides structural support in the lyophilized or dried state. In the context of the present invention, structural additives are considered to be of "high molecular weight" if they are greater than 5000 daltons. A preferred high molecular weight structural additive is human serum albumin (HSA), although other substances may also be used, such as hydroxyethyl-cellulose, hydroxymethyl-cellulose, dextran, cellulose, gelatin, povidone, etc. Preferably, the concentration of the high molecular weight structural additive can range from 0.05% to 20%, with 0.1% to 10% by weight being preferred, and a concentration of 0.1% by weight HSA being particularly preferred.

Amino acids, if present, tend to further preserve retroviral infectivity. A preferred amino acid is arginine, but other amino acids such as lysine, ornithine, serine, glycine, glutamine, asparagine, glutamic acid or aspartic acid can also be used. Preferably, the amino acid concentration ranges from 0.1% to 10% by weight. A particularly preferred arginine concentration is 0.1% by weight.

A variety of buffering components may be used to maintain a relatively constant pH, depending on the pH range desired, preferably between 7.0 and 7.8. Suitable buffers include phosphate buffer and citrate buffer. A particularly preferred formulation pH is 7.4, and a preferred buffer is tromethamine.

It may also be preferable to include in the formulation a neutral salt to adjust the final iso-osmotic salt concentration. Suitable neutral salts include sodium chloride, potassium chloride, and magnesium chloride, with sodium chloride being preferred.

A particularly preferred method of preserving recombinant retroviruses in a lyophilized state for subsequent reconstitution comprises: (a) preparing an aqueous recombinant retroviral preparation comprising, in addition to the recombinant retrovirus, about (i) 4% by weight of lactose, (ii) 0.1% by weight of human serum albumin, (iii) 0.03% or less by weight of NaCl, (iv) 0.1% by weight of arginine, and a sufficient amount of tromethamine to provide a pH of approximately 7.4; (b) cooling the preparation to a temperature of about −40° C. to −45° C. to form a frozen preparation; and (c) removing water from the frozen preparation by sublimation to form a lyophilized composition having less than 2% water by weight. It is preferred that the recombinant retrovirus be replication defective and suitable for administration into humans upon reconstitution.

The lyophilized or dehydrated viruses of the subject invention may be reconstituted using a variety of substances, but are preferably reconstituted using water. In certain instances, dilute salt solutions which bring the final formulation to isotonicity may also be used. In addition, it may be advantageous to use aqueous solutions containing components known to enhance the activity of the reconstituted virus. Such components include cytokines, such as IL-2, polycations, such as protamine sulfate, or other components which enhance the transduction efficiency of the reconstituted virus. Lyophilized or dehydrated recombinant virus may be reconstituted with any convenient volume of water or the reconstituting agents noted above that allow substantial, and preferably total solubilization of the lyophilized or dehydrated sample.

Administration of Recombinant Retroviral Particles

In another aspect of the present invention, methods are provided for treating hemophilia A, comprising administering to a warm-blooded animal, particularly a human, a recombinant retrovital vector as described above, such that a therapeutically efficacious amount of factor VIII is produced. As used herein, a "therapeutically effective amount" of factor VIII is an amount that promotes blood coagulation in a patient to an extent greater than that observed when the patient was not treated with factor VIII. A "therapeutically effective amount" of a retroviral vector according to the invention refers to the amount that must be administered to produce a therapeutically effective amount of factor VIII in a particular patient. In a patient suffering from hemophilia, a therapeutically effective amount of a retrovital vector is an amount that elicits production of sufficient factor VIII to produce therapeutically beneficial clotting and will thus generally be determined by each patient's attending physician, although serum levels of about 0.2 ng/mL (about 0.1% of "normal" levels) or more will be therapeutically beneficial. Typical dosages will range from about $10^5$ to $10^{12}$ infectious retroviral particles, with dosages of $10^7$ to $10^{10}$ infectious particles being preferred. Other dosage measures include the number of International Units of factor VIII detected in the blood of patients treated with retrovital particles according to the invention, as can be measured by an appropriate assay, e.g., a Coatest assay, as described below.

In some cases, retroviral vectors according to the invention will be administered as an adjunct to other therapy, such as hormonal, radiation, and/or chemotherapeutic treatment. Factors influencing the amount of full length factor VIII-encoding retroviral particles that will be administered include the age and general condition of the patient, the amount of endogenous, i.e., non-recombinant, factor VIII produced by the patient, etc. Hemophilia A has been categorized into four groups, depending upon serum factor VIII levels, as follows: severe (less than 1% of normal factor VIII levels), moderate, mild, and subclinical (Brinkhous, K. M., *Thrombosis Research*, 67:329, 1992).

In various embodiments of the invention, recombinant retroviral vectors may be administered by various routes in vivo, or ex vivo, as described in greater detail below. Alternatively, the retroviral vectors of the present invention may also be administered to a patient by a variety of other methods. Representative examples include transfection by various physical methods, such as lipofection (Felgner, et al., *Proc. Natl. Acad. Sci. USA*, 84:7413, 1989), direct DNA injection (Acsadi, et al., *Nature*, 352:815, 1991; microprojectile bombardment (Williams, et al., *Proc. Nat'l. Acad. Sci. USA*, 88:2726, 1991); liposomes of several types (see e.g., Wang, et al., *Proc. Nat'l. Acad. Sci. USA*, 84:7851, 1987); $CaPO_4$ (Dubensky, et al., *Proc. Nat'l. Acad. Sci. USA*, 81:7529, 1984); DNA ligand (Wu, et al., *J. Biol. Chem.*, 264:16985, 1989); or administration of nucleic acids alone (WO 90/11092). Other possible methods of administration can include injection of producer cell lines into the blood or, alternatively, into one or more particular tissues, grafting tissue comprising cells transduced with retroviral vectors according to the invention, etc.

When pharmaceutical compositions according to the invention are administered in vivo, i.e., to the cells of patient without prior removal of the cells from the patient, administration can be by one or more routes. In this context, "administration" is equivalent to "delivery." Typical routes of administration include traditional parenteral routes, such as intramuscular (i.m.), subcutaneous (sub-q), intravenous (i.v.), and interperitoneal (i.p.) injection. Other suitable routes include nasal, pulmonary, and even direct administration into a particular tissue, such as the liver, bone marrow, etc. In addition, other routes may be employed, as described below.

Transdermal or topical application of a pharmaceutical composition comprising a retroviral vector according to the invention may be used as an alternate route of administration because the skin is the most expansive and readily accessible organ of the human body. Transdermal delivery systems (TDS) are capable of delivering a retroviral particle through intact skin so that it reaches the systemic circulation in sufficient quantity to be therapeutically effective. TDS provide a variety of advantages, including elimination of gastrointestinal absorption problems and hepatic first pass effect, reduction of dosage and dose intervals, and improved patient compliance. The major components of TDS are a controlled release device composed of polymers, a recombinant retrovirus encoding full length factor VIII, excipients, and enhancers, and a fastening system to fix the device to the skin. A number of polymers have been described and include, but are not limited to, gelatin, gum arabic, paraffin waxes, and cellulose acetate phthalate (Sogibayasi, et al., *J. Controlled Release,* 29:177, 1994). These polymers can be dermatologically formulated into aqueous, powder, or oil phases. Various combinations can produce lotions, pastes ointments, creams, and gels, alone or together with the Additionally, iontophoresis may be used to cause increased penetration of ionized substances into or through the skin by the application of an electrical field. This method has the advantage of being able to deliver the drug in a pulsatile manner (Singh, et al, *Dermatology,* 187:235, 1993).

Topical administration may also be accomplished by encapsulating retroviral particles in liposomes. Hyaluronic acid has been used as a bioadhesive ligand for the formation of liposomes to enhance adherence and retention to the extracellular matrix in cases of burns and wound healing (Yerushalmi, et al., *Arch. Biochem. and Biophys,* 313:267, 1994). As those in the art will appreciate, methods of liposome preparation can be tailored to control size and morphology. Liposomes can also be made to include one or more targeting elements to target a specific cell type.

Ocular administration is an alternate route to achieve delivery of compositions described herein. Systemic absorption occurs through contact with the conjunctival and nasal mucosae, the latter occurring as the result of drainage through the nasolacrimal duct. Formulations such as those described above which further comprise inert ingredients such as buffers, chelating agents, antioxidants, and preservatives can be incorporated into ophthalmic dosage forms intended for multiple dose use. Formulations also may consist of aqueous suspensions, ointments, gels, inserts, bioadhesives, microparticles, and nanoparticles.

The nasal cavity also offers an alternative route of administration for compositions comprising a retroviral vector encoding full length factor VIII. For instance, the human nasal cavities have a total surface area of approximately 150 $cm^2$ and are covered by a highly vascular mucosal layer. A respiratory epithelium, comprised of columnar cells, goblet cells, and ciliary cuboidal cells, lines most of the nasal cavity (Chien, et al, *Crit. Rev. in Therap. Drug Car. Sys.,* 4:67, 1987). The subepithelium contains a dense vascular network and the venous blood from the nose passes directly into the systemic circulation, avoiding first-pass metabolism in the liver. Thus, delivery to the upper region of the nasal cavity may result in slower clearance and increased bioavallability of retroviral particles. The absence of cilia in this area is an important factor in the increased effectiveness of nasal sprays as compared to drops. The addition of viscosity-building agents, such as methycellulose, etc. can change the pattern of deposition and clearance of intranasal applications. Additionally, bioadhesives can be used as a means to prolong residence time in the nasal cavity. Various formulations comprising sprays, drops, and powders, with or without the addition of absorptive enhancers, have been described (see Wearley, L, supra).

Oral administration includes sublingual, buccal, and gastrointestinal delivery. Sublingual and buccal (cheek) delivery allow for rapid systemic absorption of retroviral particles and avoid hepatic first-pass metabolism and degradation in the stomach and intestines. Unidirectional buccal delivery devices can be designed for oral mucosal absorption only. Additionally, these devices can prevent diffusion-limiting mucus buildup to allow for enhanced absorption. Delivery through the gastrointestinal tract allows for precise targeting for drug release. Depending on the formulation, recombinant retroviruses can be specifically delivered to areas in the stomach, duodenum, jejunum, ileum, cecum, colon, or rectum. Oral formulations include tablets, capsules, aqueous suspensions, and gels. These may contain bioadhesive polymers, hydrodynamically balanced systems, gastroinflatable delivery devices, intragastric retention shapes, enteric coatings, excipients, or intestinal absorption promoters (Ritschel, W. A., *Meth. Exp. Clin. Pharmacol.,* 13::313, 1991).

The human rectum has a surface area of between 200 to 400 $cm^2$ and is abundant in blood and lymphatic vessels. This offers an alternative route for administrating compositions according to the invention. Depending on the actual site of administration, it may be possible to bypass first-pass metabolism by the liver. Targeting of the systemic circulation can be achieved by delivering the vehicle to an area behind the internal rectal sphincter which allows absorption directly into the inferior vena cava, thereby bypassing the portal circulation and avoiding metabolism in the liver. The liver can be targeted by delivering the vehicle to the region of the ampulla recti, which allows absorption into the portal system (Ritschel, supra.). Interestingly, liver transplantation rectifies hemophilia A, and factor VIII mRNA is detectable in the liver and in isolated hepatocytes (Zatloukal, et al., supra). These results suggest that delivery of retroviral vectors as described herein to the liver, directly or indirectly, will be among those that are preferred in the practice of this invention.

Alternatively, pulmonary administration can be accomplished through aerosolization. As the lungs are highly vascularized, this type of administration allows systemic delivery. The three systems commonly used for aerosol production are: the nebulizer, the pressurized metered dose inhaler, and the dry powder inhaler, all of which are known in the art. Aerosol therapy is very common in obstructive bronchial diseases but can be used as well as for the treatment of systemic diseases. The surface area of the adult human lung is approximately 75 $m^2$ and requires only one puff of an aerosol to cover this entire area within seconds. Absorption occurs quickly because the walls of the alveoli in the deep lung are extremely thin. Absorption and clearance depends on a number of factors, including particle size and solubility (Wearley, L, supra). Particles are preferably smaller than 5 μm in diameter.

The vaginal mucosa consists of stratified squamous epithelium. Gene delivery vehicles can be administered through the vaginal orifice onto the mucosa. Formulations include ointments, creams, and suppositories. Additional information regarding these and other routes of administration may be found in U.S. Ser. No. 08/366,788, filed on a date even herewith.

As an alternative to in vivo adminstration of the retroviral vectors and particles of the invention, ex vivo adminstration can be employed. Ex vivo treatment envisions withdrawl or removal of a population of cells from a patient. Exemplary cell populations include bone marrow cells, liver cells, and blood cells from the umbilical cord of a newborn. Such cells may be be processed to purify desired cells for transduction prior to such procedures, for instance to obtain subsets of such cell populations, e.g., $CD34^+$ bone marrow progenitor cells. Preferred methods of purification include various cell sorting techniques, such as antibody panning, FACS, and affinity chromatography using a matrix coupled to antibodies specifcially reactive to the desired cell type(s). Isolated cells are then transduced, after which they may be immediately re-introduced to the patient from which they were withdrawn. Alternatively, the cells may be expanded in culture by various techniques known to those skilled in the art prior to re-introduction.

In another embodiment of the invention, retroviral vectors encoding full length factor VIII are administered to hemophilic patients in conjunction with another therapeutic compound. As those in the art will appreciate, such compounds may include, but are not limited to, other gene delivery vehicles designed to deliver one or more other therapeutic genes to the patient, as is described in U.S. Ser. No. 08/368,210, filed on a date even herewith). For instance, a patient suffering from hemophilia A may also be infected with HIV and/or HBV. Thus, such a patient may also be treated with a gene delivery vehicle(s) designed to treat such a disease(s), for instance by stimulating the patient's immune system [see U.S. Ser. No. 08/136,739, supra; see also U.S. Ser. No. 08/032,385, filed Mar. 17, 1993]or by conditioning infected cells to become sensitive to a cytotoxic compound to be administered later [see U.S. Ser. No. 08/155,944, filed Nov. 18, 1993].

EXAMPLES

The following examples are included to more fully illustrate the present invention. Additionally, these examples provide preferred embodiments of the invention and are not meant to limit the scope thereof. Standard methods for many of the procedures described in the following examples, or suitable alternative procedures, are provided in widely reorganized manuals of molecular biology, such as, for example "Molecular Cloning," Second Edition (Sambrook, et al., Cold Spring Harbor Laboratory Press, 1987) and "Current Protocols in Molecular Biology" (Ausubel, et al., eds. Greene Associates/Wiley Interscience, N.Y., 1990).

Example 1

Construction of Retroviral Vectors Comprising a Full Length Factor VIII Gene This example describes the construction of several retroviral vectors comprising a nucleic acid molecule encoding a full length factor VIII polypeptide. As will be clear to those in the art, other comparable retroviral vectors can be similarly constructed.

A. Preparation of Plasmids Encoding Retroviral Backbones KT-3 and KT-1

The Moloney murine leukemia virus (MoMLV) 5' long terminal repeat (LTR) Eco RI-Eco RI fragment, including gag sequences, from the N2 vector (Armentano, et al., *J. Vir.*, 61:1647, 1987; Eglitas, et al., *Science*, 230:1395, 1985) is ligated into the plasmid $SK^+$ (Stratagene, La Jolla, Calif.). The resulting construct is designated N2R5. The N2R5 construct is mutated by site-directed in vitro mutagenesis to change the ATG start codon to ATT, preventing gag expression. This mutagenized fragment is 200 base pairs (bp) in length and flanked by Pst I restriction sites. The Pst I—Pst I mutated fragment is purified from the $SK^+$ plasmid and inserted into the Pst I site of the N2 MoMLV 5' LTR in plasmid pUC31 to replace the non-mutated 200 bp fragment. The plasmid pUC31 is derived from pUC19 (Stratagene, La Jolla, Calif.) and contains additional restriction sites Xho I, Bgl It, BssH II and Nco I between the Eco RI and Sac I sites of the polylinker. This construct is designated pUC31/N2R5gM.

A 1.0 kb MoMLV 3' LTR Eco RI-Eco RI fragment from N2 is next cloned into plasmid $SK^+$, resulting in a construct designated $N2R3^-$. A 1.0 kb Cla I-Hind III fragment is then purified from this construct. The Cla I—Cla I dominant selectable marker gene fragment from the pAFVXM retroviral vector (Kriegler et al., *Cell* 38:483, 1984; St. Louis et al., (1988) *Proc. Nat'l, Acad. Sci. USA*, vol. 85, pp:3150–3154), comprising a SV40 early promoter driving expression of the neomycin (neo) phosphotransferase gene, is cloned into the $SK^+$ plasmid. This construct is designated $SK^+$ $SV_2$-neo. A 1.3 kb Cla I-Bst BI gene fragment is then purified from the $SK^+SV_2$-neo plasmid.

A plasmid encoding the KT-3 (pKT-3) retroviral vector is generated by ligating the 1.0 kb MoMLV 3' LTR Cla I-Hind III fragment (from $N2R3^-$) into like-digested pUC31/N2R5gM. The 1.3 Kb Cla I-Bst BI fragment encoding the neo gene is then inserted into the Cla site of the resultant plasmid construct.

A plasmid, pKT-1, is also constructed encoding a retrovital backbone similar to KT-3, with the exception that the dominant selectable marker gene, neo, is not inserted into the plasmid. pKT-1 is used to produce KT-1-based retrovital vectors comprising a full length factor VIII gene.

B. Production of Plasmid Vectors Encoding Full-Length Factor VIII

The following is a description of the construction of several retroviral vectors encoding a full-length factor VIII cDNA. Due to the packaging constraints of retroviral vectors and because selection for transduced cells is not a requirement for therapy, a retroviral backbone, e.g., KT-1, lacking a selectable marker gene is employed.

A gene encoding full length factor VIII can be obtained from a variety of sources. One such source is the plasmid pCIS-F8 (EP 0 260 148 A2, published Mar. 3, 1993), which contains a full length factor VIII cDNA whose expression is under the control of a CMV major immediate-early (CMV MIE) promoter and enhancer. The factor VIII cDNA contains approximately 80 bp of 5' untranslated sequence from the factor VIII gene and a 3' untranslated region of about 500 bp. In addition, between the CMV promoter and the factor VIII sequence lies a CMV intron sequence, or "cis" element. The cis element, spanning about 280 bp, comprises a splice donor site from the CMV major immediate-early promoter about 140 bp upstream of a splice acceptor from an immunoglobulin gene, with the intervening region being supplied by an Ig variable region intron. The sequence of this region, from splice donor to splicew acceptor, is presented in SEQ ID NO: 3.

i. Construction of a Plasmid Encoding Retroviral Vector JW-2.

A plasmid, pJW-2, encoding a retroviral vector for expressing full length factor VIII is constructed using the KT-1 backbone from pKT-1. To facilitate directional cloning of the factor VIII cDNA insert into pKT-1, the unique Xho I site is convened to a Not I site by site directed mutagenesis. The resultant plasmid vector is then opened with Not I and Cla I. pCIS-F8 is digested to completion with Cla I and Eag I, for which there are two sites, to release the fragment encoding full length factor VIII. This fragment is then ligated into the Not I/Cla I restricted vector to generate a plasmid designated pJW-2.

ii. Construction of a Plasmid Encoding Retroviral Vector ND-5.

A plasmid vector encoding a truncation of about 80% (approximately 370 bp) of the 3' untranslated region of the factor VIII cDNA, designated pND-5, is constructed in a pKT-1 vector as follows: As described for pJW-2, the pKT-1 vector employed has its Xho I restriction site replaced by that for Not I. The factor VIII insert is generated by digesting pCIS-F8 with Cla I and Xba I, the latter enzyme cutting 5' of the factor VIII stop codon. The approximately 7 kb fragment containing all but the 3' coding region of the factor VIII gene is then purified. pCIS-F8 is also digested with Xba I and Pst I to release a 121 bp fragment containing the gene's termination codon. This fragment is also purified and then ligated in a three way ligation with the larger fragment encoding the rest of the factor VIII gene and Cla I/Pst I restricted BLUESCRIPT® KS$^+$ plasmid (Stratagene, supra) to produce a plasmid designated pND-2.

The unique Sma I site in pND-2 is then changed to a Cla I site by ligating Cla I linkers (New England Biolabs, Beverly, Mass.) under dilute conditions to the blunt ends created by a Sma I digest. After recircularization and ligation, plasmids containing two Cla I sites are identified and designated pND-3.

The factor VIII sequence in pND-3, bounded by Cla I sites and containing the full length gene with a truncation of much of the 3' untranslated region, is cloned as follows into a plasmid backbone derived from a Not I/Cla I digest of pJW-1 [a pKT-1 derivative by cutting at the Xho I site, blunting with Klenow, and inserting a Not I linker (New England Biolabs)], which yields a 5.2 kb Not I/Cla I fragment. pCIS-F8 is cleaved with Eag I and Eco RV and the resulting fragment of about 4.2 kb, encoding the 5' portion of the full length factor VIII gene, is isolated. pND-3 is digested with Eco RV and Cla I and a 3.1 kb fragment is isolated. The two fragments containing portions of the factor VIII gene are then ligated into the Not I/Cla I digested vector backbone to produce a plasmid designated pND-5.

As those in the art will appreciate, after construction of plasmids encoding retroviral vectors such as those described above, such plasmids can then be used in the production of various cell lines from which infectious recombinant retroviruses can be produced. The production of such cell lines is described in the following example.

Example 2

Production of Cell Lines to Make Retroviral Vector Particles Comprising a Full Length Factor VIII Gene In this example, procedures are described for making packaging and producer cell lines which can make recombinant retroviral particles coding for full length factor VIII. Specifically, production of three packaging cell lines, DA (an amphotropic packaging cell line derived from the canine cell line D 17), HX (a xenotropic packaging cell line derived from the human cell line HT1080), and their packaging intermediates is described below.

A. Generation of an Amphotropic Packaging Cell Line

As an initial step in generating gag/pol packaging cell line intermediates, D17 cells and HT1080 are co-transfected with 1 μg of the methotrexate resistance vector, pFR400 (Graham and van der Eb, *Virology*, 52:456, 1973), and 10 μg of the MoMLV gag/pol expression vector pSCV10 by calcium phosphate co-precipitation (Graham and van der Eb, supra). pSCV10 is generated by combining a 0.7 kb Hinc II/Xma III fragment encompassing the CMV MIE transcriptional promoter (Boshart, et al, *Cell*, 41:521, 1985), a 5.3 kb Pst I(partial)/Sca I fragment from the MoMLV proviral plasmid MLV-K (Miller, et al., *Mol. Cell Biol.*, 5:531, 1985) encompassing the gag/pol coding region, and a 0.35 kb Dra I fragment from SV40 DNA (residues 2717–2363) encompassing the SV40 late transcriptional termination signal into the BLUESCRIPT® vector SK$^+$ using linkers and other standard recombinant DNA techniques.

Transfected cells are selected using dipyrimidol and methotrexate. Individual drug resistant cell colonies are expanded and analyzed for gag/pol expression by extracellular reverse transcriptase (RT) activity (modified from Goff, et al., *J. Virol.*, 38:239, 1981) and intracellular p30$^{gag}$ by Western blot using anti p30 antibodies (goat antiserum #77S000087 from the National Cancer Institute). This method identified individual cell clones in each cell type which expressed 10–50× higher levels of both proteins as compared to those produced by a standard mouse amphotropic packaging cell line, PA317 (U.S. Ser. No. 07/800,921, filed Nov. 27, 1991; ATCC CRL 9078).

To make amphotropic packaging cell lines, D17 and HT1080 cell lines that express high levels of gag/pol are co-transfected as described above except that 1 μg of a phleomycin resistance vector, pUT507 (Mulsant, et al., 14:243, 1988), and 10 μg of the amphotropic envelope expression vector pCMVenvAmNhe, are used. After phleomycin selection, individual drug resistant cell colonies are expanded and analyzed for intracellular gp80$^{env}$ expression by Western blot using anti gp70 (goat antiserum #79S000771 from N.C.I.). Several clones of each cell type are identified which express relatively high levels of both gag/pol and amphotropic env.

i. "G-Hopping"

Highest titers are obtained when retroviral vectors are introduced into packaging cell lines by infection, as opposed to transfection (Miller, et al., *Somat. Cell Mol. Genet.*, 12:175, 1986). Although amphotropic MLV vectors are known to infect these host cell types, the packaging cell lines DA and HA are blocked for infection by amphotropic vectors since they express an amphotropic env protein (i.e., "viral interference"). To overcome the problem of "viral interference," whereby cell lines expressing an amphotropic envelope protein block later infection by amphotropic MLV vectors able to otherwise infect those cell types, vector particles containing other viral envelopes (such as xenotropic env or VSV G protein, which bind to cell receptors other than the amphotropic receptor) may be generated in the following manner. 10 μg of the plasmid DNA encoding the retroviral vector to be packaged is co-transfected into a cell line which expresses high levels of gag/pol with 10 μg of DNA from which either xenotropic env or a VSV G protein is expressed. The resultant vector, containing xenotropic env or VSV G protein, respectively, is produced transiently in the co-transfected cells. Two days after transfection, cell free supernatants are added to prospective packaging cell lines (which express gag, pol, and env). Both types of vector efficiently infect the cells blocked for infection by amphotropic retrovirus. Cell free supernatants are then collected from the confluent monolayers and titered by PCR. Cell clones producing the highest liters are selected as packaging cell lines and are referred to as DA (D17 expressing an amphotropic env) and HA (HT1080 expressing an amphotropic env) cells.

B. Generation of a Xenotropic Packaging Cell Line

In contrast to amphotropic retroviral particles, particles produced from xenotropic packaging cell lines will exhibit a broad host range and thus will likely be useful in transducing a more broad spectrum of cell types and/or cells from different species. Retroviral particles produced from such xenotropic packaging cell lines may also exhibit higher transduction efficiencies, etc. Xenotropic packaging cell lines can be generated in a fashion similar to that described for making amphotropic packaging cell lines. For instance, HT1080 cell lines identified as gag/pol over-expressors are co-transfected as described above except that 1 µg of pUT507, supra, and 10 µg of a xenotropic envelope expression vector, pCMVxeno, is used. pCMVxeno is made using linkers and other standard recombinant DNA techniques to join the CMV early promoter and SV40 late termination signal described for pSCV10, supra, with an isolated 2.2 kb Nae I/Nhe I fragment containing the coding region from xenotropic envelope obtained from clone NZB9-1 (O'Neill, et al., *J. Virol.,* 53:100, 1985) in the order CMV promoter-envelope-termination signal. After phleomycin selection, individual drug resistant cell colonies are expanded and analyzed for intracellular expression of MLV $p30^{gag}$ and $gp75^{env}$ proteins by Western blot using specific antisera. Clones expressing relatively high levels of both gag/pol and xenotropic env are retained.

Again, to avoid viral interference during production of a xenotropic HT1080 producer cell line, i.e., that produces infectious retroviral particles encoding full length factor VIII, "G-hopping" as described above can be employed. 10 µg of the plasmid DNA encoding the retroviral vector to be packaged, e.g., pJW-2 or pND-5, is co-transfected into a cell line which expresses high levels of gag/pol with 10 µg of DNA from which VSV G protein is expressed. Recombinant retroviral particles are produced transiently. Two days after transfection, cell free supernatants are added to prospective HT1080 packaging cell lines which express gag, pol, and xenotropic env. Cell free supernatants are then collected from the confluent monolayers and titered by PCR. Cell clones producing the highest titers are selected as packaging cell lines and are referred to as HX (HT1080 expressing a xenotropic env) cells.

C. Generation of a Polytropic Packaging Cell Line

Recombinant retrovital particles containing a polytropic envelope will transduce few human cell types and thus may be used in an effort to target the recombinant retrovital vectors of the invention to only those cell types expressing the polytropic receptor on their cell membranes. As an example of the generation of a polytropic packaging cell line, a gag/pol over-expressor for HT1080 is co-transfected by the same techniques described above, except that 1 µg of the phleomycin resistance vector pUT507, supra, and 10 µg of the polytropic envelope expression vector pCMVMCF (containing a 2 kb Bam HI/Nhe I fragment encoding the polytropic envelope of MCF-247W (Holland, et al., *J. Virol.,* 53:152, 1985) in place of the MoMLV gag/pol of pSCV10, supra) are used. After phleomycin selection, individual drug resistant cell colonies are expanded and analyzed for intracellular expression of MLV $gp70^{env}$ protein by Western blot using specific antiserum.

As described above, retroviral vector particles containing VSV G protein are made by using 10 µg of plasmid DNA encoding the retroviral vector to be packaged, e.g., pJW-2 or pND-5, is co-transfected with 10 µg of DNA from which VSV G protein is expressed into a cell line which expresses high levels of gag/pol. Cell free supernatants from that culture are used to transduce HT1080 clones expressing relatively high levels of both gag/pol and polytropic env. Cell free supernatants are collected from the confluent monolayers and titered as described above. Clones expressing relatively high levels of both gag/pol and polytropic env are identified, retained, and designated "HP" (HT1080 expressing a polytropic env).

D. Detection of Replication Competent Retroviruses (RCR)

The propensity of the packaging cells described above to generate replication competent retrovirus is stringently tested by co-cultivating HX and DA packaging cells containing the vector N2. Since amphotropic vector can infect cells making the xenotropic envelope and vice versa, continuous cross-infection can occur, thereby increasing the probability of generating RCR. RCR is detected by assaying for the production of amphotropic and xenotropic retroviruses, as judged by a vector rescue assay on 293 or *Mus dunni* cells (NIH NIAID Bethesda, Md.), both of which can detect amphotropic and xenotropic retroviruses.

i. The Extended $S^+L^-$ Assay

The extended $S^+L^-$ assay determines whether replication competent, infectious virus is present in the supernatant of the cell line of interest. The assay is based on the empirical observation that infectious retroviruses generate foci on the indicator cell line $MiCl_1$ (ATCC No. CCL 64.1). The $MiCl_1$ cell line is derived from the Mv1Lu mink cell line (ATCC No. CCL 64) by transduction with Murine Sarcoma Virus (MSV). It is a non-producer, non-transformed, revertant clone containing a replication defective murine sarcoma provirus, $S^+$, but not a replication competent murine leukemia provirus, $L^-$. Infection of $MiCl_1$ cells with replication competent retrovirus "activates" the MSV genome to trigger "transformation" which results in foci formation.

Supernatant is removed from the cell line to be tested for presence of replication competent retrovirus and passed through a 0.45 µm filter to remove any cells. On day 1, Mv1Lu cells are seeded at $1.0\times10^5$ cells per well (one well per sample to be tested) on a 6 well plate in 2 mL Dulbecco's Modified Eagle Medium (DMEM), 10% FBS and 8 µg/mL polybrene. Mv1Lu cells are plated in the same manner for positive and negative controls on separate 6 well plates. The cells are incubated overnight at 37° C., 10% $CO_2$. On day 2, 1.0 mL of test supernatant is added to the Mv1Lu cells. The negative control plates are incubated with 1.0 mL of media. The positive control consists of three dilutions (200 focus forming units (ffu), 20 ffu and 2 ffu each in 1.0 mL media) of MA virus (Miller, et al., *Molec. and Cell Biol.,* 5:431, 1985) which is added to the cells in the positive control wells. The cells are incubated overnight. On day 3, the media is aspirated and 3.0 mL of fresh DMEM and 10% FBS is added to the cells. The cells are allowed to grow to confluency and are split 1:10 on day 6 and day 10, amplifying any replication competent retrovirus. On day 13, the media on the Mv1Lu cells is aspirated and 2.0 mL DMEM and 10% FBS is added to the cells. In addition, the $MiCl_1$ cells are seeded at $1.0\times10^5$ cells per well in 2.0 mL DMEM, 10% FBS and 8 µ/mL polybrene. On day 14, the supernatant from the Mv1Lu cells is transferred to the corresponding well of the $MiCl_1$ cells and incubated overnight at 37° C., 10% $CO_2$. On day 15, the media is aspirated and 3.0 mL of fresh DMEM and 10% FBS is added to the cells. On day 21, the cells are examined for focus formation (appearing as clustered, refractile cells that overgrow the monolayer and remain attached) on the monolayer of cells. The test article is determined to be contaminated with replication competent retrovirus if foci appear on the $MiCl_1$ cells. Using these procedures, it can be shown that full length factor VIII producer cell lines are not contaminated with replication competent retroviruses.

ii. Cocultivation of Producer Lines and MdH Marker Rescue Assay

As an alternate method to test for the presence of RCR in a vector-producing cell line, producer cells are cocultivated with an equivalent number of *Mus dunni* cells. Small scale co-cultivations are performed by mixing of 5.0×105 *Mus dunni* cells with $5.0\times10^5$ producer cells and seeding the mixture into 10 cm plates (10 mL standard culture media/plate, 4 µg/mL polybrene) at day 0. Every 3–4 days the cultures are split at a 1:10 ratio and 5.0×105 *Mus dunni* cells are added to each culture plate to effectively dilute out the producer cell line and provide maximum amplification of RCR. On day 14, culture supernatants are harvested, passed through a 0.45 µm cellulose-acetate filter, and tested in the MdH marker rescue assay. Large scale co-cultivations are performed by seeding a mixture of 1.0×108 *Mus dunni* cells and $1.0\times10^8$ producer cells into a total of twenty T-150 flasks (30 mL standard culture media/flask, 4 µg/mL polybrene). Cultures are split at a ratio of 1:10 on days 3, 6, and 13 and at a ratio of 1:20 on day 9. On day 15, the final supernatants are harvested, filtered and a portion of each is tested in the MdH marker rescue assay.

The MdH marker rescue cell line is cloned from a pool of *Mus dunni* cells transduced with LHL, a retroviral vector encoding the hygromycin B resistance gene (Palmer, et al., *Proc. Nat'l. Acad. Sci. USA*, 84:1055, 1987). The retroviral vector can be rescued from MdH cells upon infection of the cells with RCR. One mL of test sample is added to a well of a 6-well plate containing $1\times10^5$ MdH cells in 2 mL standard culture medium (DMEM with 10% FBS, 1% 200 mM L-glutamine, 1% non-essential amino acids) containing 4 µg/mL polybrene. Media is replaced after 24 hours with standard culture medium without polybrene. Two days later, the entire volume of MdH culture supernatant is passed through a 0.45 µm cellulose-acetate filter and transferred to a well of a 6-well plate containing $5.0\times10^4$ *Mus dunni* target cells in 2 mL standard culture medium containing polybrene. After 24 hours, supernatants are replaced with standard culture media containing 250 µg/mL of hygromycin B and subsequently replaced on days 2 and 5 with media containing 200 µg/mL of hygromycin B. Colonies resistant to hygromycin B appear and are visualized on day 9 post-selection, by staining with 0.2% Coomassie blue.

Example 3

Production of Retroviral Vector Particles Encoding Full Length Factor VIII

The production of JW-2 and ND-5 recombinant retroviral particles encoding full length factor VIII from the human xenotropic and canine amphotropic packaging cell lines HX and DA, respectively, are described below.

A. Transient Plasmid DNA Transfection of Packaging Cell Lines HX and DA with pND-5

The packaging cell line HX is seeded at $5.0\times10^5$ cells on a 10 cm tissue culture dish on day 1 with DMEM and 10% fetal bovine serum (FBS). On day 2, the media is replaced with 5.0 mL fresh media 4 hours prior to transfection. Standard calcium phosphate-DNA co-precipitations are performed by mixing 40.0 µl 2.5M $CaCl_2$, 10 µg of either of pJW-2 or pND-5, and deionized $H_2O$ to a total volume of 400 µl. The DNA-$CaCl_2$ solutions are then added dropwise with constant agitation to 400 µl of precipitation buffer (50 mM HEPES-NaOH, pH 7.1; 0.25M NaCl and 1.5 mM $Na_2HPO_4$-$NaH_2PO_4$). These mixtures are incubated at room temperature for 10 minutes. The resultant fine precipitates are added to different culture dishes of cells. The cells are incubated with the DNA precipitate overnight at 37° C. On day 3, the media is aspirated and fresh media is added. Supernatants are removed on day 4, passed through 0.45 µm filters, and stored at −80° C.

B. Packaging Cell Line Transduction

DA packaging cells are seeded at $1.0\times10^5$ cells/3 cm tissue culture dish in 2 mL DMEM and 10% FBS, 4 µg/mL polybrene (Sigma, St. Louis, Mo.) on day 1. On day 2, 3.0 mL, 1.0 mL and 0.2 mL of each of the freshly collected JW-2 or ND-5 retrovirus-containing HX supernatants are added to the cells. The cells are incubated overnight at 37° C. On day 3, the pools of cells are cloned by limiting dilution by removing the cells from the plate and counting the cell suspension, diluting the cells suspension down to 10 cells/mL and adding 0.1 mL to each well (1 cell/well) of a 96 well plate (Corning, Corning, N.Y.). Cells are incubated for 14 days at 37° C., 10% $CO_2$. Twenty-four clones producing JW-2 and 24 clones producing ND-5 are selected and expanded up to 24 well plates, 6 well plates, and finally to 10 cm plates, at which time the clones are assayed for expression of the appropriate retroviral vector and the supernatants are collected and assayed for retroviral liter.

The packaging cell line HX may also be transduced with either JW-2 or ND-5 recombinant retroviral vectors generated from a DA producer cell line in the same manner as described for transduction of the DA cells from the HX supernatants.

Using the procedures above, DA and HX cell lines are derived that produce either JW-2 or ND-5 retroviral vectors with titers greater than or equal to $1\times10^6$ cfu/mL in culture.

C. Titer Assays

As recombinant retroviral vectors encoding full length factor VIII, e.g., JW-2 and ND-5, do not include a gene coding for a selectable marker, titering assays other than those based on selection of drug resistant colonies are required. To this end, antibody and PCR assays, the latter of which is described below, may be employed to determine retroviral vector titer, i.e., the number of infectious particles comprising the retroviral vectors of the invention. To use PCR to amplify sequences unique to the retroviral vectors of the invention, various primers are required. Such primers can readily be designed by those skilled in the art and will depend on the retroviral vector backbone employed and the components thereof, the particular region(s) desired to be amplified, etc. Representative examples of particular primer pairs include those specific for LTR sequences, packaging signal sequences or other regions of the retroviral backbone, and also include primers specific for the full length factor VIII gene in the vector, which, due to its derivation from cDNA, lacks intron sequences likely to be present in endogenous factor VIII genomic sequences. Additional advantages in using such a PCR titering assay include the ability to assay for genome rearrangement, etc. As those in the art will appreciate, the PCR titering assay described below will also be applicable to gene transfer systems other than retroviral systems. For instance, it can be used to determine titers for gene transfer systems derived from adenoviruses, pox viruses, alphaviruses, direct or "naked" DNA, etc.

In the practice of the present invention, the PCR titering assay is performed by growing a known number of HT1080 cells, typically $1\times10^5$ cells, transduced with a retroviral vector capable of directing full length factor VIII expression on 6-well plates for at least 16 hr. before harvest. The retroviral vectors used for these transductions are obtained from either cell culture supernatants or blood. One well per plate is reserved for cell counting. Cells from the other wells are lysed and their contents isolated. DNA is prepared using a QIAmp Blood Kit for blood and cell culture PCR (QIAGEN, Inc., Chatsworth, Calif.). DNAs are resuspended at $5\times10^6$ cell equivalents/mL, where one cell equivalent is equal to the DNA content of one cell.

To calculate titer, a standard curve is generated using DNA isolated from untransduced HT1080 cells (negative control) and HT1080 cells transduced with a known vector and having one copy of that vector per cell genome (positive control), such as may be prepared from packaging cell lines transduced with a retroviral vector encoding a selectable marker, e.g., neomycin resistance. For both the positive and negative controls, DNA is resuspended at $5\times10^6$ cell equivalents/mL. The standard curve is generated by combining different amounts of the positive and negative control DNA, while keeping the total amount of DNA constant, and amplifying specific sequences therefrom by PCR using primers specific to a particular region of the retroviral vector. A representative group of mixtures for generating a standard curve is:

| Tube | 100% | 75% | 50% | 25% | 10% | 5% | 0% | Blank |
|---|---|---|---|---|---|---|---|---|
| Positive Control (μL) | 50 | 37.5 | 25 | 12.5 | 5 | 2.5 | 0 | 0 |
| Negative Control (μL) | 0 | 12.5 | 25 | 37.5 | 45 | 47.5 | 50 | 0 |
| Distilled water (μL) | 0 | 0 | 0 | 0 | 0 | 0 | 0 | 50 |

5.0 μL from each tube is placed into one of eight reaction tubes (duplicates are also prepared), with the remainder being stored at −20° C. 5.0 μL from each sample DNA preparation are placed into their own reaction tubes in duplicate. PCR reactions (50 μL total volume) are then initiated by adding 45.0 μL of a reaction mix containing the following components per tube to be tested: 24.5 μL water, 5 μL 10X reaction PCR buffer, 4 μL of 25 mM $MgCl_2$, 4 μL dNTPs (containing 2.5 mM of each of dATP, dGTP, dCTP, and dTTP), 5 μL of primer mix (100 ng or each primer), 0.25 μL TaqStart monoclonal antibody (Clontech Laboratories, Inc., Palo Alto, Calif.), 1.00 μL TaqStart buffer (Clontech Labs, Inc.), and 0.25 μL AmpliTaq DNA polymerase (Perkin-Elmer, Inc., Norwalk, Conn.). Just prior to aliquoting the reaction mix to the reaction tubes, 1 μL of $\alpha$-$^{32}$P dCTP (250 μCi; 3000 C/mmol, 10 mCi/mL, Amersham Corp., Arlington Heights, Ill.) is added into the reaction mix. After aliquoting 45.0 μL the reaction mix into each of the reaction tubes, the tubes are capped and placed into a thermocycler. The particular denaturation, annealing, elongation times and temperatures, and number of thermocycles will vary depending on size and nucleotide composition of the primer pair used. 20–25 amplification thermocycles are then performed. 5 μL of each reaction is then spotted on DE81 ion exchange chromatography paper (Whatman, Maidstone, England) and air dried for 10 min. The filter is then washed five times, 100 mL per wash, in 50 mM $Na_2PO_4$, pH 7, 200 mM NaCl, after which it is air dried and then sandwiched in Saran Wrap. Quantitation is performed on a PhosphoImager SI (Molecular Dynamics, Sunnyvale, Calif.). Filters are typically exposed to a phosphor screen, which stores energy from ionizing radiation, for a suitable period, typically about 120 min. After exposure, the phosphor screen is scanned, whereby light is emitted in proportion to the radioactivity on the original filter. The scanning results are then downloaded and plotted on a log scale as cpm (ordinate) versus percent positive control DNA (abscissa). Titers (infectious units/mL) for each sample are calculated by multiplying the number of cells from which DNA was isolated by the percentage (converted to decimal form) determined from the standard curve based on the detected radioactivity, divided by the volume of retroviral vector used to transduce the cells. As will be appreciated by those in the art, other methods of detection, such as colorimetric methods, may be employed to label the amplified products.

D. Generation of a ND-5 Producer Cell Line via One Packaging Cell Line

In some situations it may be desirable to avoid using more than one cell line in the process of generating producer lines. For example, DA cells are seeded at $5.0\times10^5$ cells on a 10 cm tissue culture dish on day 1 with DMEM and 10% irradiated (2.5 megarads minimum) FBS. On day 2, the media is replaced with 5.0 mL fresh media 4 hours prior to transfection. A standard calcium phosphate-DNA co-precipitation is performed by mixing 60 μl 2.0M $CaCl_2$, 10 lag of a plasmid from which VSV G will be expressed, 10 μg pND-5 retroviral vector plasmid, and deionized water to a volume of 400 pl. The DNA-$CaCl_{12}$ solution is then added dropwise with constant agitation to 400 μl of 2X precipitation buffer (50 mM HEPES-NaOH, pH 7.1, 0.25M NaCl and 1.5 mM $Na_2HPO_4$-$NaH_2PO_4$). This mixture is incubated at room temperature for 10 minutes. The resultant fine precipitate is added to a culture dish of DA cells plated the previous day. The cells are incubated with the DNA precipitate overnight at 37° C. On day 3, the medium is removed and fresh medium is added. The supernatant containing G-pseudotyped virus is removed on day 4, passed through a 0.45 μm filter and used to infect DA packaging cells as follows.

DA cells are seeded at $5.0\times10_5$ cells on a 10 cm tissue culture dish in 10 mL DMEM and 10% FBS, 4 mg/mL polybrene (Sigma, St. Louis, Mo.) on day 1. On day 2, 2.0 mL, 1.0 mL or 0.5 mL of the freshly collected and filtered G-pseudotyped retrovirus-containing supernatant is added to the cells. The cells are incubated with the retrovirus overnight at 37° C. Because no selectable marker is carded on the retroviral vector, no selection step is employed. Instead, cell pools are tested for expression and then dilution cloned by removing the cells from the plate, counting the cell suspension, diluting the cell suspension down to 10 cells/mL and adding 0.1 mL to each well (1 cell/well) of a 96-well plate. Cells are incubated for 2 weeks at 37° C., 10% $CO_2$. Numerous clones are selected and expanded up to 24-well plates, then 6-well plates, and finally 10 cm plates, at which time the clones are assayed for expression and the supernatants are collected and assayed for retroviral titer as described above.

E. Reuroviral Vector-Mediated Transfer of Factor VIII Expression.

In order to test the ability of retroviral vectors made in accordance with the teachings herein to transfer factor VIII expression, cells must be transduced with such vectors and the media or, in the case of therapeutic treatment, blood must be analyzed for the amount of factor VIII produced. Cell lines or patient cells transduced with retroviral vectors according to the invention are examined for expression of factor VIII by Coatest factor VIII:C analysis or by standard clotting assay.

i. Coatest Assay

The coagulation cascade is triggered by activation of factor X (which becomes factor Xa) by factor IXa in the presence of calcium and phospholipids, and is greatly enhanced by factor VIII, which acts as a co-factor. By using an in vitro assay (COATEST®, Chromogenix AB, Monlndal, Sweden) where optimal amounts of calcium and phospholipids and an excess of factors IXa and X, the rate of activation of factor X depends solely on the amount of factor VIII. Factor Xa is known to hydrolyze the chromogenic substrate S-2222 (Bz-Ile-Glu(γ-OR)-Gly-Arg-pNA), releasing pNA which can be detected spectrophotometrically at 405 nm. Signal intensity is proportional to factor VIII activity. Using such an assay, the amount of factor VIII produced either in tissue culture or in a patient can be determined. One International Unit (IU) of factor VIII activity is that amount of activity measured in 1.0 mL of pooled normal human plasma. The assay is performed as follows:

Cell free media containing factor VIII is obtained. For patient samples, 9 volumes of blood is mixed with one volume of 0.1M sodium titrate, pH 7.5, and centrifuged at 2,000×g 5–20 min. at 20°–25° C. to pellet cells. Due to heat lability of factor VIII, plasma samples should be tested within 30 min. of isolation or stored immediately at −70° C, although as much as 20% of factor VIII activity may be lost during freezing and thawing. When culture media is assayed, cells are similarly removed by centrifugation and an equal volume of working buffer (Coatest Kit).

As discussed above, serum levels of factor VIII in non-hemophilic patients are in the range of 200 ng/mL. Depending upon the range of factor VIII expected, either above or below 20% of normal, either of the two procedures below are used. In either case, a standard curve based on dilutions of normal human plasma (1.0 IU factor VIII/mL) is used and the assays should be performed in plastic tubes. When factor VIII levels are expected to be 20% or more of normal, a solution is prepared containing one volume of phospholipid emulsified from porcine brain and 5 volumes of reconstituted, lyophilized factor IX and factor X prepared as described by the manufacturer. This solution is stored at 2°–8° C. In an adaptation of the Coatest assay procedure for use on 96 well Falcon plates, 40 μL of this solution is mixed with 20 μL of plasma plus 20 μL of working buffer. The mixture is incubated at 37° C. for 4–5 min., after which 20 μL of a 0.025M $CaCl_2$ stock solution is added, followed by a 5 min. 37° C. incubation. 40 μL of the chromogenic reagent (20 mg S-2222, 335 μg synthetic thrombin inhibitor, I-2581, in 10 mL) is then mixed in. After a 5 min. incubation at 37° C., 20 μL of 20% acetic acid or 2% citric acid is added to stop the reaction. Absorbance is then measured against a blank comprising 50 mM Tris, pH 7.3, and 0.2% bovine serum albumin (BSA).

ii. Transfer of Expression in HT1080 using G-pseudotyped JW-2

$1.0\times10^4$ HT1080 cells are seeded into each well of a 6 well plate containing 2 mL of DMEM, 10% FBS, and 4 mg/mL polybrene. The next day, 1–2 mL of supernatant obtained from DA cells transfected with a VSV G-encoding expression vector and pJW-2 is added to each well. After the cells become confluent (normally 5–6 days post-infection), media is harvested from each well and subjected to a Coatest assay.

iii. Transfer of Expression in HT1080 using HX/JW-2

$1.0\times10_4$ HT1080 cells are seeded into each well of a 6 well plate containing 2 mL of DMEM, 10% FBS, and 4 mg/mL polybrene. The next day, 1–2 mL of supernatant obtained from HX cells transfected with pJW-2 is added to each well. After the cells become confluent, media is harvested from each well and subjected to a Coatest assay. These results, when correlated with those of a standard curve generated using dilutions of pooled normal human plasma, indicate that the HT1080 cells transduced with HX/JW-2 secrete about 30 ng/day/$10^6$ cells of factor VIII into the media.

iv. Transfer of Expression in HT1080 using HX/ND-5

Experiments similar to those for HX/JW-2 but using HT1080 cells transduced with retroviral vectors produced from a dilution cloned HX/ND-5 producer cell line and having a PCR-determined titer of $1.2\times10^4$ vectors/mL reveal that factor VIII is produced and secreted in transduced HT1080 cells at a level of at least 5 times that observed for HX/JW-2.

v. Transfer of Expression in Primary Human Fibroblasts using HX/JW-2

Figure 4A:
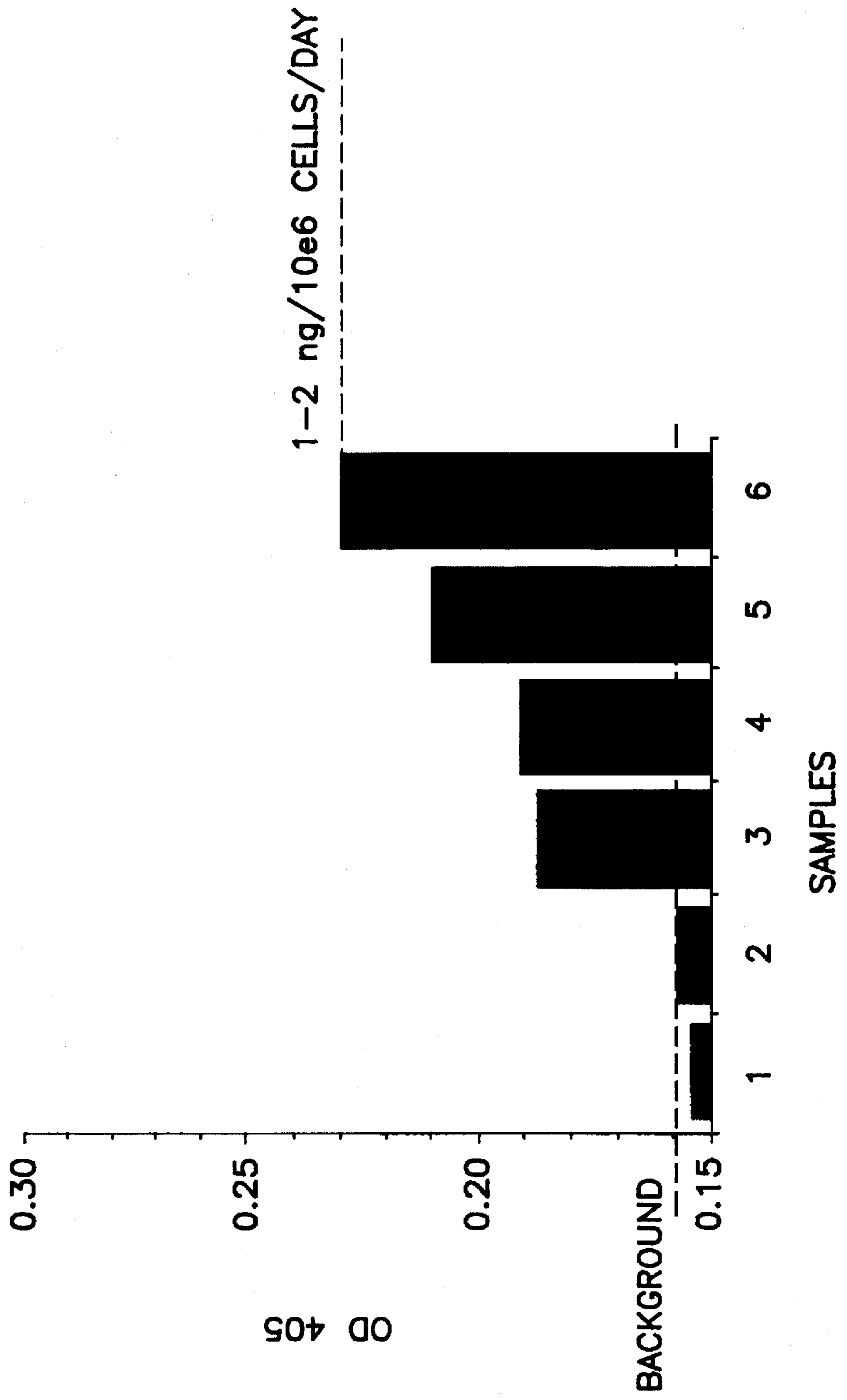
FIG. 4(A–B). Graph 4A shows factor VIII expression in primary human fibroblasts as measured by Coatest assay. Samples 1 and 2 represent untransduced controls and samples 3–6 are expression levels from fibroblasts transduced with 0.44 mL, 0.133 mL, 0.400 mL, and 1.2 mL of supernatant containing HX/JW-2, respectively. Graph 4B is a Coatest standard curve.
Figure 4B:
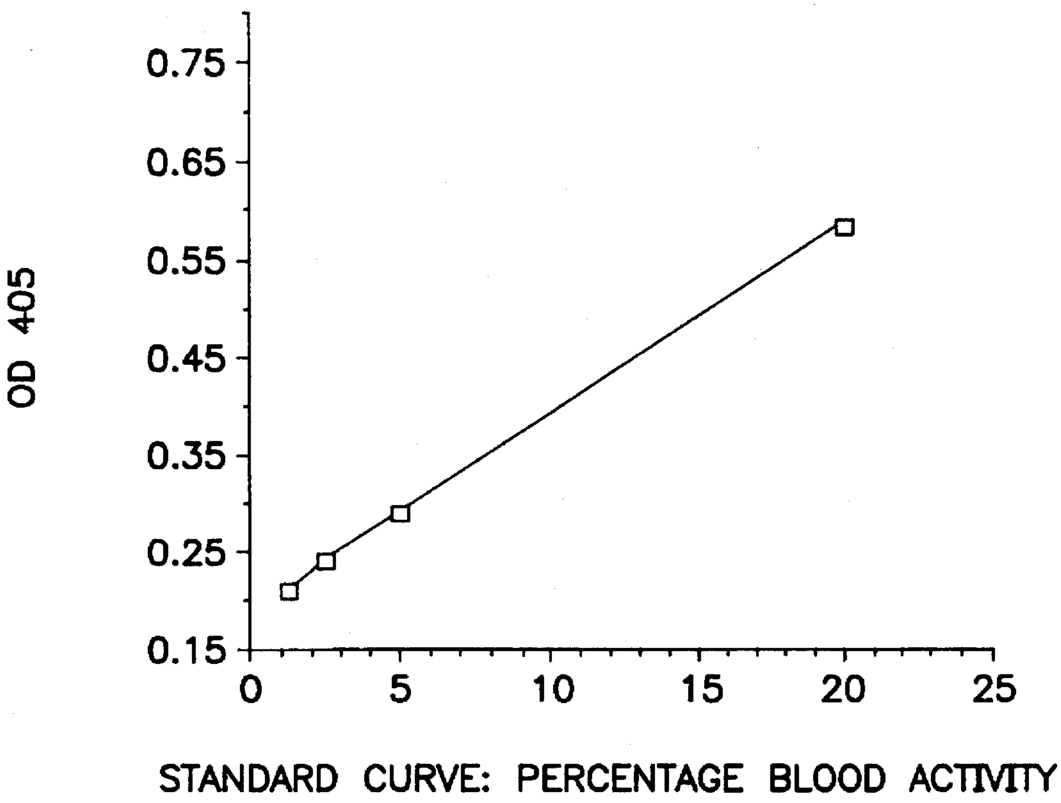

Transfer of expression in primary human fibroblasts obtained from a skin punch biopsy taken from the forearm of a human volunteer is conducted by seeding approximately $3\times10^4$ primary human fibroblasts in each well of a 6 well plate. The cells are grown in 2 mL/well of Modified Eagle's Minimal Media (Irvine Scientific, Santa Ana, Calif.) containing 15% FBS and 200 mM L-glutamine. The day after seeding, various amounts of supernatant (44 μL, 133 μL, and 400 μL) obtained from DA cells transfected with a VSV G-encoding expression vector and pJW-2 diluted to a total volume of 1–2 mL is added to each well. After the cells become confluent (normally 3–6 days post-infection), media is harvested from each well and subjected to a Coatest assay. The level of factor VIII expressed from these cells, as measured by Coatest assay, are shown in FIG. 4.

Example 4

Production of Retroviral Vector Particles Encoding Full Length Factor VIII

A. Production and Purification

Crude recombinant retroviral particles encoding full length factor VIII are obtained from a Celligan bioreactor (New Brunswick, New Brunswick, N.J.) containing DA or HX cells transduced with a recombinant retroviral vector according to the invention bound to the beads of the bioreactor matrix. The cells release the recombinant retroviral particles into the growth media that is passed over the cells in a continuous flow process. The media exiting the bioreactor is collected and passed initially through a 0.8 μm filter and then through a 0.65 μm filter to clarify the supernatant. This retroviral particle-containing filtrate is concentrated utilizing a cross flow concentrating system (Filtron, Boston, Mass.). Approximately 50 units of DNase (Intergen, New York, N.Y.) per mL of concentrate is added to digest exogenous DNA. The digest is diafiltrated in the same cross flow system against 150 mM NaCl mM tromethamine, pH 7.2. The diafiltrate is loaded onto a Sephadex S-500 gel column (Pharmacia, Piscataway, N.J.), equilibrated in 50 mM NaCl, 25 mM tromethamine, pH 7.4. The purified recombinant retrovirus is eluted from the Sephadex S-500 gel column in 50 mM NaCl, 25 mM tromethamine, pH 7.4.

B. Formulation

Formulation buffer containing lactose, mannitol, sucrose, or trehalaose is prepared at a 2x concentrated stock solution. The formulation buffer contains 25 mM tromethamine, 70 mM NaCl, 2 mg/mL arginine, 10 mg/mL human serum albumin (HSA), and 100 mg/mL lactose, mannitol, sucrose, or trehalose in a final volume of 100 mls at pH 7.4.

The purified recombinant retrovirus is formulated by adding one part 2x formulation buffer to one part S-500-purified recombinant retrovirus. The formulated recombinant retroviral particles can be stored in liquid at −70° C. to −80° C. or dried.

To dry the retroviral preparation, the formulated retroviral particles are aliquoted into vials and lyophilized in an Edwards Refrigerated Chamber (3 Shelf RC3S unit) attached to a Supermodulyo 12K freeze dryer (Edwards High Vacuum, Tonawanda, N.Y.). When the freeze drying cycle is completed, the vials are stoppered under a vacuum following a slight nitrogen gas bleeding and aluminum seals are crimped on. The lyophilized product can be stored at −20° C. for long periods without a significant loss of titer, as measured by a PCR titering assay, supra, following reconstitution.

The lyophilized recombinant retrovirus is reconstituted with 1.0 ml water. The infectivity of the reconstituted recombinant retrovirus is determined by a titer activity assay. The assay is conducted on HT 1080 fibroblasts or 3T3 mouse fibroblast cell line (ATCC CCL 163). Specifically, $1.0\times10^5$ cells are plated onto 6 cm plates and incubated overnight at 37° C., 10% $CO_2$. Ten microliters of a dilution series of reconstituted recombinant retroviruses are added to the cells in the presence of 4 μmL polybrene (Sigma, St. Louis, Mo.) and incubated overnight at 37° C., 10% $CO_2$. Following incubation, cells are selected for neomycin resistance in G418 containing media and incubated for 5 days at 37° C., 10% $CO_2$. Following initial selection, the cells are re-fed with fresh media containing G418 and incubated for 5 to 6 days. After final selection, the cells are stained with Commassie blue for colony detection. The titer of the sample is determined from the number of colonies, the dilution and the volume used.

While the present invention has been described above both generally and in terms of preferred embodiments, it is understood that variations and modifications will occur to those skilled in the art in light of the description, supra. Therefore, it is intended that the appended claims cover all such variations coming within the scope of the invention as claimed.

Additionally, the publications and other materials cited to illuminate the background of the invention, and in particular, to provide additional details concerning its practice as described in the detailed description and examples, are hereby incorporated by reference in their entirety.

We claim:

1. A retrovital vector comprising gene expression control elements operably linked to a nucleotide sequence encoding a full-length factor VIII polypeptide.

2. A retroviral vector according to claim 1 wherein the retrovirus is selected from the group consisting of MoMLV, GALV, FeLV, and FIV.

3. A retroviral vector according to claim 1 wherein said gene expression control elements comprise a viral promoter.

4. A retrovital vector according to claim 3 wherein said viral promoter is selected from the group consisting of a retroviral LTR promoter, a SV40 promoter, a CMV MIE promoter, and a MPMV promoter.

5. An ex vivo host cell transfected or transduced by a retrovital vector according to claim 1.

6. An ex vivo producer cell comprising a nucleic acid construct which expresses retrovital structural proteins and also comprising the retrovital vector according to claim 1, wherein said producer cell packages said retrovital vector in association with said structural proteins to produce recombinant retrovital particles.

7. A recombinant retroviral particle comprising the retroviral vector of claim 1 in association with structural proteins.

8. A retrovital vector comprising gene expression control elements operably linked to a nucleotide sequence encoding a full-length factor VIII polypeptide, wherein the full-length factor VIII polypeptide is encoded by a nucleic acid molecule selected from the group consisting of:

(a) a nucleotide sequence set forth in SEQ ID NO: 1, except that a uracil ("U") replaces every thymine ("T");

(b) a nucleotide sequence which would hybridize under stringent conditions to the complementary nucleotide sequence of (a); and (c) a nucleotide sequence which, but for the degeneracy of the genetic code, would hybridize to the nucleotide sequences of (a) or (b).

9. A retrovital vector according to claim 8 wherein the retrovirus is selected from the group consisting of MoMLV, GALV, FeLV, and FIV.

10. A retroviral vector according to claim 8 wherein said gene expression control elements comprise a viral promoter.

11. A retroviral vector according to claim 10 wherein said vital promoter is selected from the group consisting of a retrovital LTR promoter, a SV40 promoter, a CMV MIF promoter, and a MPMV promoter.

12. An ex vivo host cell transfected or transduced by a retrovital vector according to claim 8.

13. An ex vivo producer cell comprising a nucleic acid construct which expresses retrovital structural proteins, and also comprising the retrovital vector according to claim 8, wherein said producer cell packages said retroviral vector in association with said packaging structural proteins to produce recombinant retroviral particles.

14. A recombinant retrovital particle comprising the retroviral vector of claim 8 and in association with retrovital structural proteins.

* * * * *